US011697851B2

(12) United States Patent
Barrett et al.

(10) Patent No.: US 11,697,851 B2
(45) Date of Patent: Jul. 11, 2023

(54) EARLY OVARIAN CANCER DETECTION DIAGNOSTIC TEST BASED ON MRNA ISOFORMS

(71) Applicant: The Regents of the University of California, Oakland, CA (US)

(72) Inventors: Christian Barrett, Pacific Beach, CA (US); Dennis A. Carson, La Jolla, CA (US); Kelly Frazer, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 360 days.

(21) Appl. No.: 15/604,400

(22) Filed: May 24, 2017

(65) Prior Publication Data

US 2017/0342504 A1 Nov. 30, 2017

Related U.S. Application Data

(60) Provisional application No. 62/340,876, filed on May 24, 2016.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,689,338 A | 8/1987 | Gerster |
| 4,929,624 A | 5/1990 | Gerster et al. |
| 4,938,949 A | 7/1990 | Borch et al. |
| 5,037,986 A | 8/1991 | Gerster |
| 5,175,296 A | 12/1992 | Gerster |
| 5,238,944 A | 8/1993 | Wick et al. |
| 5,352,784 A | 10/1994 | Nikolaides et al. |
| 5,367,076 A | 11/1994 | Gerster |
| 5,395,937 A | 3/1995 | Nikolaides et al. |
| 5,444,065 A | 8/1995 | Nikolaides et al. |
| 5,624,677 A | 4/1997 | El-Rashidy et al. |
| 5,627,281 A | 5/1997 | Nikolaides et al. |
| 5,648,516 A | 7/1997 | Nikolaides et al. |
| 5,693,811 A | 12/1997 | Lindstrom |
| 5,736,553 A | 4/1998 | Wick et al. |
| 5,741,908 A | 4/1998 | Gerster et al. |
| 5,998,619 A | 12/1999 | Gerster et al. |
| 6,038,505 A | 3/2000 | Probst et al. |
| 6,039,969 A | 3/2000 | Tomai et al. |
| 6,083,505 A | 7/2000 | Miller et al. |
| 6,150,523 A | 11/2000 | Gerster et al. |
| 6,200,592 B1 | 3/2001 | Tomai et al. |
| 6,245,776 B1 | 6/2001 | Skwiercynski et al. |
| 6,329,381 B1 | 12/2001 | Kurimoto et al. |
| 6,333,331 B1 | 12/2001 | Moschel et al. |
| 6,372,725 B1 | 4/2002 | Zilch et al. |
| 6,437,131 B1 | 8/2002 | Gerster et al. |
| 6,486,168 B1 | 11/2002 | Skwierczynski et al. |
| 6,534,654 B2 | 3/2003 | Gerster et al. |
| 6,552,192 B1 | 4/2003 | Hanus et al. |
| 6,610,319 B2 | 8/2003 | Tomai et al. |
| 6,613,902 B2 | 9/2003 | Gerster et al. |
| 6,624,305 B2 | 9/2003 | Gerster |
| 6,696,076 B2 | 2/2004 | Tomai et al. |
| 6,706,728 B2 | 3/2004 | Hedenstrom et al. |
| 6,716,840 B2 | 4/2004 | Chu et al. |
| 6,733,764 B2 | 5/2004 | Martin |
| 6,734,187 B1 | 5/2004 | Tanaka et al. |
| 6,897,314 B2 | 5/2005 | Gerster et al. |
| 6,960,582 B2 | 11/2005 | Boyce et al. |
| 7,001,609 B1 | 2/2006 | Matson et al. |
| 7,037,929 B1 | 5/2006 | Pevarello et al. |
| 7,157,465 B2 | 1/2007 | Isobe et al. |
| 7,189,727 B2 | 3/2007 | Boyce |
| 7,238,700 B2 | 7/2007 | Palle et al. |
| 7,241,890 B2 | 7/2007 | Kasibhatla et al. |
| 7,521,454 B2 | 4/2009 | Isobe et al. |
| 7,576,068 B2 | 8/2009 | Averett |
| 7,754,728 B2 | 7/2010 | Isobe et al. |
| 7,968,544 B2 | 6/2011 | Graupe et al. |
| 8,211,863 B2 | 7/2012 | Averett |
| 8,357,374 B2 | 1/2013 | Carson et al. |

(Continued)

FOREIGN PATENT DOCUMENTS

| | | |
|---|---|---|
| AU | 2007257423 | 5/2012 |
| AU | 2006283524 B2 | 3/2013 |

(Continued)

OTHER PUBLICATIONS

Barrett et al; PNAS, E3050-E3057; May 26, 2015.*
David, Charles J, "Alternative pre-mRNA splicing regulation in cancer: pathways and programs unhinged", Genes and Development, vol. 24, [Online] Retrieved from the Internet: <URL: http://www.genesdev.org/cgi/doi/10.1101/gad.1973010>, (2010), 2343-2364.
Hemler, Martin E, "Tetraspanin proteins promote multiple cancer stages", Nature Reviews Cancer, vol. 14, (Jan. 2014), 49-60.
Hwang, Jae Ryoung, "Upregulation of CD9 in ovarian cancer is related to the induction of TNF-alpha gene expression and constitutive NF-kappa Beta activation", Carcinogenesis Advance Access, (Nov. 16, 2011), 7 pgs.
Lam, Andy Ky, "FOXM1b, which is present at elevated levels in cancer cells, has a greater transforming potential than FOXM1c", Frontiers in Oncology, 3(11), (Jan. 2012), 5 pgs.

(Continued)

*Primary Examiner* — Jehanne S Sitton
(74) *Attorney, Agent, or Firm* — Schwegman Lundberg & Woessner, P.A.

(57) ABSTRACT

A method to detect ovarian cancer is provided that employs probes and/or primers to detect certain RNA isoform transcripts, as well as kits therefor.

18 Claims, 8 Drawing Sheets
(8 of 8 Drawing Sheet(s) Filed in Color)
Specification includes a Sequence Listing.

(56) References Cited

U.S. PATENT DOCUMENTS

| | | |
|---|---|---|
| 8,729,088 B2 | 5/2014 | Carson et al. |
| 8,790,655 B2 | 7/2014 | Carson |
| 8,846,697 B2 | 9/2014 | Carson et al. |
| 9,050,376 B2 | 6/2015 | Carson et al. |
| 9,173,931 B2 | 11/2015 | Jessouroun et al. |
| 9,359,360 B2 | 6/2016 | Carson et al. |
| 9,505,768 B2 | 11/2016 | Carson et al. |
| 2002/0127224 A1 | 9/2002 | Chen |
| 2002/0193595 A1 | 12/2002 | Chu et al. |
| 2003/0003505 A1 | 1/2003 | Cook |
| 2003/0187261 A1 | 10/2003 | Havlicek et al. |
| 2003/0191086 A1 | 10/2003 | Hanus et al. |
| 2004/0023211 A1 | 2/2004 | Groen et al. |
| 2004/0091491 A1 | 5/2004 | Kedl et al. |
| 2004/0132748 A1 | 7/2004 | Isobe et al. |
| 2004/0202663 A1 | 10/2004 | Hu et al. |
| 2004/0209899 A1 | 10/2004 | Palle et al. |
| 2004/0248895 A1 | 12/2004 | Chu et al. |
| 2004/0265351 A1 | 12/2004 | Miller et al. |
| 2005/0004038 A1 | 1/2005 | Lyon et al. |
| 2005/0004144 A1 | 1/2005 | Carson et al. |
| 2005/0038027 A1 | 2/2005 | Boyce |
| 2005/0042272 A1 | 2/2005 | Hou et al. |
| 2005/0049263 A1 | 3/2005 | Kasibhatla et al. |
| 2005/0059613 A1 | 3/2005 | Memarzadeh et al. |
| 2005/0158325 A1 | 7/2005 | Hammerbeck et al. |
| 2005/0054590 A1 | 10/2005 | Averett |
| 2005/0266067 A1 | 12/2005 | Sengupta et al. |
| 2006/0052403 A1 | 3/2006 | Isobe et al. |
| 2006/0110746 A1 | 5/2006 | Andre et al. |
| 2007/0037832 A1 | 2/2007 | Isobe et al. |
| 2007/0087009 A1 | 4/2007 | Burdin |
| 2007/0100146 A1 | 5/2007 | Dzwiniel |
| 2007/0161582 A1 | 7/2007 | Mijikovic et al. |
| 2007/0173483 A1 | 7/2007 | Kasibhatla et al. |
| 2007/0173530 A1 | 7/2007 | Mitchell et al. |
| 2007/0190071 A1 | 8/2007 | Kurimoto et al. |
| 2007/0292418 A1 | 12/2007 | Fields et al. |
| 2008/0008682 A1 | 1/2008 | Chong et al. |
| 2008/0125446 A1 | 5/2008 | Kasibhatla et al. |
| 2008/0214580 A1 | 9/2008 | Neagu et al. |
| 2009/0047249 A1 | 2/2009 | Graupe et al. |
| 2009/0053186 A1 | 2/2009 | Hu et al. |
| 2009/0069289 A1 | 3/2009 | Neagu et al. |
| 2009/0099212 A1 | 4/2009 | Zablocki et al. |
| 2009/0105212 A1 | 4/2009 | Isobe et al. |
| 2009/0118263 A1 | 5/2009 | Hashimoto et al. |
| 2009/0202484 A1 | 8/2009 | Chong et al. |
| 2009/0202626 A1 | 8/2009 | Carson et al. |
| 2009/0263470 A1 | 10/2009 | Coller et al. |
| 2009/0324551 A1 | 12/2009 | Carson et al. |
| 2010/0029585 A1 | 2/2010 | Howbert et al. |
| 2010/0210598 A1 | 8/2010 | Carson et al. |
| 2011/0098248 A1 | 4/2011 | Halcomb et al. |
| 2011/0098294 A1 | 4/2011 | Carson et al. |
| 2011/0150836 A1 | 6/2011 | Halcomb et al. |
| 2011/0306671 A1 | 12/2011 | Carson et al. |
| 2011/0319442 A1 | 12/2011 | Leoni et al. |
| 2012/0003298 A1 | 1/2012 | Barberis et al. |
| 2012/0009247 A1 | 1/2012 | Maj et al. |
| 2012/0083473 A1 | 4/2012 | Holldack et al. |
| 2012/0128715 A1 | 5/2012 | Levy et al. |
| 2012/0148660 A1 | 6/2012 | Carson et al. |
| 2012/0177681 A1 | 7/2012 | Singh et al. |
| 2013/0156807 A1 | 6/2013 | Carson et al. |
| 2013/0165455 A1 | 6/2013 | Carson et al. |
| 2013/0190494 A1 | 7/2013 | Carson et al. |
| 2014/0255368 A1 | 9/2014 | Kim et al. |
| 2014/0302120 A1 | 10/2014 | Carson et al. |
| 2015/0197527 A1 | 7/2015 | Carson et al. |
| 2015/0203844 A1 | 7/2015 | Marban et al. |
| 2015/0366962 A1 | 12/2015 | Carson et al. |
| 2016/0193313 A1 | 7/2016 | Kim et al. |
| 2016/0199499 A1 | 7/2016 | Carson et al. |
| 2017/0165359 A1 | 6/2017 | Berzofsky et al. |
| 2018/0110784 A1 | 4/2018 | Carson et al. |
| 2020/0071668 A1 | 3/2020 | Kim et al. |
| 2020/0087625 A1 | 3/2020 | Carson et al. |
| 2020/0261562 A1 | 8/2020 | Vinetz |
| 2021/0038742 A1 | 2/2021 | Huang et al. |
| 2021/0187087 A1 | 6/2021 | Mcneel et al. |
| 2021/0380546 A1 | 12/2021 | Carson et al. |
| 2022/0152188 A1 | 5/2022 | Carson et al. |
| 2022/0305121 A1 | 9/2022 | Carson et al. |

FOREIGN PATENT DOCUMENTS

| | | |
|---|---|---|
| AU | 2008227128 B2 | 3/2013 |
| AU | 2009210655 B2 | 8/2013 |
| AU | 2010214112 B2 | 4/2015 |
| AU | 2020236254 A1 | 10/2021 |
| CA | 3132994 A1 | 9/2020 |
| CN | 101304748 A | 11/2008 |
| CN | 101790380 B | 7/2013 |
| CN | 102439011 B | 5/2016 |
| CN | 114401738 A | 4/2022 |
| DE | 1810053 | 2/1970 |
| EA | 019768 B1 | 6/2014 |
| EP | 0145340 A2 | 6/1985 |
| EP | 0310950 A1 | 4/1989 |
| EP | 0389302 A1 | 9/1990 |
| EP | 0394026 A1 | 10/1990 |
| EP | 0553202 A1 | 8/1993 |
| EP | 0575549 A1 | 12/1993 |
| EP | 0636031 A1 | 2/1995 |
| EP | 0681570 A1 | 11/1995 |
| EP | 0708773 A1 | 5/1996 |
| EP | 0912564 A1 | 5/1999 |
| EP | 0912565 A1 | 5/1999 |
| EP | 0938315 A1 | 9/1999 |
| EP | 1035123 A1 | 9/2000 |
| EP | 1035123 B1 | 8/2003 |
| EP | 1386923 A1 | 2/2004 |
| EP | 1550662 A1 | 7/2005 |
| EP | 1939202 A1 | 7/2008 |
| EP | 2396328 | 12/2011 |
| EP | 1931352 B1 | 4/2016 |
| EP | 3908316 A1 | 11/2021 |
| HK | 1170226 A | 2/2013 |
| HK | 1138767 B | 5/2014 |
| HK | 1177886 B | 7/2016 |
| JP | 11193282 A | 7/1999 |
| JP | 11269177 A | 10/1999 |
| JP | 2004137157 A | 5/2004 |
| JP | 2005046160 A | 2/2005 |
| JP | 2005505504 A | 2/2005 |
| JP | 200589334 A | 4/2005 |
| JP | 2005089334 A | 4/2005 |
| JP | 2005126374 A | 5/2005 |
| JP | 2006519784 A | 8/2006 |
| JP | 2007504232 A | 3/2007 |
| JP | 2009504803 A | 2/2009 |
| JP | 2009510096 A | 3/2009 |
| JP | 2010518082 A | 5/2010 |
| JP | 2012517428 A | 8/2012 |
| JP | 2013525431 A | 6/2013 |
| JP | 2014129425 A | 7/2014 |
| KR | 1020220035870 A | 3/2022 |
| WO | WO-9215581 A1 | 9/1992 |
| WO | WO-9320847 A1 | 10/1993 |
| WO | WO-9817279 A1 | 4/1998 |
| WO | WO-9848805 A1 | 11/1998 |
| WO | WO-9928321 A1 | 6/1999 |
| WO | WO-1999028321 A1 | 6/1999 |
| WO | WO-0043394 A1 | 7/2000 |
| WO | WO-0144259 A1 | 6/2001 |
| WO | WO-0144260 A2 | 6/2001 |
| WO | WO-0149688 A1 | 7/2001 |
| WO | WO-0224225 A1 | 3/2002 |
| WO | WO-0230399 A2 | 4/2002 |
| WO | WO-03077944 A1 | 9/2003 |
| WO | WO-2004029054 A1 | 4/2004 |
| WO | WO-2004066947 A2 | 8/2004 |
| WO | WO-2005025583 A2 | 3/2005 |

(56) References Cited

FOREIGN PATENT DOCUMENTS

| WO | WO-2005060966 A1 | 7/2005 |
|---|---|---|
| WO | WO-2005092892 A1 | 10/2005 |
| WO | WO-2006062945 A2 | 6/2006 |
| WO | WO-2006065234 A1 | 6/2006 |
| WO | WO-2006100226 A1 | 9/2006 |
| WO | WO-2006117670 A1 | 11/2006 |
| WO | WO-2007024707 A2 | 3/2007 |
| WO | WO-2007024707 A3 | 3/2007 |
| WO | WO-2007034817 A1 | 3/2007 |
| WO | WO-2007034917 A1 | 3/2007 |
| WO | WO-2007038720 A2 | 4/2007 |
| WO | WO-2007128158 A1 | 11/2007 |
| WO | WO-2007142755 A2 | 12/2007 |
| WO | WO-2007142755 A3 | 12/2007 |
| WO | WO-2008005555 A1 | 1/2008 |
| WO | WO-2008115319 A2 | 9/2008 |
| WO | WO-2008115319 A3 | 9/2008 |
| WO | WO-2009005687 A1 | 1/2009 |
| WO | WO-2009099650 A2 | 8/2009 |
| WO | WO-2009099650 A3 | 8/2009 |
| WO | WO-2009099650 A4 | 8/2009 |
| WO | WO-2009143457 A2 | 11/2009 |
| WO | WO-2010033074 A1 | 3/2010 |
| WO | WO-2010077310 A2 | 7/2010 |
| WO | WO-2010093436 A2 | 8/2010 |
| WO | WO-2010093436 A3 | 8/2010 |
| WO | WO-2010077310 A3 | 11/2010 |
| WO | WO-2011139348 A3 | 9/2011 |
| WO | WO-2011134668 A1 | 11/2011 |
| WO | WO-2011134669 A1 | 11/2011 |
| WO | WO-2011139348 A2 | 11/2011 |
| WO | WO-2011139348 A9 | 11/2011 |
| WO | WO-2014052828 A1 | 4/2014 |
| WO | WO-2015023858 A2 | 2/2015 |
| WO | WO-2015023858 A3 | 2/2015 |
| WO | WO-2016164640 A1 | 10/2016 |
| WO | WO-2016168680 A1 | 10/2016 |
| WO | WO-2018183930 A1 | 10/2018 |
| WO | WO-2019212356 A1 | 11/2019 |
| WO | WO-2020086625 A1 | 4/2020 |
| WO | WO-2020186229 A1 | 9/2020 |
| WO | WO-2021034729 A1 | 2/2021 |
| WO | WO-2022076473 A1 | 4/2022 |

OTHER PUBLICATIONS

Leth-Larsen, Rikke, "Functional Heterogeneity within the CD44 High Human Breast Cancer Stem Cell-Like Compartment Reveals a Gene Signature Predictive of Distant Metastasis", Molecular Medicine, vol. 18, (2012), 1109-21.
Reeves, David, "The Contribution of Social Networks to the Health and Self-Management of Patients with Long-Term Conditions: A Longitudinal Study", PLOS One, 9(6): e98340, (Jun. 2014), 12 pgs.
Venables, Julian P, "Cancer-associated regulation of alternative splicing", Nature Structural and Molecular Biology, 16(6):670-6, (May 2009), 8 pgs.
"8H-Purin-8-one, 6-amnino-2-(butylthio)-7,9-dihydro-9-(phenylme-thyl)-", CAS Registry No. 226906-70-3, (2012), 1 pg.
"8H-Purin-8-one, 6-amino-2-(cyclohexylthio)-7,9-dihydro-9-(phenylmethyl)-", CAS Registry No. 226906-76-9, 1 pg.
"8H-Purin-8-one, 6-amino-2-(ethylthio)-7,9-dihydro-9-(phenylme-thyl)-", CAS Registry No. 226906-67-8, 1 pg.
"8H-Purin-8-one, 6-amino-7,9-dihydro-2-(methylthio)-9-(phenylmethyl)-", CAS Registry No. 226906-66-7, 1 pg.
"8H-Purin-8-one, 6-amino-7,9-dihydro-2-(pentylthio)-9-(phenylme-thyl)-", CAS Registry No. 226906-73-6, 1 pg.
"8H-Purin-8-one, 6-amino-7,9-dihydro-2-[(1-methylethyl)thio]-9-(phenylmethyl)-", CAS Registry No. 226906-69-0, 1 pg.
"8H-Purin-8-one, 6-amino-7,9-dihydro-2-[(1-methylpropyl)thio]-9-(phenylmethyl)-", CAS Registry No. 226906-72-5, 1 pg.
"8H-Purin-8-one, 6-amino-7,9-dihydro-2-[(2-methylbutyl)thio]-9-(phenylmethyl)-", CAS Registry No. 226906-75-8, 1 pg.
"8H-Purin-8-one, 6-amino-7,9-dihydro-2-[(2-methylpropyl)thio]-9-(phenylmethyl)-", CAS Registry No. 226906-71-4, 1 pg.
"8H-Purin-8-one, 6-amino-7,9-dihydro-2-[(3-methylbutyl)thio]-9-(phenylmethyl)-", CAS Registry No. 226906-74-7, 1 pg.
"8H-Purin-8-one, 6-amino-7,9-dihydro-9-(phenylmethyl)-2-(phenylthio)-", CAS Registry No. 226906-77-0, 1 pg.
"8H-Purin-8-one, 6-amino-7,9-dihydro-9-(phenylmethyl)-2-(propylt-hio)-", CAS Registry No. 226906-68-9, 1 pg.
"U.S. Appl. No. 12/027,960, Amendment Under 37 C.F.R. Sec. 1.312 filed Nov. 1, 2012", 7 pgs.
"U.S. Appl. No. 12/027,960, Non Final Office Action dated Apr. 10, 2012", 16 pgs.
"U.S. Appl. No. 12/027,960, Notice of Allowance dated Aug. 1, 2012", 10 pgs.
"U.S. Appl. No. 12/027,960, Preliminary Amendment dated Dec. 8, 2010", 21 pgs.
"U.S. Appl. No. 12/027,960, PTO Response to 312 Amendment dated Nov. 14, 2012", 2 pgs.
"U.S. Appl. No. 12/027,960, Response filed Jul. 10, 2012 to Non Final Office Action dated Apr. 10, 2012", 8 pgs.
"U.S. Appl. No. 12/027,960, Response filed Oct. 24, 2011 to Restriction Requirement dated Sep. 23, 2011", 21 pgs.
"U.S. Appl. No. 12/027,960, Restriction Requirement dated Sep. 23, 2011", 9 pgs.
"U.S. Appl. No. 12/064,529, Final Office Action dated Sep. 20, 2012", 14 pgs.
"U.S. Appl. No. 12/064,529, Non Final Office Action dated Apr. 9, 2012", 15 pgs.
"U.S. Appl. No. 12/064,529, Preliminary Amendment filed Feb. 22, 2008", 11 pgs.
"U.S. Appl. No. 12/064,529, Response filed Jul. 9, 2012 to Non Final Office Action dated Apr. 9, 2012", 11 pgs.
"U.S. Appl. No. 12/064,529, Response filed Oct. 24, 2011 to Restriction Requirement dated Aug. 24, 2011", 9 pgs.
"U.S. Appl. No. 12/064,529, Restriction Requirement dated Aug. 24, 2011", 9 pgs.
"U.S. Appl. No. 12/302,738, Final Office Action dated Oct. 3, 2013", 11 pgs.
"U.S. Appl. No. 12/302,738, Non Final Office Action dated Jan. 2, 2013", 10 pgs.
"U.S. Appl. No. 12/302,738, Notice of Allowance dated Apr. 22, 2014", 7 pgs.
"U.S. Appl. No. 12/302,738, Notice of Allowance dated Dec. 27, 2013", Examiner Interview Summary, 9 pgs.
"U.S. Appl. No. 12/302,738, Preliminary Amendment filed Nov. 26, 2008", 8 pgs.
"U.S. Appl. No. 12/302,738, Response filed Jun. 26, 2013 to Non Final Office Action dated Jan. 2, 2013", 10 pgs.
"U.S. Appl. No. 12/302,738, Response filed Nov. 19, 2012 to Restriction Requirement dated Oct. 19, 2012", 7 pgs.
"U.S. Appl. No. 12/302,738, Response filed Dec. 3, 2013 to Final Office Action dated Oct. 3, 2013", 8 pgs.
"U.S. Appl. No. 12/302,738, Restriction Requirement dated Oct. 19, 2012", 7 pgs.
"U.S. Appl. No. 12/367,172, Final Office Action dated Jan. 18, 2012", 15 pgs.
"U.S. Appl. No. 12/367,172, Final Office Action dated Apr. 13, 2012", 21 pgs.
"U.S. Appl. No. 12/367,172, Final Office Action dated Apr. 21, 2015", 19 pgs.
"U.S. Appl. No. 12/367,172, Non Final Office Action dated May 27, 2011", 20 pgs.
"U.S. Appl. No. 12/367,172, Non Final Office Action dated Jul. 1, 2014", 20 pgs.
"U.S. Appl. No. 12/367,172, Response filed Mar. 8, 2011 to Restriction Requirement dated Dec. 8, 2010", 11 pgs.
"Application Serial No. 12/367,172, Response filed Aug. 13, 2012 to Final Office Action dated Apr. 13, 2012", 9 pgs.
"U.S. Appl. No. 12/367,172, Response filed Nov. 16, 2011 to Non Final Office Action dated May 27, 2011", 6 pgs.

(56) References Cited

OTHER PUBLICATIONS

"U.S. Appl. No. 12/367,172, Response filed Dec. 29, 2014 to Non Final Office Action dated Jul. 1, 2014", 7 pgs.
"Application Serial No. 12/367,172, Restriction Requirement dated Dec. 8, 2010", 6 pgs.
"U.S. Appl. No. 12/404,343, Advisory Action dated Apr. 5, 2013", 3 pgs.
"U.S. Appl. No. 12/704,343, Examiner Interview Summary dated Feb. 7, 2013", 3 pgs.
"U.S. Appl. No. 12/704,343, Examiner Interview Summary dated Feb. 25, 2013", 3 pgs.
"U.S. Appl. No. 12/704,343, Final Office Action dated May 10, 2013", 7 pgs.
"U.S. Appl. No. 12/704,343, Final Office Action dated Dec. 7, 2012", 9 pgs.
"U.S. Appl. No. 12/704,343, Non Final Office Action dated Jul. 16, 2012", 14 pgs.
"U.S. Appl. No. 12/704,343, Notice of Allowance dated Jan. 3, 2014", 11 pgs.
"U.S. Appl. No. 12/704,343, Notice of Allowance dated Aug. 2, 2013", 10 pgs.
"U.S. Appl. No. 12/704,343, Response filed Feb. 27, 2013 to Final Office Action dated Dec. 7, 2012", 9 pgs.
"U.S. Appl. No. 12/704,343, Response filed Jun. 5, 2012 to Restriction Requirement dated May 7, 2012", 7 pgs.
"U.S. Appl. No. 12/704,343, Response filed Jul. 10, 2013 to Final Office Action dated May 10, 2013", 8 pgs.
"U.S. Appl. No. 12/704,343, Response filed Oct. 16, 2012 to Non Final Office Action dated Jul. 16, 2012", 12 pgs.
"U.S. Appl. No. 12/704,343, Restriction Requirement dated May 7, 2012", 7 pgs.
"U.S. Appl. No. 13/682,208, Restriction Requirement dated Oct. 5, 2012", 10 pgs.
"U.S. Appl. No. 13/682,208, Advisory Action dated Oct. 30, 2015", 10 pgs.
"U.S. Appl. No. 13/682,208, Advisory Action dated Dec. 31, 2015", 8 pgs.
"U.S. Appl. No. 13/682,208, Examiner Interview Summary dated Sep. 11, 2014", 4 pgs.
"U.S. Appl. No. 13/682,208, Final Office Action dated May 23, 2014", 17 pgs.
"U.S. Appl. No. 13/682,208, Final Office Action dated Aug. 4, 2015", 19 pgs.
"U.S. Appl. No. 13/682,208, Non Final Office Action dated Nov. 5, 2014", 11 pgs.
"U.S. Appl. No. 13/682,208, Non Final Office Action dated Nov. 7, 2013", 13 pgs.
"U.S. Appl. No. 13/682,208, Notice of Allowance dated Jan. 29, 2016", 11 pgs.
"U.S. Appl. No. 13/682,208, Preliminary Amendment filed Nov. 20, 2012", 7 pgs.
"U.S. Appl. No. 13/682,208, PTO Response to Rule 312 Communication dated May 13, 2016", 2 pgs.
"U.S. Appl. No. 13/682,208, Response filed Jan. 4, 2016 to Advisory Action dated Dec. 31, 2015", 6 pgs.
"U.S. Appl. No. 13/682,208, Response filed Feb. 7, 2014 to Non Final Office Action dated Nov. 7, 2013", 9 pgs.
"U.S. Appl. No. 13/682,208, Response filed May 5, 2015 to Non Final Office Action dated Nov. 5, 2014", 9 pgs.
"U.S. Appl. No. 13/682,208, Response filed Aug. 7, 2013 to Restriction Requirement dated Jun. 6, 2013", 8 pgs.
"U.S. Appl. No. 13/682,208, Response filed Sep. 23, 2014 to Final Office Action dated May 23, 2014", 9 pgs.
"U.S. Appl. No. 13/682,208, Response filed Sep. 28, 2015 to Final Office Action dated Aug. 4, 2015", 10 pgs.
"U.S. Appl. No. 13/682,208, Response filed Nov. 25, 2015 to Advisory Action dated Oct. 30, 2015", 14 pgs.
"U.S. Appl. No. 13/682,208, Restriction Requirement dated Jun. 6, 2013", 9 pgs.
"U.S. Appl. No. 13/695,385, Final Office Action dated Oct. 28, 2014", 24 pgs.
"U.S. Appl. No. 13/695,385, Non Final Office Action dated Feb. 4, 2014", 20 pgs.
"U.S. Appl. No. 13/695,385, Response filed May 5, 2014 to Non Final Office Action dated Feb. 4, 2014", 8 pgs.
"U.S. Appl. No. 13/695,385, Response filed Sep. 24, 2013 to Restriction Requirement dated Aug. 2, 2013", 7 pgs.
"U.S. Appl. No. 13/695,385, Restriction Requirement dated Aug. 2, 2013", 7 pgs.
"U.S. Appl. No. 13/736,545, Notice of Allowance dated Mar. 18, 2014", 6 pgs.
"U.S. Appl. No. 13/791,175, Notice of Allowance dated Aug. 2, 2013", 9 pgs.
"U.S. Appl. No. 13/791,175, Preliminary Amendment filed Mar. 6, 2013", 3 pgs.
"U.S. Appl. No. 13/791,175, Examiner interview Summary dated Jun. 2, 2015", 2 pgs.
"U.S. Appl. No. 13/791,175, Final Office Action dated Nov. 20, 2014", 12 pgs.
"U.S. Appl. No. 13/791,175, Final Office Action dated Dec. 26, 2013", 12 pgs.
"U.S. Appl. No. 13/791,175, Non Final Office Action dated Jun. 7, 2013", 10 pgs.
"U.S. Appl. No. 13/791,175, Non Final Office Action dated Jul. 21, 2014", 11 pgs.
"U.S. Appl. No. 13/791,175, Preliminary Amendment, filed Mar. 8, 2013", 4 pgs.
"U.S. Appl. No. 13/791,175, Response filed Jun. 26, 2014 to Final Office Action dated Dec. 26, 2013", 9 pgs.
"U.S. Appl. No. 13/791,175, Response filed Oct. 21, 2014 to Non Final Office Action dated Jul. 21, 2014", 7 pgs.
"U.S. Appl. No. 13/791,175, Response filed Nov. 1, 2013 to Non Final Office Action dated Jun. 7, 2013", 8 pgs.
"U.S. Appl. No. 14/309,245, Notice of Allowance dated Jan. 20, 2015", 12 pgs.
"U.S. Appl. No. 14/912,043, Non Final Office Action dated Aug. 19, 2016", 12 pgs.
"U.S. Appl. No. 14/912,043, Preliminary Amendment, filed Feb. 17, 2016", 6 pgs.
"U.S. Appl. No. 15/565,097, Advisory Action dated Mar. 8, 2019", 3 pgs.
"U.S. Appl. No. 15/565,097, Final Office Action dated Jan. 8, 2019", 10 pgs.
"U.S. Appl. No. 15/565,097, Non Final Office Action dated Sep. 10, 2018", 9 pgs.
"U.S. Appl. No. 15/565,097, Non Final Office Action dated Sep. 13, 2019", 8 pgs.
"U.S. Appl. No. 15/565,097, Preliminary Amendment filed Oct. 11, 2017", 11 pgs.
"U.S. Appl. No. 15/565,097, Response filed Feb. 28, 2019 to Final Office Action dated Jan. 8, 2019", 11 pgs.
"U.S. Appl. No. 15/565,097, Response filed Apr. 8, 2019 to Advisory Action dated Mar. 8, 2019", 15 pgs.
"U.S. Appl. No. 15/565,097, Response filed May 11, 2018 to Restriction Requirement dated Apr. 20, 2018", 9 pgs.
"U.S. Appl. No. 15/565,097, Response filed Dec. 6, 2018 to Non Final Office Action dated Sep. 10, 2018", 12 pgs.
"U.S. Appl. No. 15/565,097, Restriction Requirement dated Apr. 20, 2018", 6 pgs.
"U.S. Appl. No. 16/495,083, Advisory Action dated Dec. 30, 2022", 3 pgs.
"U.S. Appl. No. 16/495,083, Final Office Action dated Sep. 19, 2022", 6 pgs.
"U.S. Appl. No. 16/495,083, Non Final Office Action dated Jun. 30, 2022", 7 pgs.
"U.S. Appl. No. 16/495,083, Response filed Jan. 19, 2023 to Advisory Action dated Dec. 30, 2022", 8 pgs.
"U.S. Appl. No. 16/495,083, Response filed May 31, 2022 to Restriction Requirement dated Apr. 1, 2022", 6 pgs.
"U.S. Appl. No. 16/495,083, Response filed Aug. 16, 2022 to Non Final Office Action dated Jun. 30, 2022", 7 pgs.

(56) References Cited

OTHER PUBLICATIONS

"U.S. Appl. No. 16/495,083, Response filed Dec. 8, 2022 to Final Office Action dated Sep. 19, 2022", 8 pgs.
"U.S. Appl. No. 16/495,083, Restriction Requirement dated Apr. 1, 2022", 4 pgs.
"U.S. Appl. No. 13/695,385, Preliminary Amendment filed Oct. 30, 2012", 7 pgs.
"Aromatic Ions (Chemgapedia)", [online]. [retrieved on Dec. 3, 2012]. Retrieved From Internet: <URL: http://www.chemgapedia.de/vsengine/vlu/vsc/en/ch/12/oc/vlu_organik/aromaten/aromaten/aromaten_gesamt.vlu/Page/vsc/en/ch/12/oc/aromaten/aromaten/ar_ionen/ar_ionen.vscml.html>, (2012), 2 pgs.
"Australia Application Serial No. 2008227128, First Examiner Report dated Jul. 6, 2012", 2 pgs.
"Australian Application Serial No. 2006283524, Office Action dated Mar. 27, 2008", 1 pg.
"Australian Application Serial No. 2006283524, Office Action dated Aug. 3, 2011", 4 pgs.
"Australian Application Serial No. 2006283524, Preliminary Amendment dated Mar. 3, 2008", 18 pgs.
"Australian Application Serial No. 2006283524, Response filed May 19, 2008 to Office Action dated Mar. 27, 2008", 10 pgs.
"Australian Application Serial No. 2006283524, Response filed Aug. 2, 2012 to Examiner Report dated Aug. 3, 2011", 34 pgs.
"Australian Application Serial No. 2007257423, Office Action dated Jun. 6, 2011", 2 pgs.
"Australian Application Serial No. 2007257423, Office Action dated Sep. 22, 2010", 4 pgs.
"Australian Application Serial No. 2007257423, Office Action dated Oct. 20, 2011", 2 pgs.
"Australian Application Serial No. 2007257423, Response filed May 31, 2011 to Office Action dated Sep. 22, 2010", 16 pgs.
"Australian Application Serial No. 2007257423, Response filed Sep. 13, 2011 to Office Action dated Jun. 6, 2011", 12 pgs.
"Australian Application Serial No. 2007257423, Response filed Dec. 19, 2011 to Office Action dated Oct. 20, 2011", 5 pgs.
"Australian Application Serial No. 2008227128, Preliminary Amendment filed Sep. 7, 2009", 45 pgs.
"Australian Application Serial No. 2008227128, Secondary Amendment filed Jan. 9, 2012", 16 pgs.
"Australian Application Serial No. 2009210655, Office Action dated Apr. 19, 2013", 3 pgs.
"Australian Application Serial No. 2009210655, Response filed Jul. 18, 2013 to First Examiner Report dated Apr. 19, 2013", 19 pgs.
"Australian Application Serial No. 2010214112 Response filed Feb. 27, 2015 to First Examiner Report dated May 23, 2014", 16 pgs.
"Australian Application Serial No. 2010214112, First Examiner Report dated May 23, 2014", 6 pgs.
"Bioassay Record NCI Yeast Anticancer Drug Screen", PUBCHEM, Data for the sgs1 mgt1 strain, PubChem AID 161, <https://pubchem.ncbi.nlm.nih.gov/bioassay/16>, (Aug. 15, 2004), 8 pgs.
"Brazil Application Serial No. PI1008383-9, Office Action dated Oct. 23, 2018", W/ English translation, 7 pgs.
"Brazilian Application Serial No. PI 0807196-9, Amendment filed Mar. 2, 2011", w/Engiish Claims, 19 pgs.
"Brazilian Application Serial No. PI 0807196-9, Office Action dated Jun. 11, 2019", w/ English Translation, 9 pgs.
"Brazilian Application Serial No. PI 0807196-9, Response filed Sep. 5, 2019 to Office Action dated Jun. 11, 2019", w/ English Claims, 26 pgs.
"Brazilian Application Serial No. PI0807196-9, Office Action dated Apr. 8, 2021", w/ English translation, 11 pgs.
"Brazilian Patent Application Serial No. P10907907, Amendment filed Dec. 27, 2011", w/ English Claims, 11 pgs.
"Canadian Application Serial No. 2,620,182, Office Action dated Aug. 24, 2012", 5 pgs.
"Canadian Application Serial No. 2,653,941, Office Action dated May 10, 2011", 3 pgs.
"Canadian Application Serial No. 2,653,941, Office Action dated Feb. 8, 2012", 2 pgs.
"Canadian Application Serial No. 2,653,941, Office Action dated Aug. 23, 2010", 5 pgs.
"Canadian Application Serial No. 2,653,941, Response filed Feb. 23, 2011 to Office Action dated Aug. 23, 2010", 20 pgs.
"Canadian Application Serial No. 2,653,941, Response filed Aug. 2, 2012 to Office Action dated Feb. 8, 2012", 7 pgs.
"Canadian Application Serial No. 2,653,941, Response filed Nov. 9, 2011 to Office Action dated May 10, 2011", 15 pgs.
"Canadian Application Serial No. 2,677,733 Response filed Feb. 16, 2015 to Office Action dated Aug. 2025, 14", 6 pgs.
"Canadian Application Serial No. 2,677,733, Office Action dated Jan. 6, 2016", 3 pgs.
"Canadian Application Serial No. 2,677,733, Office Action dated Aug. 25, 2014", 2 pgs.
"Canadian Application Serial No. 2,677,733, Voluntary Amendment filed Aug. 7, 2009", 45 pgs.
"Canadian Application Serial No. 2,713,438, Office Action dated Feb. 3, 2015", 5 pgs.
"Canadian Application Serial No. 2,752,074, Office Action dated Jan. 5, 2016", 5 pgs.
"Chinese Application Serial No. 200680038761.X, Office Action dated Mar. 22, 2012", (w/ English Translation), 9 pgs.
"Chinese Application Serial No. 200680038761.X, Office Action dated Apr. 14, 2010", with English translation, 9 pgs.
"Chinese Application Serial No. 200680038761.X, Office Action dated Jun. 23, 2011", (w/ English Translation), 9 pgs.
"Chinese Application Serial No. 200680038761.X, Response filed Sep. 7, 2011 to Office Action dated Jun. 23, 2011", (w/ English Translation of Amended Claims), 19 pgs.
"Chinese Application Serial No. 200680038761.X, Response filed Oct. 29, 2010 to Office Action dated Apr. 14, 2010", (w/ English Translation of Amended Claims), 22 pgs.
"Chinese Application Serial No. 200680038761.X, Response filed Jul. 6, 2012 to Action dated Mar. 22, 2012", (w/English Translation), 9 pgs.
"Chinese Application Serial No. 200880011525.8, Office Action dated Jan. 30, 2012", English Translation Only, 9 pgs.
"Chinese Application Serial No. 200880011525.8, Office Action dated Jul. 5, 2012", (w/ English Translation), 14 pgs.
"Chinese Application Serial No. 200880011525.8, Office Action dated Oct. 16, 2012", (w/ English Translation), 13 pgs.
"Chinese Application Serial No. 200880011525.8, Response filed Feb. 27, 2013 to Office Action dated Oct. 16, 2012", (w/ English Translation of Amended Claims), 10 pgs.
"Chinese Application Serial No. 200880011525.8, Response filed Jun. 13, 2012 to Office Action dated Jan. 30, 2012", (w/ English Translation of Claims), 14 pgs.
"Chinese Application Serial No. 200880011525.8, Response filed Sep. 20, 2012 to Office Action dated Jul. 5, 2012", (w/ English Translation of Claims), 12 pgs.
"Chinese Application Serial No. 200880011525.8, Voluntary Amendment filed Dec. 2, 2010", (w/English Translation of Claims), 12 pgs.
"Chinese Application Serial No. 200980112411.7, Office Action dated Nov. 5, 2012", (w/ English Translation), 15 pgs.
"Chinese Application Serial No. 200980112411.7, Office Action dated Nov. 5, 2012", (English Translation), 8 pgs.
"Chinese Application Serial No. 200980112411.7, Rejection Decision dated Jul. 23, 2013", (w/ English Translation), 14 pgs.
"Chinese Application Serial No. 200980112411.7, Response filed Mar. 19, 2013 to Office Action dated Nov. 5, 2012", (w/ English Translation), 4 pgs.
"Chinese Application Serial No. 200980112411.7, Response filed Aug. 15, 2012 to Office Action dated Feb. 2, 2012", (w/ English Translation of Amended Claims), 70 pgs.
"Chinese Application Serial No. 200980112411.7, Voluntary Amendment filed Jan. 31, 2011", (w/ English Translation of Claims), 74 pgs.
"Chinese Application Serial No. 201080016320.6, Office Action dated Mar. 20, 2014", w/English translation, 14 pgs.
"Chinese Application Serial No. 201080016320.6, Office Action dated Jun. 10, 2015", w/Engiish Translation, 10 pgs.
"Chinese Application Serial No. 201080016320.6, Office Action dated Jul. 8, 2013", (w/ English Translation), 16 pgs.

(56) References Cited

OTHER PUBLICATIONS

"Chinese Application Serial No. 201080016320.6, Office Action dated Oct. 21, 2014", W/ English Translation, 12 pgs.
"Chinese Application Serial No. 201080016320.6, Response filed Mar. 5, 2015 to Office Action dated Oct. 21, 2014", (w/ English Translation of Amended Claims), 10 pgs.
"Chinese Application Serial No. 201080016320.6, Response filed Aug. 4, 2014 to Office Action dated Mar. 20, 2014", w/ English translation, 7 pgs.
"Chinese Application Serial No. 201080016320.6, Response filed Nov. 25, 2013 to Office Action dated Jul. 8, 2013", (w/ English Translation of Claims), 12 pgs.
"Chinese Application Serial No. 201180033022.2 Response filed Jan. 6, 2015 to Non-Final Office Action dated Sep. 30, 2014", With the English claims, 7 pgs.
"Chinese Application Serial No. 201180033022.2, Office Action dated Jan. 13, 2014", w/English translation, 12 pgs.
"Chinese Application Serial No. 201180033022.2, Office Action dated Apr. 28, 2015", w/Engiish Translation, 14 pgs.
"Chinese Application Serial No. 201180033022.2, Office Action dated Aug. 22, 2014", w/English Translation, 18 pgs.
"Chinese Application Serial No. 201180033022.2, Response filed May 28, 2014 to Office Action dated Jan. 13, 2014", w/English claims, 9 pgs.
"Chinese Application Serial No. 201180033022.2, Voluntary Amendment filed Sep. 12, 2013", w/English translation, 13 pgs.
"Chinese Application Serial No. 200980112411.7, Office Action dated Feb. 2, 2012", w/ English Translation, 9 pgs.
"Definition: Micelle", Merriam-Webster, [Online]. Retrieved from the internet: <URL:http://www.merriam-webster.com/dictionary/micelle>, (Accessed on Jun. 25, 2014), 1 pg.
"Eurasian Application Serial No. 201001264, Office Action dated Sep. 12, 2012", (w/ English Summary), 2 pgs.
"Eurasian Application Serial No. 201101165, Office Action dated Dec. 12, 2012", (w/ English Translation), 7 pgs.
"Eurasian Application Serial No. 200901078—Pending Claims", 2 pgs.
"Eurasian Application Serial No. 200901078, Office Action dated Jan. 29, 2013", (w/ English Translation), 4 pgs.
"Eurasian Application Serial No. 200901078, Office Action dated Apr. 2, 2012", w/English Translation, 3 pgs.
"Eurasian Application Serial No. 200901078, Office Action dated May 26, 2011", (w/ English Translation), 5 pgs.
"Eurasian Application Serial No. 200901078, Office Action dated Sep. 18, 2012", (w/ English Translation), 4 pgs.
"Eurasian Application Serial No. 200901078, Office Action dated Sep. 21, 2011", (w/ English Translation), 4 pgs.
"Eurasian Application Serial No. 200901078, Response filed Jan. 16, 2013 to Office Action dated Sep. 18, 2012", (w/ English Translation of Claims), 68 pgs.
"Eurasian Application Serial No. 200901078, Response filed Jul. 29, 2013 to Office Action dated Jan. 29, 2013", (w/ English Translation of Claims), 138 pgs.
"Eurasian Application Serial No. 200901078, Response filed Sep. 13, 2011 to Office Action dated May 11, 2011", (w/ English Translation of Claims), 13 pgs.
"Eurasian Application Serial No. 201001264, Office Action dated Mar. 20, 2013", (w/ English Translation), 3 pgs.
"Eurasian Application Serial No. 201001264, Office Action dated Jul. 10, 2014", w/English Claims, 3 pgs.
"Eurasian Application Serial No. 201001264, Office Action dated Sep. 26, 2013", (w/ English Translation), 3 pgs.
"Eurasian Application Serial No. 201001264, Response filed Apr. 24, 2014 to Office Action dated Sep. 26, 2013", w/English claims, 4 pgs.
"Eurasian Application Serial No. 201001264, Response filed Jun. 5, 2013 to Office Action dated Mar. 20, 2013", (w/ English Translation of Amended Claims), 11 pgs.
"Eurasian Application Serial No. 201001264, Response filed Dec. 19, 2012 to Office Action dated Sep. 12, 2012", (w/ English Translation of Amended Claims), 16 pgs.
"Eurasian Application Serial No. 201101165, Office Action dated Jun. 28, 2013", (w/ English Translation), 3 pgs.
"Eurasian Application Serial No. 201101165, Response filed Apr. 9, 2013 to Office Action dated Dec. 12, 2012", (w/English Translation), 11 pgs.
"Eurasian Application Serial No. 201101165, Response filed Oct. 28, 2013 to Office Action dated Jun. 28, 2013", (w/ English Translation of Amended Claims), 10 pgs.
"Eurasian Patent Application Serial No. 200901078, Response filed Mar. 21, 2012 to Office Action dated Sep. 21, 2011", (w/ English Translation of Claims), 8 pgs.
"Eurasian Patent Application Serial No. 200901078, Response filed Aug. 2, 2012 to Office Action dated Apr. 2, 2012", (w/ English Translation of Claims), 4 pgs.
"European Application Serial No. 12004181.9, European Search Report dated Sep. 13, 2012", 8 pgs.
"European Application Serial No. 06813535.9, Examination Notification Art. 94(3) dated Sep. 24, 2013", 4 pgs.
"European Application Serial No. 06813535.9, Extended Search Report dated Oct. 24, 2011", 6 pgs.
"European Application Serial No. 06813535.9, Response filed Apr. 4, 2014 to Examination Notification Art. 94(3) dated Sep. 24, 2013", 70 pgs.
"European Application Serial No. 06813535.9, Response filed May 14, 2012 to Extended Search Report dated Oct. 24, 2011", 18 pgs.
"European Application Serial No. 06813535.9, Voluntary Amendment filed Apr. 22, 2008", 9 pgs.
"European Application Serial No. 07755916.9, Examination Notification Art. 94(3) dated Aug. 15, 2013", 4 pgs.
"European Application Serial No. 07755916.9, Office Action dated Mar. 25, 2014", 1 pg.
"European Application Serial No. 07755916.9, Office Action dated Nov. 11, 2011", 1 pg.
"European Application Serial No. 07755916.9, Response filed May 18, 2012 to Extended Search Report dated Oct. 25, 2011", 11 pgs.
"European Application Serial No. 07755916.9, Response filed May 23, 2014 to Examination Notification Art. 94(3) dated Aug. 15, 2013", 13 pgs.
"European Application Serial No. 07755916.9, Response filed May 23, 2014 to Office Action dated Mar. 25, 2014", 10 pgs.
"European Application Serial No. 07755916.9, Supplemental Search Report dated Oct. 25, 2011", 9 pgs.
"European Application Serial No. 08799591.6, Office Action dated May 21, 2012", 4 pgs.
"European Application Serial No. 08799591.6, Office Action dated Jun. 4, 2010", 4 pgs.
"European Application Serial No. 08799591.6, Response filed Sep. 20, 2012 to Office Action dated May 21, 2012", 31 pgs.
"European Application Serial No. 08799591.6, Response filed Nov. 22, 2011 to Office Action dated May 17, 2011", 26 pgs.
"European Application Serial No. 08799591.6, Response filed Dec. 2, 2010 to Office Action dated Jun. 4, 2010", 20 pgs.
"European Application Serial No. 09709019.5, Examination Notification Art. 94(3) dated Apr. 22, 2015", 6 pgs.
"European Application Serial No. 09709019.5, Examination Notification Art. 94(3) dated Oct. 9, 2013", 6 pgs.
"European Application Serial No. 09709019.5, Extended European Search Report dated Feb. 15, 2011", 8 pgs.
"European Application Serial No. 09709019.5, Extended European Search Report dated Feb. 15, 2011", 7 pgs.
"European Application Serial No. 09709019.5, Notification of Loss of Rights dated Oct. 21, 2011", 2 pgs.
"European Application Serial No. 09709019.5, Office Action dated Mar. 19, 2013", 5 pgs.
"European Application Serial No. 09709019.5, Response filed Sep. 25, 2013 to Examination Notification Art. 94(3) dated Mar. 19, 2013", 25 pgs.
"European Application Serial No. 09709019.5, Response filed Dec. 7, 2011 to Communication pursuant to 70(2) and 70a(2) EPC and the Notification of Loss of Rights dated Oct. 21, 2011", 41 pgs.

(56) References Cited

OTHER PUBLICATIONS

"European Application Serial No. 10706399.2, Communication pursuant to Rules 16(1) and 162 EPC dated Sep. 27, 2011", 2 pgs.
"European Application Serial No. 10706399.2, Examination Notification Art. 94(3) dated Jun. 11, 2015", 6 pgs.
"European Application Serial No. 10706399.2, Examination Notification dated Apr. 17, 2013", 4 pgs.
"European Application Serial No. 10706399.2, Examination Notification dated Oct. 2, 2012", 6 pgs.
"European Application Serial No. 10706399.2, Response filed Mar. 21, 2013 to Examination Notification dated Oct. 2, 2012", 11 pgs.
"European Application Serial No. 10706399.2, Response filed Aug. 13, 2013 to Examination Notification Art. 94(3) dated Apr. 17, 2013", 12 pgs.
"European Application Serial No. 11777689.8, Amendment filed Mar. 12, 2014", 11 pgs.
"European Application Serial No. 11777689.8, Communication pursuant to Rules 70(2) and 70a(2) EPC dated Nov. 6, 2013", 1 pg.
"European Application Serial No. 11777689.8, Examination Notification Art. 94(3) dated Oct. 8, 2014", 6 pgs.
"European Application Serial No. 11777689.8, Response filed Mar. 12, 2014 to Communication pursuant to Rules 70(2) and 70a(2) EPC dated Nov. 6, 2013", 11 pgs.
"European Application Serial No. 11777689.8, Supplementary European Search Report dated Oct. 18, 2013", 5 pgs.
"European Application Serial No. 12004181.9 Response Filed Dec. 15, 2014 to Non-Final Office Action dated Jul. 18, 2014", 138 pgs.
"European Application Serial No. 12004181.9, Communication dated Oct. 22, 2012", 2 pgs.
"European Application Serial No. 12004181.9, Communication pursuant to Rule 112(1) EPC dated May 31, 2013", 1 pg.
"European Application Serial No. 12004181.9, Examination Notification Art. 94(3) dated Jul. 18, 2014", 4 pgs.
"European Application Serial No. 12004181.9, Examination Notification Art. 94(3) dated Sep. 2, 2013", 5 pgs.
"European Application Serial No. 12004181.9, Response filed Mar. 7, 2014 to Examination Notification Art. 94(3) dated Sep. 2, 2013", 10 pgs.
"European Application Serial No. 12004181.9, Response filed Jul. 31, 2013 to Communication pursuant to Rule 112(1) EPC dated May 31, 2013 and Communication dated Oct. 22, 2012", 9 pgs.
"European Application Serial No. 13001458.2, Communication Pursuant to Article 94(3) EPC dated Mar. 22, 2016", 5 pgs.
"European Application Serial No. 13001458.2, Communication pursuant to Rules 70(2) and 70a(2) EPC dated Jul. 1, 2013", 1 pg.
"European Application Serial No. 13001458.2, Examination Notification Art. 94(3) dated Apr. 14, 2014", 5 pgs.
"European Application Serial No. 13001458.2, Extended European Search Report dated Apr. 22, 2013", 5 pgs.
"European Application Serial No. 13001458.2, Response filed Oct. 20, 2014 to Examination Notification Art. 94(3) dated Apr. 14, 2014", 28 pgs.
"European Application Serial No. 13001458.2, Response filed Dec. 16, 2013 to Communication pursuant to Rules 70(2) and 70a(2) EPC dated Jul. 1, 2013", 8 pgs.
"European Application Serial No. 13001957.3, Extended European Search Report dated Jan. 28, 2014", 17 pgs.
"European Application Serial No. 13001957.3, Office Action dated Mar. 3, 2014", 2 pgs.
"European Application Serial No. 13001957.3, Response filed Aug. 20, 2014 Extended European Search Report dated Jan. 28, 2014", Includes Response Office Action dated Mar. 3, 2014, 7 pgs.
"European Application Serial No. 20770127.7, Response to Communication pursuant to Rules 161(2) and 162 EPC filed Mar. 8, 2022", 22 pgs.
"European Application Serial No. 08799591.6, Examination Notification Art. 94(3) dated May 17, 2011", 5 pgs.
"I. Pharmaceutical Importance of Crystallin Hydrates", [online]. [retrieved on May 30, 2008]. Retrieved from the Internet: <URL: http://www.netlibrary.com/nlreader.dll?bookid=127838filename=Page_126.html>, (2008), 126-127.
"Indian Application Serial No. 10156/DELNP/2012, Amendment filed Dec. 26, 2012", 14 pgs.
"Indian Application Serial No. 10156/DELNP/2012, First Examination Report dated Oct. 25, 2017", (W/English Translation), 5 pgs.
"Indian Application Serial No. 2064/DELNP/2008, Examination Report dated Aug. 21, 2012", 5 pgs.
"Indian Application Serial No. 5675/DELNP/2009 Response filed Mar. 18, 2015 to First Examination Report dated Sep. 11, 2014", 6 pgs.
"Indian Application Serial No. 5675/DELNP/2009, First Examiner Report dated Sep. 11, 2014", 2 pgs.
"Indian Application Serial No. 5675/DELNP/2009, Voluntary Amendment filed Feb. 18, 2011", 7 pgs.
"Indian Application Serial No. 6293/DELNP/2010, First Examiner Report dated Dec. 22, 2016", 8 pgs.
"Indian Application Serial No. 6531-DELNP-2011, First Examiner Report dated Jun. 23, 2017", 7 pgs.
"Indian Application Serial No. 6531-DELNP-2011, Response filed Feb. 6, 2020 to Hearing of Jan. 28, 2020", 34 pgs.
"Indian Application Serial No. 6531-DELNP-2011, Response Filed Sep. 8, 2017 to First Examiner Report dated Jun. 23, 2017", (W/English Claims), 19 pgs.
"International Application Serial No. PCT/US06/32371, International Preliminary Report on Patentability dated Mar. 6, 2008", 6 pgs.
"International Application Serial No. PCT/US06/32371, International Search Report dated Jul. 23, 2007", 3 pgs.
"International Application Serial No. PCT/US06/32371, Written Opinion dated Jul. 23, 2007", 6 pgs.
"International Application Serial No. PCT/US2007/009840, International Preliminary Report on Patentability dated Dec. 18, 08", 9 pgs.
"International Application Serial No. PCT/US2007/009840, International Search Report dated Aug. 5, 2008", 4 pgs.
"International Application Serial No. PCT/US2007/009840, Written Opinion dated Aug. 5, 2008", 7 pgs.
"International Application Serial No. PCT/US2008/001631, International Preliminary Examination Report dated Aug. 20, 2009", 12 pgs.
"International Application Serial No. PCT/US2008/001631, International Search Report dated Jan. 21, 2009", 6 pgs.
"International Application Serial No. PCT/US2008/001631, Written Opinion dated Jan. 21, 2009", 9 pgs.
"International Application Serial No. PCT/US2009/000771, International Preliminary Report on Patentability dated Aug. 19, 2010", 8 pgs.
"International Application Serial No. PCT/US2009/000771, International Search Report dated Aug. 28, 2009", 4 pgs.
"International Application Serial No. PCT/US2009/000771, Written Opinion dated Aug. 28, 2009", 5 pgs.
"International Application Serial No. PCT/US2009/006584, International Preliminary Report on Patentability dated Jun. 30, 2011", 8 pgs.
"International Application Serial No. PCT/US2009/006584, Search Report dated Sep. 8, 2010", 5 pgs.
"International Application Serial No. PCT/US2009/006584, Written Opinion dated Sep. 8, 2010", 6 pgs.
"International Application Serial No. PCT/US2010/000369, International Preliminary Report on Patentability dated Jun. 28, 2011", 13 pgs.
"International Application Serial No. PCT/US2010/000369, International Search Report dated Sep. 21, 2010", 6 pgs.
"International Application Serial No. PCT/US2010/000369, Partial International Search Report dated Jul. 5, 2010", 6 pgs.
"International Application Serial No. PCT/US2010/000369, Response filed Dec. 21, 2010 to Written Opinion dated Sep. 21, 2010", 8 pgs.
"International Application Serial No. PCT/US2010/000369, Written Opinion dated Feb. 11, 2010", 9 pgs.
"International Application Serial No. PCT/US2010/000369, Written Opinion dated Sep. 21, 2010", 9 pgs.

(56) References Cited

OTHER PUBLICATIONS

"International Application Serial No. PCT/US2011/000757, International Preliminary Report on Patentability, dated Nov. 15, 2012", 7 pgs.
"International Application Serial No. PCT/US2011/000757, International Search Report dated Dec. 21, 2011", 5 pgs.
"International Application Serial No. PCT/US2011/000757, Written Opinion dated Dec. 21, 2011", 6 pgs.
"International Application Serial No. PCT/US2014/051090, International Preliminary Report on Patentability dated Feb. 25, 2016", 6 pgs.
"International Application Serial No. PCT/US2014/051090, International Search Report dated Nov. 14, 2014", 4 pgs.
"International Application Serial No. PCT/US2014/051090, Written Opinion dated Nov. 14, 2014", 4 pgs.
"International Application Serial No. PCT/US2016/026522, International Preliminary Report on Patentability dated Oct. 19, 2017", 9 pgs.
"International Application Serial No. PCT/US2016/026522, International Search Report dated Jun. 20, 2016", 5 pgs.
"International Application Serial No. PCT/US2016/026522, Written Opinion dated Jun. 20, 2016", 7 pgs.
"International Application Serial No. PCT/US2018/025522, International Preliminary Report on Patentability dated Oct. 10, 2019", 8 pgs.
"International Application Serial No. PCT/US2018/025522, International Search Report dated Jun. 18, 2018", 3 pgs.
"International Application Serial No. PCT/US2018/025522, Written Opinion dated Jun. 18, 2018", 6 pgs.
"International Application Serial No. PCT/US2019/056284, International Preliminary Report on Patentability dated May 6, 2021", 9 pgs.
"International Application Serial No. PCT/US2019/057496, International Search Report dated Feb. 27, 2020", 4 pgs.
"International Application Serial No. PCT/US2019/057496, Invitation to Pay Add'l Fees and Partial Search Report, dated Jan. 9, 2020", 2 pgs.
"International Application Serial No. PCT/US2019/057496, Written Opinion dated Feb. 27, 2020", 7 pgs.
"International Application Serial No. PCT/US2020/022786, International Preliminary Report on Patentability dated Sep. 23, 2021", 7 pgs.
"International Application Serial No. PCT/US2020/022786, International Search Report dated Jun. 16, 2020", 3 pgs.
"International Application Serial No. PCT/US2020/022786, Written Opinion dated Jun. 16, 2020", 5 pgs.
"International Application Serial No. PCT/US2020/046568, International Preliminary Report on Patentability dated Mar. 3, 2022", 8 pgs.
"International Application Serial No. PCT/US2020/046568, International Search Report dated Jan. 12, 2021", 4 pgs.
"International Application Serial No. PCT/US2020/046568, Invitation to Pay Additional Fees and Partial Search Report dated Oct. 27, 2020", 2 pgs.
"International Application Serial No. PCT/US2020/046568, Written Opinion dated Jan. 12, 2021", 6 pgs.
"International Application Serial No. PCT/US2021/053648, International Search Report dated Mar. 9, 2022", 5 pgs.
"International Application Serial No. PCT/US2021/053648, Invitation to Pay Additional Fees dated Dec. 9, 2021", 3 pgs.
"International Application Serial No. PCT/US2021/053648, Written Opinion dated Mar. 9, 2022", 5 pgs.
"Isolation/Modification/Labeling Product Sheet", Interchim Inc, (Jan. 15, 2000), 1-23.
"Israel Application Serial No. 207246, Office Action dated May 27, 2014", 2 pgs.
"Israel Application Serial No. 207246, Office Action dated Feb. 10, 2013", (English Translation), 2 pgs.
"Israel Application Serial No. 207246, Response filed Jun. 10, 2013 to Office Action dated Feb. 10, 2013", (w/English Translation of Claims), 7 pgs.
"Israeli Application Serial No. 200240, Examiner Report dated Aug. 5, 2013", (English Translation), 3 pgs.
"Israeli Application Serial No. 200240, Examiner Report dated Aug. 28, 2012", (English Translation), 4 pgs.
"Israeli Application Serial No. 200240, Response filed Nov. 25, 2013 to Examiner Report dated Aug. 5, 2013", w/English translation, 8 pgs.
"Israeli Application Serial No. 200240, Response filed Dec. 17, 2012", 5 pgs.
"Israeli Application Serial No. 200240, Response filed Dec. 17, 2012 to Examiner Report dated Aug. 28, 2012", (w/ English Translation of Claims), 4 pgs.
"Israeli Application Serial No. 207246, Office Action dated Jun. 29, 2015", 3 pgs.
"Israeli Application Serial No. 214572, Office Action dated Jan. 2, 2014", (English Translation), 2 pgs.
"Israeli Application Serial No. 214572, Office Action dated Feb. 7, 2014", 2 pgs.
"Israeli Application Serial No. 214572, Office Action dated Jul. 9, 2013", (English Translation), 3 pgs.
"Israeli Application Serial No. 214572, Office Action dated Nov. 13, 2012", EN Office Action only, 2 pgs.
"Israeli Application Serial No. 214572, Response filed Apr. 28, 2014 to Office Action dated Jan. 2, 2014", English claims, 10 pgs.
"Israeli Application Serial No. 214572, Response filed Nov. 3, 2013 to Office Action dated Jul. 9, 2013", (English Translation of Claims), 5 pgs.
"Israeli Application Serial No. 214572, Response filed Dec. 30, 2014 to Office Action dated Jul. 3, 2014", 4 pgs.
"Israeli Application Serial No. 214572, Response filed Dec. 30, 2014 to Office Action dated Jul. 9, 2013", English claims only, 4 pgs.
"Japanese Application Serial No. 2008-528017, Office Action dated May 22, 2012", (w/ English Transation), 7 pgs.
"Japanese Application Serial No. 2008-528017, Preliminary Amendment filed Aug. 12, 2009", w/English Claims, 26 pgs.
"Japanese Application Serial No. 2008-528017, Response filed Nov. 20, 2012 to Office Action dated May 22, 2012", (w/ English Translation of Amended Claims), 19 pgs.
"Japanese Application Serial No. 2009-549102, Office Action dated May 29, 2013", (w/ English Translation), 5 pgs.
"Japanese Application Serial No. 2009-549102, Office Action dated Oct. 16, 2012", (w/ English Translation), 10 pgs.
"Japanese Application Serial No. 2009-549102, Response filed Mar. 22, 2013 to Office Action dated Oct. 16, 2012", (w/ English Translation of Amended Claims), 7 pgs.
"Japanese Application Serial No. 2009-549102, Response filed Aug. 20, 2013 to Office Action dated May 29, 2013", (w/ English Translation of Amended Claims), 5 pgs.
"Japanese Application Serial No. 2009-549102, Voluntary Amendment filed Feb. 7, 2011", (w/ English Translation of Amended Claims), 24 pgs.
"Japanese Application Serial No. 2010-545884, Amendment filed Jan. 23, 2012", (English Translation), 7 pgs.
"Japanese Application Serial No. 2010-545884, Examiners Decision of Final Refusal dated Aug. 20, 2014", 6 pgs.
"Japanese Application Serial No. 2010-545884, Office Action dated Oct. 9, 2013", (w/ English Translation), 5 pgs.
"Japanese Application Serial No. 2010-545884, Response filed Apr. 8, 2014 to Office Action dated Oct. 9, 2013", w/English claims, 49 pgs.
"Japanese Application Serial No. 2010-545884, Voluntary Amendment filed Oct. 7, 2010", (w/ English Translation), 65 pgs.
"Japanese Application Serial No. 2011-549168, Amendment Filed Dec. 27, 2012", (English Translation of Claims), 6 pgs.
"Japanese Application Serial No. 2011-549168, Office Action dated Apr. 17, 2015", w/English translation, 5 pgs.
"Japanese Application Serial No. 2011-549168, Office Action dated Jun. 2, 2014", w/English translation, 13 pgs.

(56) References Cited

OTHER PUBLICATIONS

"Japanese Application Serial No. 2011-549168,Response filed Dec. 1, 2014 to Office Action dated Jun. 2, 2014", W/ English Translation, 19 pgs.
"Japanese Application Serial No. 2011-549168,Response filed Dec. 1, 2014 to Office Action dated Jun. 2, 2014", w/ English Translation of Amended Claims), 19 pgs.
"Japanese Application Serial No. 2013-507951, Office Action dated Mar. 6, 2015", 4 pgs.
"Japanese Application Serial No. 2013-507951, Voluntary Amendment filed Mar. 19, 2014", 13 pgs.
"Japanese Application Serial No. 2013-59721, Office Action dated May 30, 2014", w/English translation, 10 pgs.
"Japanese Application Serial No. 2014-79326, Office Action dated Mar. 31, 2015", 2 pgs.
"Japanese Patent Application Serial No. 2008-528017, Office Action dated May 22, 2012", (English Translation), 4 pgs.
"Korean Application Serial No. 10-2009-7018499, Office Action dated Sep. 17, 2014", 8 pgs.
"Korean Application Serial No. 10-2011-7021190, Office Action dated Aug. 18, 2016", 11 pgs.
"Korean Application Serial No. 10-2010-7019944, Amendment filed Jan. 10, 2014", w/English claims, 31 pgs.
"Mexican Application Serial No. MX/a/2010/008697 , Response filed Mar. 28, 2012 to Office Action dated Nov. 28, 2011", (w/English Translation of Claims), 22 pgs.
"Mexican Application Serial No. MX/a/2010/008697, Office Action dated Nov. 28, 2011", (w/ English Translation), 7 pgs.
"Mexican Application Serial No. MX/a/2010/008697, Response filed Jul. 10, 2012 to Office Action dated May 4, 2012", (w/ English Translation of Claims), 6 pgs.
"Mexican Application Serial No. MX/a/2010/8697, Office Action dated May 10, 2012", (English Translation), 3 pgs.
"Mexican Application Serial No. MX/a/2011/008500, Office Action dated Jun. 14, 2013", (English Translation), 1 pg.
"Mexican Application Serial No. MX/a/2011/008500, Response filed Oct. 24, 2013 to Office Action dated Jun. 14, 2013", (w/ English Translation of Claims), 17 pgs.
"Modulation of cytokine production and enhancement of cell viability byTLR7 and TLR9 ligands during anthrax infection of macrophages", FEMS Immunol. Med. Microbiol., 2006, vol. 47, No. 3, 369-379.
"PubChem CID 100446926", [Online] Retrieved from the Internet: <URL: https://pubchem.ncbi.nlm.nih.gov/compound/100446926>, [Accessed Dec. 8, 2020], (Dec. 11, 2015), 7 pgs.
"PubChem-CID-4371238", (Sep. 14, 2005), 11 pages.
"Singapore Application Serial No. 201005638-0, Response filed Aug. 22, 2012 to Office Action dated Jun. 27, 2012", 2 pgs.
"Singapore Application Serial No. 201005638-0, Examination Report dated Dec. 6, 2012", (English Translation), 6 pgs.
"Singapore Application Serial No. 201005638-0, Office Action dated Jun. 27, 2012", 7 pgs.
"Singapore Application Serial No. 201005638-0, Office Action dated Nov. 9, 2011", 16 pgs.
"Singapore Application Serial No. 201005638-0, Search Report dated Oct. 27, 2011", 7 pgs.
"Singapore Application Serial No. 201005638-0, Written Opinion dated Oct. 27, 2011", 8 pgs.
"Singapore Application Serial No. 201005638-0, Office Action Response filed Mar. 29, 2012 to Office Action dated Nov. 9, 2011", (English Translation), 91 pgs.
"Substance Record for SID 384153951", PubChem, <https://pubchem.ncbi.nlm.nih.gov/6Ubstance/384153951>, (May 15, 2019), 5 pgs.
"Substance Record for SID 458963136", PubChem, <https://pubchem.ncbi.nlm.nih.gov/substance/458963136>, (Dec. 15, 2021), 6 pgs.
"Synthesis and Immunological Characterization of Tull-Like Receptor 7 Agonistic Conjugates", Bioconjug. Chem., 2009, vol. 20, No. 6, 1194-1200.
"Turkey Application Serial No. 120041819, Office Action dated Apr. 29, 2016", w/ English translation, 6 pgs.

Admyre, et al., "", Europ. J of Immunology, v.36, (2006), 1772-1781.
Anders, H.-J., et al., "Molecular mechanisms of autoimmunity triggered by microbial infection", Arthritis Research & Therapy, 7(5), (2005), 215-224.
Ang, W. H, et al., "Organometallic ruthenium inhibitors of glutathione-S-transferase P1-1 as anticancer drugs.", ChemMedChem, 2(12), (Dec. 2007), 1799-806.
Baenziger, S., et al., "Triggering TLR7 in mice induces immune activation and lymphoid system disruption, resembling HIV-mediated pathology", Blood, 113(2), (Jan. 8, 2009), 377-388.
Bhunia, Debabrata, et al., "Design, Synthesis, and Evaluation of Novel 1,2,3-Triazole-Tethered Glycolipids as Vaccine Adjuvants", Arch. Pharm. Chem. Life Sci. vol. 348, (2015), 15 pages.
Brown, Gordon, "Dectin-1: a signalling non-TLR pattern-recognition receptor", Nature Reviews Immunology, (2006), 33-43.
Bryan, G. T., et al., "Interferon (IFN) and IFN Inducers Protect Mouse Bladder Urothelium Against Carcinogenicity by FANFT", Journal of Cancer Research and Clinical Oncology, 116(Suppl. Part 1), (Abstract A3.106.36), (15th International Cancer Congress, Hamburg, Aug. 16-22, 1990), (1990), p. 308.
Butler, Roslyn S, et al., "Highly fluorescent donor acceptor purines", J. Mater. Chem, 17(19), (2007), 1863-1865.
Carson, D. A., et al., "TLR Agonists", U.S. Appl. No. 60/710,337, Application filed Aug. 22, 2005, 52 pgs.
Chan, et al., "Structure-Activity Relationship Studies to Identity Affinity Probes in Bis-aryl Sulfonamides That Prolong Immune Stimuli", Journal of Medicinal Chemistry vol. 62, (Oct. 11, 2019), 9521-9540.
Chan, M., et al., "Identification of Substituted Pyrimido[5,4-b]indoles as Selective Toll-Like Receptor 4 Ligands", J. Med. Chem., 56, (2013), 4206-4223.
Chan, M., et al., "Synthesis and Characterization of PEGylated Toll Like Receptor 7 Ligands", Bioconjugate Chem., 22, (2011), 445-454.
Chan, Michael, et al., "Identification of Biologically Active Pyrimido[5,4-b]indoles That Prolong NF-kappa-B Activation without Intrinsic Activity", ACS Comb Sci. vol. 19(8), (2017), 26 pages.
Chan, Michael, et al., "Synthesis and Immunological Characterization of Toll-Lke Receptor 7 Agonistic Conjugates", Bioconjugate Chem., 20(6), (2009), 1194-1200.
Colombo, R., et al., "Combination of intravesical chemotherapy and hyperthermia for the treatment of superficial bladder cancer: preliminary clinical experience", Crit Rev Oncol Hematol., 47(2), (Aug. 2003), 127-39.
Dolan, M. E, et al., "Metabolism of O6-benzylguanine, an inactivator of O6-alkylguanine-DNA alkyltransferase.", Cancer Res., 54(19), (Oct. 1, 1994), 5123-30.
Fox, et al., "A nanoliposome delivery system to synergistically trigger TLR4 and TLR7", Journal of Nanobiotechnology vol. 12, (Apr. 26, 2014), 1-9.
Goff, P.H., et al., "Synthetic Toll-Like Receptor 4 (TLR4) and TLR7 Ligands and Influenza Virus Vaccine Adjuvants Induce Rapid, Sustained, and Broadly Protective Responses", Journal of Virology, 89, (Mar. 2015), 3221-3235.
Greenwald, R B, et al., "Poly(Ethylene Glycol) Conjugated Drugs and Prodrugs: A Comprehensive review", Critical reviews in therapeutic drug carrier systems vol. 17, No. 2, (Jan. 1, 2000), 101-161.
Hayashi, T., et al., "Mast cell-dependent anorexia and hypothermia induced by mucosal activation of Toll-like receptor 7", Am J Physiol Regul Integr Comp Physiol., 295(1), (2008), R123-32.
Hayashi, T., et al., "Novel Synthetic Toll-Like Receptor 4/MD2 Ligands Attenuate Sterile Inflammation", J. Pharmacol.Exp. Ther., 350, (Aug. 2014), 330-340.
Horner, et al., "Optimized conjugation ratios lead to allergen immunostimulatory oligodeoxynucieotide conjugates with retained Immunogenicity and minimal anaphylactogenicity", J Allergy Clin Immunol 110, (2002), 413-42 0.
Jacobson, Kenneth A, et al., "Adenosine analogs with covalently attached lipids have enhanced potency at AI-adenosine receptors", FEBS Letters, 225(1-2), (1987), 97-102.

(56) References Cited

OTHER PUBLICATIONS

Jin, G., et al., "Synthesis and immunostimulatory activity of 8-substltuted amino 9-benzyladenlnes as potent Toll-like receptor 7 agonists.", Bioorg Med Chem Lett., 16(17), (Sep. 1, 2006), 4559-4563.

Johnson, John W, et al., "Binding of Liposomes to Human Bladder Tumor Epithelial Cell Lines: Implications for an Intravesical Drug Delivery System for the Treatment of Bladder Cancer", Selective Cancer Therapeutics vol. 5, No. 4,1989, [Online]. Retrieved from the Internet: <http://online.liebertpub.com/doi/pdf/10.1089/sct.1989.5.147>, (1989), 9 pgs.

Julien, R. M., "Chapter 2: Pharmacodynamics: How Drugs Act", A Primer of Drug Action (Ninth Edition); Worth Publishers, (2001), 37-57.

Kaeppler, U., et al., "A new lead for nonpeptidic active-site-directed inhibitors of the severe acute respiratory syndrome coronavirus main protease discovered by a combination of screening and docking methods.", J Med Chem., 48(22), (Nov. 3, 2005), 6832-42.

Kobayashi, H., et al., "Prepriming: a novel approach to DNA-based vaccination and immunomodulation", Springer Seminars in Immunopathology, 22(Nos. 1-2), (2000), 85-96.

Krawitt, "Autoimmune hepatitis", N Engl J Med. Jan. 5, 2006;354(1):, (2006), 54-66.

Kulikov, V. I, et al., "Lipid derivatives of prostaglandins and nonsteroidal antiinflammatory drugs (a review)", Pharmaceutical Chemistry Journal, 31(4), (1997), 173-177.

Kurimoto, A., et al., "Prodrugs of 9-benzyl-8-hydroxy-2-(2-hydroxyethylthio)adenine: potent interferon inducing agents in monkeys", Chem. Pharm. Bull. 52(4), Retrieved from the internet: <URL: https://www.jstage.jst.go.jp/article/cpb/52/4/52_4_466/_pdf/-char/ja>, (2004), 466-469.

Kurimoto, A., et al., "Synthesis and evaluation of 2-substituted 8-hydroxyadenines as potent interferon inducers with improved oral bioavailabilities", Bioorg Med Chem., 12(5), (Mar. 1, 2004), 1091-1099.

Kurimoto, A., et al., "Synthesis and structure-activity relationships of 2-amlno-8-hydroxyadenines as orally active interferon inducing agents", Bioorg Med Chem., 11(24), (Dec. 1, 2003), 5501-8.

Lee, J., et al., "Molecular basis for the immunostimulatory activity of guanine nucleoside analogs: Activation of Toll-like receptor 7", Proc. Natl. Acad. Sci., 100(11), (2003), 6646-6651.

Lippard, Stephen J, "The Art of chemistry", Nature, 416, (2002), 587.

Liu, H., et al., "Tumour growth inhibition by an imidazoquinoline is associated with c-Myc down-regulation in urothelial cell carcinoma", BJU international, 101(7), (Apr. 2008), 894-901.

Maeda, D. Y, et al., "Bivalent inhibitors of glutathione S-transferase: the effect of spacer length on isozyme selectivity.", Bioorg Med Chem Lett.,16(14), (Jul. 15, 2006), 3780-3.

Mahajan, S. S, et al.. "Optimization of bivalent glutathione S-transferase inhibitors by combinatorial linker design.", J Am Chem Soc., 128(26), (Jul. 5, 2006), 8615-25.

Mayer, R., et al., "A randomized controlled trial of intravesical bacillus calmette-guerin for treatment refractory interstitial cystitis", Journal of Urology, 173(4), (Apr. 2005), 1186-1191.

Metzler, David E, "Biosynthesis of triglycerides and phospholipids", Biochemistry: The Chemical Reactions of Living Cells, (1977), 708.

Miller, R L, et al., "Imiquimod applied topically: a novel immune response modifier and new class of drug", int J Immunopharmacol., 21(1), (Jan. 1999), 1-14.

Moroishi, et al., "The Hippo Pathway Kinases LATS1/2 Suppress Cancer Immunity' Cell", vol. 167, No. 6, (Dec. 1, 2016), 1525-1539.

Mosmann, T. R., et ai., "TH1 and TH2 cells: different patterns of lymphokine secretion lead to different functional properties", Annual Review Immunology, 7, (1989), 145-173.

Rafi, et al., "", BioImpact, v.5, (2015), 117-122.

Roh YS, Seki E, "Toll-like receptors in alcoholic liver disease, non-alcoholic steatohepatitis and carcinogenesis", J Gastroenterol Hepatol Suppl 1, (2013), 38-42.

Rohn, S., et al., "Antioxidant activity of protein-bound quercetin", J Agric Food Chem., 52(15), (Jul. 28, 2004), 4725-9.

Schon, M., et al., "Tumor-Selective Induction of Apoptosis and the Small-Molecule Immune Response Modifier imiquimod", J Natl Cancer Inst, 95(15), (2003), 1138-1149.

Shi, B, et al., "Discovery of glutathione S-transferase inhibitors using dynamic combinatorial chemistry.", J Am Chem Soc., 128(26), (Jul. 5, 2006), 8459-67.

Sidky, Y. A., et al., "Curative effectiveness of the interferon inducing imiquimod as a signal agent in mouse bladder tumors", Proceedings, Eighty-Fourth Meeting of the American Association for Cancer Research, vol. 34, (Abstract 2789) (May 19-22, 1993, Orlando, FL), (Mar. 1993), 467.

Sidky, Y. A, et al., "Effects of Treatment with an Oral Interferon Inducer, Imidazoquinolinamine (R-837), on the Growth of Mouse Bladder Carcinoma FCB", Journal of Interferon Research, 10(Supp 1), (Abstract II6-12) (Annual Meeting of the ISIR, San Francisco, CA, Nov. 14-18, 1990), (Nov. 1990), S123.

Sidky, Y. A., et al., "Effects of treatment with the oral interferon inducer, R-837, on the growth of mouse colon carcinoma, MC-26", Proceedings, 81st Annual Meeting of the American Association for Cancer Research, vol. 31, (Abstract 2574), (Mar. 1990), p. 433.

Sidky, Y. A, et al., "Inhibition of murine tumor growth by an interferon-inducing imidazoquinolinamine", Cancer Research, 52(13), (Jul. 1, 1992), 3528-33.

Sidky, Y. A., et al., "Inhibition of tumor-induced angiogenesis by the interferon inducer imiquimod", Proceedings, Eighty-Third Annual Meeting of the American Association of Cancer Research, vol. 33, (Abstract 458) (May 20-23, 1992, San Diego, CA), (Mar. 1992), p. 77.

Simons, M. P., et al., "Identification of the Mycobacterial Subcomponents Involved in the Release of Tumor Necrosis Factor-Related Apoptosis-Inducing Ligand from Human Neutrophils", Infection and Immunity, 75(3), (2007), 1265-1271.

Smith, E. B, et al., "Effects of Imiquimod, a toli-like receptor-7 agonist, on cell proliferation and cytokine production in bladder cancer in vitro and in vivo", Journal of Urology, 173(4, Suppl. S), (Apr. 2005), 158.

Smith, Eric B., et al., "Antitumor Effects of Imidazoquinolines in Urothelial Cell Carcinoma of the Bladder", The Journal of Urology, 177(6), (Jun. 2007), 2347-2351.

Spohn, R., et al., "Synthetic lipopeptide adjuvants and Toli-like receptor 2-structure-activity relationships", Vaccine, 22(19), (Jun. 23, 2004), 2494-9.

Staros, E. B., et al., "New Approaches to Understanding Its Clinical Significance", Am. J. Clin. Pathol., 123(2), (2005), 305-312.

Takeda, K., et al., "Toll-like receptors", Annu Rev Immunol., 21, (2003), 335-76.

Takeda, K., et al., "Toll-like receptors in innate immunity", International Immunology, 17(1), (2005), 1-14.

Tyagi, P., et al., "Local drug delivery to bladder using technology innovations", Urol Clin North Am., 33(4), (Nov. 2006), 519-530.

Veronese, F. M et al., "The impact of PEGylation on biological therapies", BioDrugs, 22(5), (2008), 315-329.

Wille-Reece, U., et al., "HIV Gag protein conjugated to a Toll-like receptor 7/8 agonist improves the magnitude and quality of Th1 and CD8+ T cell responses in nonhuman primates", Proc. Natl. Acad. Sci. USA, 102(42), (Oct. 18, 2005), 15190-15194.

Wu, Christina C. N., et al., "Immunotherapeutic activity of a conjugate of a Toll-like receptor 7 ligand", Proc Natl Acad Sci USA, 104(10), (Mar. 6, 2007), 3990-3995.

Yang, Victor C., et al., "Bioconjugates for Effective Drug Targeting", Advanced Drug Delivery Reviews 55 (2003), (2002), 169-170.

Yoo, Euna, "Exploration of Toli-like Receptor 7 and 8 Agonists as Potential Vaccine Adjuvants", PhD Diss., University of Kansas, [Online] Retrieved from the Internet: <URL: https://kuscholarworks.ku.edu/handle/1808/23923?show=full>, (May 7, 2017), 281 pgs.

Zaks, K, et al., "Efficient Immunization and Cross-Priming by Vaccine Adjuvants Containing TLR3 or TLR9 Agonist Complexed to Cationic Liposomes". Journal of Immunology, 176(12), (Jun. 15, 2006), 7335-7345.

(56) References Cited

OTHER PUBLICATIONS

Zaks, Karen, et al., "Efficient immunization and cross-priming by vaccine adjuvants containing TLR3 or TLR9 agonists complexed to cationic liposomes", J Immunol., 176(12), (Jun. 15, 2006), 7335-45.

* cited by examiner

EARLY OVARIAN CANCER DETECTION DIAGNOSTIC TEST BASED ON MRNA ISOFORMS

CROSS-REFERENCE TO RELATED APPLICATIONS

This application claims the benefit of the filing date of U.S. application Ser. No. 62/340,876, filed on May 24, 2016, the disclosure of which is incorporated by reference herein.

BACKGROUND

Identifying molecules that are specific to tumors for use in early detection, diagnosis, prognosis, and therapeutic strategy design is both a primary goal and a key discovery challenge across diverse areas of oncology. Furthermore, the extent of inter- and intra-tumor heterogeneity indicates that multiple tumor-specific molecules will be needed for any of these applications (Farhangfar et al., 2013; Swanton, 2012; Marusyk et al., 2012). Although DNA alterations constitute the major focus of tumor specific discovery efforts to date, in many respects mRNA is more attractive for this purpose. This is because RNA can: 1) broadly reflect (malignant) cellular phenotypes; 2) exist in thousands of copies per cell and thereby enable highly sensitive early detection and diagnostic assays; and 3) can sensitively and comprehensively reveal potential candidate antigens for monoclonal antibody targeting, vaccines, and adoptive immunotherapies (Adamia et al., 2013; Lupetti et al., 1998; Rousseaux et al., 2013). The efficacy of using mRNA for these purposes is highly dependent on the degree of tumor-specific expression.

One of the main themes of microarray-based experiments that have been undertaken during the last decade has been the discovery of tumor-specific "genes". Aside from the class of cancer-germline (aka cancer/testis) genes (Coulie et al., 2014), few have been found. In retrospect, the "gene" concept critically hindered these efforts to discover tumor-specific expression because the word "gene" is a collective term for all mRNA isoforms expressed from a genomic locus. Malignant and normal tissue types can be distinguished by patterns of differential isoform usage (David et al., 2010; Venables et al., 2009), but when measured in aggregate at the "gene" level the isoform-specific differences are at best recognized as "gene over-expression" or "gene under-expression". Thus, mRNA expression is not commonly considered to be "tumor specific", but "tumor associated" (via over-expression). The distinction is important, for "tumor specific" molecules are an ideal that is devoid of detection interpretation ambiguity and off targeting. So while it has become increasingly clear that there are few if any "genes" only expressed in tumors, aside from fusion transcripts (Annala et al., 2013) the extent to which tumor-specific mRNA isoforms exist is unknown.

Transcriptome sequencing (RNA-seq) is a genomics technology whose principle purpose is to enable genome-wide expression measurements of mRNA isoforms—the level at which distinct tumor-specific mRNA molecules are to be found. In order to apply RNA-seq for the purpose of identifying mRNA isoforms that tumors express and normal tissues do not express, a large compendium of RNA-seq data from malignant and normal tissues is required. The Cancer Genome Atlas (TCGA) (11) is a large NIH-sponsored effort to study the RNA and DNA in 500 tumors for many cancer types, and the Genotype-Tissue Expression (GTEx) program (Lonsdale et al., 2013) is a large NIH-sponsored effort to study the RNA and DNA in thousands of samples from >50 distinct normal tissue sites. Both of these programs are multi-center efforts that are generating molecular profiling data at a rate, scale, and cost that almost certainly could not be borne by any single entity. The primary intention of these efforts is to generate a public resource in order to catalyze leaps in progress across all aspects of cancer care, prevention, and therapy. The raw transcriptome data being produced by these efforts has tremendous discovery potential, but to date they have not been rigorously evaluated for their potential of yielding tumor-specific molecules for diagnostic and therapeutic applications.

SUMMARY

At present there is no available test for the early detection of ovarian cancer. With one exception, all proposed approaches have been based on blood. The exception is also based on Pap smear, but it relies on the detection of particular DNA mutations though massive DNA sequencing. The present method is not based on blood, but on cells collected by Pap smear or endometrial biopsy.

The major component of the present diagnostic is a set of mRNA isoforms that are only expressed in ovarian tumor cells and only exist as a product of the disease due to the deregulated environment within tumor cells. To date approximately 20 such isoforms have been identified. In particular, the identification of a number of mRNA isoforms that are only expressed in ovarian tumors is useful in a diagnostic test that detects the presence of an ovarian tumor in a woman's body through the detection of these isoforms in a Pap smear and/or endometrial biopsy and/or free (cell free, i.e., not within a cell) nucleic acid in blood. This disclosure is likely to be able to detect the presence of even just a few tumor cells, making it an effective test for the detection of very small ovarian tumors. Such sensitivity means that it may function as an early ovarian cancer detection test.

In one embodiment, the disclosure provides methods and primers or probes to hybridize to, sequence and/or amplify mRNA isoforms that were expressed only in patients with ovarian tumors and so can be configured into a diagnostic test to detect the presence of an ovarian tumor in a Pap smear and/or endometrial biopsy (which are routinely collected in a gynecologic exam), as opposed to blood (which requires a separate procedure). The methods may be employed to detect the presence of even just a few tumor cells and, thus, it could function as an early ovarian cancer detection test.

In one embodiment, the disclosure provides a diagnostic reagent or device comprising a biomarker such as a nucleic acid probe and/or primers specific for at least one mRNA shown in FIG. 4, or a specific isoform thereof, or a ligand for a protein encoded by the mRNA isoform, wherein optionally at least one probe, primer or ligand is associated with a detectable label or with a substrate. The biomarker is selected from one or more genes or encoded proteins of genes in FIG. 4, and nucleic acid molecules or proteins having at least 80%, at least 90%%, at least 95% or at least 99% sequence homology or sequence identity with any of the above biomarkers. In certain embodiments, the biomarker sequence or ligand in the reagent or device is associated with a molecule or moiety capable alone or in combination with one or more additional molecules of generating a detectable signal. In other embodiments, the biomarker sequence or ligand in the reagent or device is associated with a substrate on which the sequence or ligand is immobilized. In one embodiment, the sample is a tissue sample. In another embodiment, the sample is a physiological fluid sample, e.g., a blood sample. In another aspect, the diagnostic reagent or device comprises a set of multiple biomarkers or multiple ligands to biomarkers, each individually capable of specifically complexing with, binding to, or quantitatively detecting or identifying a single biomarker.

In one embodiment, a method for detecting ovarian cancer in a subject is provided that includes obtaining a physiological sample from a human; measuring the presence or amount of at least one mRNA isoform in FIG. 4 or at least one mRNA isoform of at least one gene in FIG. 4; and determining whether the presence or amount of the at least one isoform is indicative of ovarian cancer in the human. In one embodiment, the physiological sample is a tissue sample, for example, the sample is from the endometrium or cervix. In one embodiment, a plurality of probes specific for isoforms of MYLPF, LSR, OPN3, RP11-3JL1, TMPRSS3, ETV4. SLC44A4, ESR1, TNFRSF8, SLC44A4, MUC16, RAB11FIP4, AURKA, huhare, STON2. FOXM1, CTD-2616J11.4, ACO191171, CD9, PTH2R, SPC24, LINC00284, or C19orf53, or any combination thereof, is employed to detect unamplified RNA, amplified RNA, or cDNA obtained from mRNA. In one embodiment, the probes are in a microarray, e.g., on a solid substrate. In one embodiment, a plurality of primers and probes specific for isoforms of MYLPF, LSR, OPN3, RP11-3JL1, TMPRSS3, ETV4, SLC44A4, ESR1, TNFRSF8, SLC44A4, MUC16, RAB11FIP4, AURKA, huhare, STON2, FOXM1, CTD-2616J11.4, ACO191171, CD9, PTH2R, SPC24, LINC00284, or C19orf53, or any combination thereof, is employed. In one embodiment, a plurality of primers and probes specific for isoforms of MYLPF, LSR, OPN3, RP11-3JL1, TMPRSS3, ETV4, SLC44A4, ESR1, TNFRSF8, MUC16, RAB11FIP4, AURKA, huhare, STON2, FOXM1, CTD-2616J11.4, ACO191171, CD9, PTH2R, SPC24, LINC00284, C19orf53, CDCA5, PRAME, FGFRL1, CHODL, VTCNA, SLC22A18, CDH24, VASN, WFDC2, FOXM1, or any combination thereof, is employed. In one embodiment, the presence or amount of the isoform is indicative of high grade serous ovarian carcinoma. In one embodiment, the method further includes determining the presence or amount of a biomarker selected from: ApoC1, Hemoglobin alpha/beta, ApoAII, ApoCII, Calcyclin. Calgranulin C, Calgranulin C (truncated form), Calgranulin A or IgG heavy chain. In one embodiment, the method further includes determining the presence or amount of CA 125 II, CA1 5-3, CA1 9-9. CA72-4, CA 195, CEA, creatine kinase B (CKB), Dianon NB 70/K, haptoglobin, ITIH4, galactosyltransferase, haptoglobin, HE4, hepcidin, HER-2/neu, macrophage colony stimulating factor (M-CSF, CSF-I), prostatin, osteopontin, esoinophil-derived neurotoxin, extracellular domain of the epidermal growth factor receptor (p 11 OEGFR), kallikrein 6 and kallikrein 10, LASA, leptin, lysophosphatidic acid (LPA), placental alkaline phosphatase (PLAP), prolactin, SMRP, insulin-like growth factor I, IGF-II, hemoglobin, urinary gonadotropin peptide, Sialyl TN, Tissue peptide antigen (TPA), tumor associated trypsin inhibitor (TATI), and modified forms thereof. In one embodiment, the presence or amount of a plurality of isoforms of MYLPF, LSR, OPN3, RP11-3JL1, TMPRSS3, ETV4, SLC44A4, ESR1, TNFRSF8, SLC44A4, or MUC16 is determined. In one embodiment, the presence or amount of a plurality of isoforms of RAB11FIP4, AURKA, huhare, STON2, FOXM1, CTD-2616J11.4, ACO191171, CD9, PTH2R, SPC24, LINC00284, or C19orf53 is determined. In one embodiment, the presence or amount of a plurality of isoforms of MYLPF, LSR, OPN3, RP11-3JL1, TMPRSS3, ETV4, SLC44A4, ESR1, TNFRSF8, SLC44A4, MUC16, RAB11FIP4, AURKA, huhare, STON2, FOXM1, CTD-2616J11.4. ACO191171, CD9, PTH2R, SPC24, LINC00284, or C19orf53, or any combination hereof, is determined. In one embodiment, the presence or amount of at least 2, at least 5, at least 10, at least 12, or at least 20 of the mRNA isoforms is determined. In one embodiment, the presence or amount is determined using RT-qPCR, hybridization with one or more probes that detect the one or more isoforms, or RNA sequencing.

In another embodiment, the disclosure provides a kit, panel or microarray comprising at least one diagnostic reagent described herein, and optionally two or more diagnostic reagents, each reagent identifying a different biomarker. In one embodiment, the kit comprises diagnostic reagents that bind to or complex individually with 2, 3, 4, 5, 6, 7, 8, 9, 10, 11, 12, 13, 14, 15, 16, 17, 18 or more biomarkers. In another embodiment, the kit, panel or microarray includes diagnostic reagents that bind to or complex individually with at least one additional known marker, isoform, pro-form, modified molecular form, or peptide fragment or homolog thereof.

In one embodiment a composition having a plurality of probes specific for a plurality of mRNA isoforms in FIG. 4, or at least one primer having a nucleotide sequence comprising one of SEQ ID Nos. 1-136 or the complement thereof, or having at least 80% nucleic acid sequence identity thereto, is provided. In one embodiment, the probe or primer is specific for an isoform of MYLPF, LSR. OPN3, RP11-3JL1, TMPRSS3, ETV4, SLC44A4, ESR1, TNFRSF8, SLC44A4, MUC16, RAB11FIP4, AURKA, huhare, STON2, FOXM1, CTD-2616J11.4, ACO191171, CD9. PTH2R, SPC24, LINC00284, or C19orf53 in FIG. 4, or any combination thereof.

In one embodiment, a method for diagnosing or detecting, or monitoring the progress of, ovarian cancer in a subject is provided. In one embodiment, the method comprises contacting a sample obtained from a test subject with a diagnostic reagent or device as described above and quantitatively detecting or identifying at least one biomarker present in the sample. The presence or levels of the selected biomarker(s) may be detected and optionally compared to the presence or levels in a control or profile sample. In one embodiment, a change in biomarker level of the subject's sample from that in the control indicates a diagnosis, risk, or the status of progression or remission of, ovarian cancer in the subject. In one embodiment of this method, an additional step involves detecting or measuring in the sample, the levels of one or more additional known ovarian cancer biomarkers, and comparing the levels of the known biomarker in relation to the levels of the additional biomarkers in the subject's sample with the same biomarkers in a control or profile.

In another aspect, use of any of the diagnostic reagents described herein in a method for the diagnosis of ovarian cancer is provided.

Other aspects and advantages of these compositions and methods are described further in the following detailed description of certain embodiments thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Tumor-specific molecules are needed across diverse areas of oncology for use in early detection, diagnosis, prognosis and therapeutic strategies. The large and growing public compendiums of transcriptome sequencing data (RNA-seq) derived from tumors and normal tissues hold the potential of yielding tumor-specific molecules, but because the data are new they have not been fully explored for this purpose. As described below, bioinformatics algorithms were described and used them with 2,135 tumor and normal RNA-seq datasets to identify a set of mRNA isoforms with tumor-specific expression. These isoforms were rank prioritized by likelihood of being expressed in high-grade serous ovarian (HGS-OvCa) tumors and not in normal tissues, and to date have analyzed 671 top-ranked isoforms using high-throughput RT-qPCR experiments. As described below, 1.2% of the 671 isoforms were expressed in 6-12 of the 12 HGS-OvCa tumors examined but were undetectable in 12 normal tissues. An additional 2.6% were expressed in 1 or 2 normal tissues, which often included ovary or fallopian tissues. In the topmost 5% were isoforms from oncogenic, stem cell/cancer stem cell, and early development loci-including ETV4, FOXM1, LSR, CD9, RAB11FIP4, and FGFRL1.

The systematic process described herein is readily and rapidly applicable to the more than thirty additional tumor types for which sufficient amounts of RNA-seq already exist in public databases. Bioinformatics sequence analysis revealed that many of the isoforms are predicted to encode proteins with unique amino acid sequences, which would allow them to be specifically targeted for one or more therapeutic strategies-including monoclonal antibodies and T-cell-based vaccines.

Figure 4:
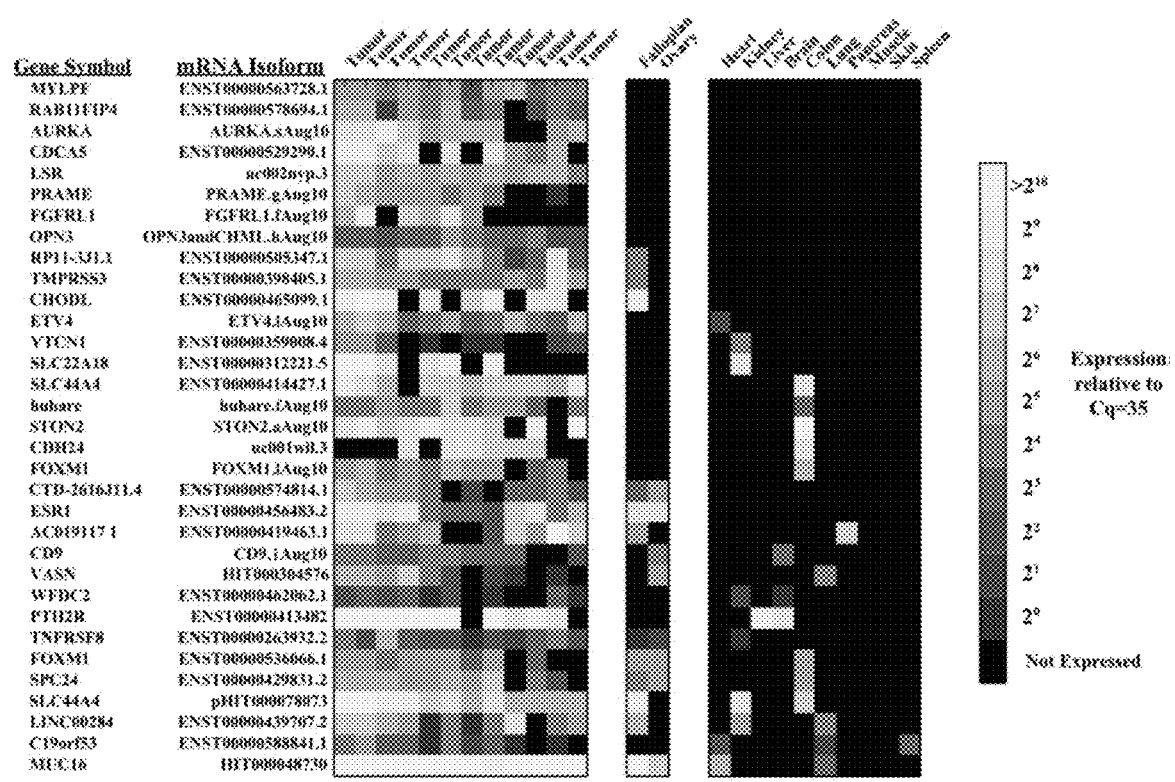
FIG. 4. Top 5% most tumor-specifically expressed mRNA isoforms. In total, 671 mRNA isoforms were selected for tumor-specific confirmation RT-qPCR experiments. Using pooled RNA, a subset of them was found to be only expressed in the tumor RNA pool (see FIG. 3). 86 of these were selected for a second set of RT-qPCR experiments 12 tumor and 12 normal tissue RNA samples, which were not pooled. The 33 mRNA isoforms from the set of 86 are shown, constituting 5% of the original 671.
Figure 5:
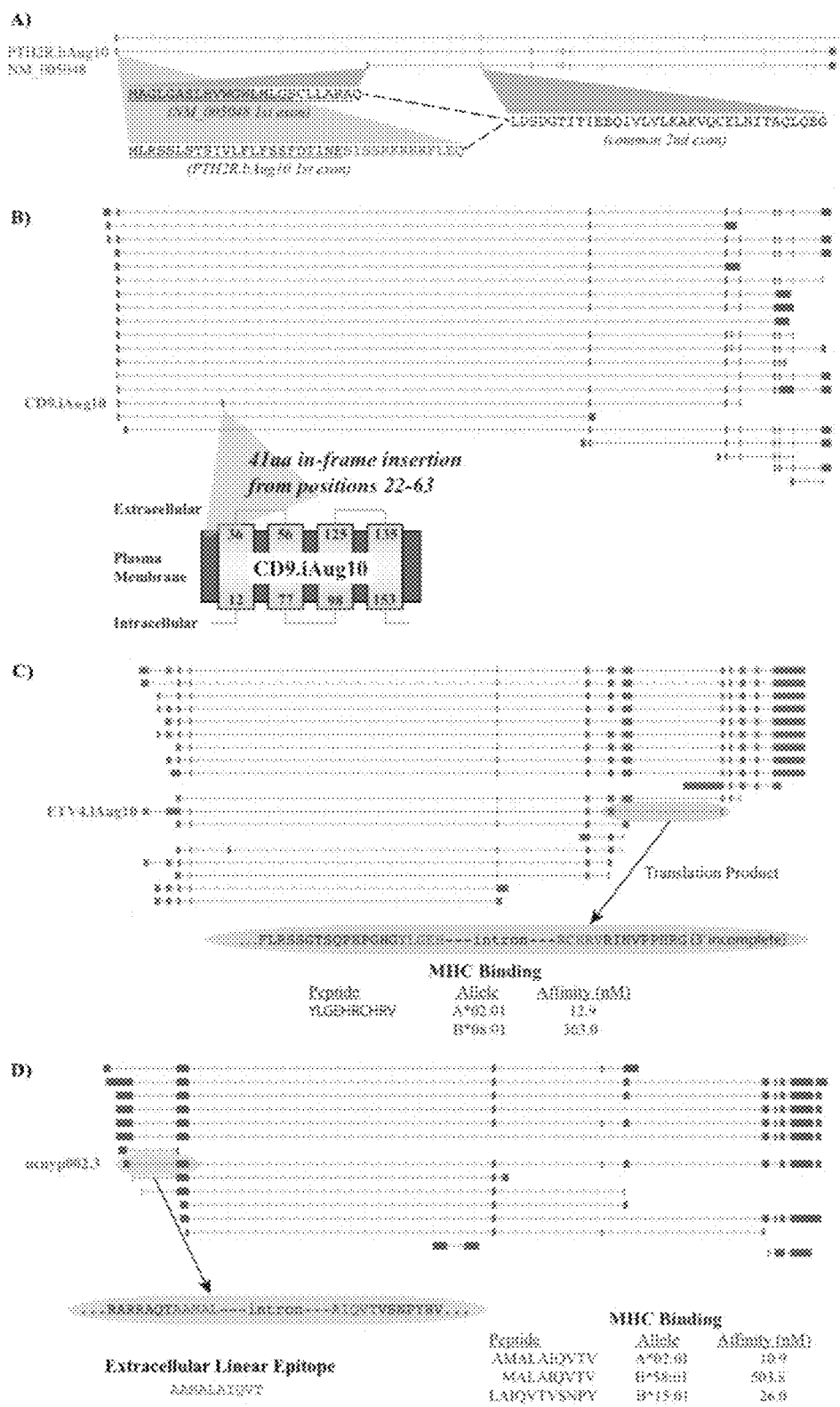
FIGS. 5A-D. Candidate protein therapeutic targets. A) The candidate isoform PTH2R.bAug10 is distinguished from the canonical PTH2R isoform by its alternative first exon, which alters the N-terminal amino acid sequence. Both protein isoforms are predicted to contain signal peptides (that are likely cleaved). After signal peptide cleavage, the first exon of PTH2R.bAug10 would still retain a unique 12 aa sequence, which since the protein is a class B GPCR, is expected to be extracellular and thus amenable for antibody targeting. B) The candidate isoform CD9.iAug10 is distinguished by a unique exon, which is expected to add 41 uniquely distinguishing amino acids some of which project into the extracellular environment and constitute a protein-specific antibody target. C) The candidate isoform ETV4.1Aug10 has a unique exon structure that creates a unique splice junction spanning amino acid sequence with high computed binding affinity to two common MHC 1 alleles. D) The LSR mRNA isoform ucnyp002.3 contains a unique splice junction spanning amino acid sequence that is expected to reside in the extracellular domain of this plasma membrane protein and that also contains subsequences that are computed to have moderate to high binding affinity to multiple common MHC 1 alleles. Thus the single amino acid sequence is amenable to two therapeutic modalities. (SEQ ID NOs: 137-147)

The compositions and methods described herein provide means for diagnosing or detecting the existence or absence of, or monitoring the progress of, ovarian cancer in a subject using one or more of the biomarkers identified in FIGS. 4-5 in optional combination with one or more known ovarian cancer-associated biomarkers. Diagnostic reagents that can detect and measure the target biomarkers and sets of biomarkers identified herein and methods for evaluating the level or ratios of these target biomarkers vs. their level(s) in a variety of reference standards or controls of different conditions or stages in ovarian cancer are valuable tools in the early detection and monitoring of ovarian cancer.

Figure 1:
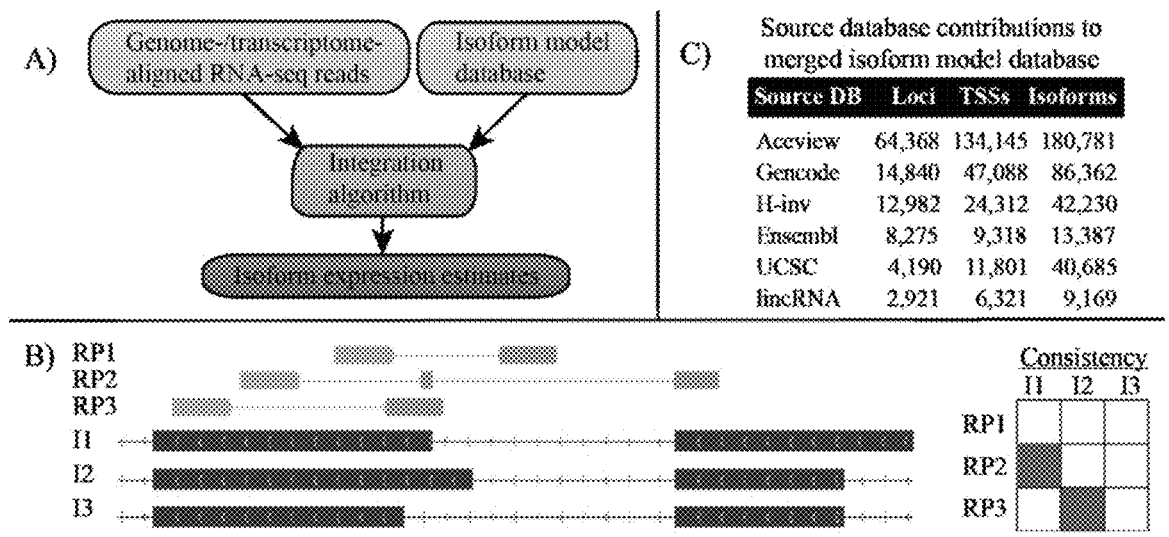
FIGS. 1A-C. RNA-seq bioinformatics. A) RNA-seq computational pipeline broadly conforms to the standard three-component RNA-seq computational pipeline for organisms with a sequenced genome. B) In the approach, read pairs (RP) with maximally sensitive parameterizations were aligned and use all known splice junctions, allowing even 1 bp splice junction "overhangs". Nucleotide-level read-to-isoform consistency analysis identifies and records the read pair-isoform tuples that are exactly concordant and filters out read pairs that are not exactly concordant with some known isoform (I). C) Isoform non-identifications (false negatives) are minimized with the isoform model database that is a merger of the six major isoform model databases worldwide. Given the read pair-isoform tuples from B), a parsimony principle is used to subsequently minimize false isoform identifications (false positives).

In one embodiment, the compositions and methods allow the detection and measurement of the mRNA isoforms or mRNA or protein levels or ratios of one or more "target" biomarkers of FIG. 1 in a biological sample, e.g., a tissue sample such as a PAP smear or endometrial or ovarian biopsy. Diagnostic reagents that can detect and measure these target biomarkers and methods for evaluating the level or ratios of these target biomarkers vs. their level(s) in a variety of reference standards or controls of different conditions or stages in ovarian cancer are valuable tools in the early detection and monitoring of ovarian cancer.

I. Definitions

"Patient" or "subject" as used herein means a female mammalian animal, including a human, a veterinary or farm animal, a domestic animal or pet, and animals normally used for clinical research. In one embodiment, the subject of these methods and compositions is a human.

By "biomarker" or "biomarker signature" as used herein is meant a single mRNA or single protein or a combination of mRNAs and/or proteins or peptide fragments thereof, the levels or relative levels or ratios of which significantly change (either in an increased or decreased manner) from the level or relative levels present in a subject having one physical condition or disease or disease stage from that of a reference standard representative of another physical condition or disease stage. Throughout this specification, wherever a particular biomarker is identified by name, it should be understood that the term "biomarker" includes those listed in FIGS. 4-5. These biomarkers may be combined to form certain sets of biomarkers or ligands to biomarkers in diagnostic reagents. Still other "additional" biomarkers are mentioned specifically herein in combination with the biomarkers of FIGS. 4-5. Biomarkers described in this specification include any physiological molecular forms, or modified physiological molecular forms, isoforms, pro-forms, and fragments thereof, unless otherwise specified. It is understood that all molecular forms useful in this context are physiological, e.g., naturally occurring in the species.

In one embodiment, at least one biomarker of FIGS. 4-5 forms a suitable biomarker signature for use in the methods and compositions. In one embodiment, at least two biomarkers form a suitable biomarker signature for use in the methods and compositions. In another embodiment, at least three biomarkers form a suitable biomarker signature for use in the methods and compositions. In another embodiment, at least four biomarkers form a suitable biomarker signature for use in the methods and compositions. In another embodiment, at least five biomarkers form a suitable biomarker signature for use in the methods and compositions. In another embodiment, at least six biomarkers form a suitable biomarker signature for use in the methods and compositions. In another embodiment, at least seven biomarkers form a suitable biomarker signature for use in the methods and compositions. In another embodiment, at least eight biomarkers form a suitable biomarker signature for use in the methods and compositions. In still further embodiments, at least 9, at least 10, at least 11, at least 12, at least 13, at least 14, at least 15, at least 16, at least 17, or all of the biomarkers of FIGS. 4-5 can be used alone or with additional biomarkers.

By "isoform" or "multiple molecular form" is meant an alternative expression product or variant of a single gene in a given species, including forms generated by alternative splicing, single nucleotide polymorphisms, alternative promoter usage, alternative translation initiation small genetic differences between alleles of the same gene, and posttranslational modifications (PTMs) of these sequences.

"Reference standard" as used herein refers to the source of the reference biomarker levels. The "reference standard" may be provided by using the same assay technique as is used for measurement of the subject's biomarker levels in the reference subject or population, to avoid any error in standardization. The reference standard is, alternatively, a numerical value, a predetermined cutpoint, a mean, an average, a numerical mean or range of numerical means, a numerical pattern, a ratio, a graphical pattern or a protein abundance profile or protein level profile derived from the same biomarker or biomarkers in a reference subject or reference population. In an embodiment, in which expression of nucleic acid sequences encoding the biomarkers is desired to be evaluated, the reference standard can be an expression level of one or more biomarkers or an expression profile.

"Reference subject" or "Reference Population" defines the source of the reference standard. In one embodiment, the reference is a human subject or a population of subjects having no ovarian cancer, i.e., healthy controls or negative controls. In yet another embodiment, the reference is a human subject or population of subjects with one or more clinical indicators of ovarian cancer, but who did not develop ovarian cancer. In still another embodiment, the reference is a human subject or a population of subjects having benign ovarian nodules or cysts. In still another embodiment, the reference is a human subject or a population of subjects who had ovarian cancer, following surgical removal of an ovarian tumor. In another embodiment, the reference is a human subject or a population of subjects who had ovarian cancer and were evaluated for biomarker levels prior to surgical removal of an ovarian tumor. Similarly, in another embodiment, the reference is a human subject or a population of subjects evaluated for biomarker levels following therapeutic treatment for ovarian cancer. In still another embodiment, the reference is a human subject or a population of subjects prior to therapeutic treatment for an ovarian cancer. In still other embodiments of methods described herein, the reference is obtained from the same test subject who provided a temporally earlier biological sample. That sample can be pre- or post-therapy or pre- or post-surgery.

Other potential reference standards are obtained from a reference that is a human subject or a population of subjects having early stage ovarian cancer. In another embodiment the reference is a human subject or a population of subjects having advanced stage ovarian cancer. In still another embodiment, the reference is a human subject or a population of subjects having a subtype of epithelial ovarian cancer. In still another embodiment, the reference is a human subject or a population of subjects having serous ovarian cancer or serous papillary adenocarcinoma. In still another embodiment, the reference is a human subject or a population of subjects having mucinous ovarian cancer. In still another embodiment, the reference is a human subject or a population of subjects having clear cell ovarian cancer. In still another embodiment, the reference is a subject or a population of subjects having endometrioid ovarian cancer. In another embodiment, the reference is a human subject or a population of subjects having Mullerian ovarian cancer. In another embodiment, the reference is a human subject or a population of subjects having undifferentiated ovarian cancer or an ovarian sarcoma. In another embodiment the reference standard is a combination of two or more of the above reference standards.

"Sample" as used herein means any biological fluid or tissue that potentially contains the ovarian cancer biomarkers of FIGS. 4-5. In one embodiment, the samples may include biopsy tissue, tumor tissue, surgical tissue, circulating tumor cells, or other tissue. Such samples may further be diluted with saline, buffer or a physiologically acceptable diluent. Alternatively, such samples are concentrated by conventional means. In certain embodiments, e.g., those in which expression levels of nucleic acid sequences encoding the biomarkers are desired to be evaluated, the samples may include biopsy tissue, surgical tissue, circulating tumor cells, or other tissue. The degree of change in biomarker level may vary with each individual and is subject to variation with each population. For example, in one embodiment, a large change, e.g., 2-3 fold increase or decrease in levels of a small number of biomarkers, e.g., from 1 to 9 characteristic biomarkers, is statistically significant. In another embodiment, a smaller relative change in 10 or more (i.e., about 10, 20, 24, 29, or 30 or more biomarkers) is statistically significant. The degree of change in any biomarker(s) expression varies with the condition, such as type of ovarian cancer and with the size or spread of the cancer or solid tumor. The degree of change also varies with the immune response of the individual and is subject to variation with each individual. For example, in one embodiment of this disclosure, a change at or greater than a 1.2 fold increase or decrease in level of a biomarker or more than two such biomarkers, or even 3 or more biomarkers, is statistically significant. In another embodiment, a larger change, e.g., at or greater than a 1.5 fold, greater than 1.7 fold or greater than 2.0 fold increase or a decrease in expression of a biomarker(s) is statistically significant. This is particularly true for cancers without solid tumors. Still alternatively, if a single biomarker level is significantly increased in biological samples which normally do not contain measurable levels of the biomarker, such increase in a single biomarker level may alone be statistically significant. Conversely, if a single biomarker level is normally decreased or not significantly measurable in certain biological samples which normally do contain measurable levels of the biomarker, such decrease in level of a single biomarker may alone be statistically significant.

A change in level of a biomarker required for diagnosis or detection by the methods described herein refers to a biomarker whose level is increased or decreased in a subject having a condition or suffering from a disease, specifically ovarian cancer, relative to its expression in a reference subject or reference standard. Biomarkers may also be increased or decreased in level at different stages of the same disease or condition. The levels of specific biomarkers differ between normal subjects and subjects suffering from a disease, benign ovarian nodules, or cancer, or between various stages of the same disease. Levels of specific biomarkers differ between pre-surgery and post-surgery patients with ovarian cancer. Such differences in biomarker levels include both quantitative, as well as qualitative, differences in the temporal or relative level or abundance patterns among, for example, biological samples of normal and diseased subjects, or among biological samples which have undergone different disease events or disease stages. For the purpose of this disclosure, a significant change in biomarker levels when compared to a reference standard is considered to be present when there is a statistically significant ($p<0.05$) difference in biomarker level between the subject and reference standard or profile, or significantly different relative to a predetermined cut-point.

The term "ligand" refers, with regard to protein biomarkers, to a molecule that binds or complexes with a biomarker protein, molecular form or peptide, such as an antibody, antibody mimic or equivalent that binds to or complexes with a biomarker identified herein, a molecular form or fragment thereof. In certain embodiments, in which the biomarker expression is to be evaluated, the ligand can be a nucleotide sequence, e.g., polynucleotide or oligonucleotide, primer or probe.

As used herein, the term "antibody" refers to an intact immunoglobulin having two light and two heavy chains or fragments thereof capable of binding to a biomarker protein or a fragment of a biomarker protein. Thus a single isolated antibody or fragment may be a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, an Fv construct, a Fab construct, an Fc construct, a light chain variable or complementarity determining region (CDR) sequence, etc.

As used herein, "labels" or "reporter molecules" are chemical or biochemical moieties useful for labeling a ligand, e.g., amino acid, peptide sequence, protein, or antibody. "Labels" and "reporter molecules" include fluorescent agents, chemiluminescent agents, chromogenic agents, quenching agents, radionucleotides, enzymes, substrates, cofactors, inhibitors, radioactive isotopes, magnetic particles, and other moieties known in the art. "Labels" or "reporter molecules" are capable of generating a measurable signal and may be covalently or noncovalently joined to a ligand.

As used herein the term "cancer" refers to or describes the physiological condition in mammals that is typically characterized by unregulated cell growth. More specifically, as used herein, the term "cancer" means any ovarian cancer. In one embodiment, the ovarian cancer is an epithelial ovarian cancer or subtype as referred to in "conditions" above. In still an alternative embodiment, the cancer is an "early stage" (I or II) ovarian cancer. In still another embodiment, the cancer is a "late stage" (III or IV) ovarian cancer.

The term "tumor," as used herein, refers to all neoplastic cell growth and proliferation, whether malignant or benign, and all pre-cancerous and cancerous cells and tissues.

The term "microarray" refers to an ordered arrangement of binding/complexing array elements, e.g., nucleic acid probes or ligands, e.g. antibodies, on a substrate.

By "significant change in expression" is meant an upregulation in the expression level of a nucleic acid sequence, e.g., genes or transcript, encoding a selected biomarker, in comparison to the selected reference standard or control: a downregulation in the expression level of a nucleic acid sequence, e.g., genes or transcript, encoding a selected biomarker, in comparison to the selected reference standard or control; or a combination of a pattern or relative pattern of certain upregulated and/or down regulated biomarker genes. The degree of change in biomarker expression can vary with each individual as stated above for protein biomarkers.

The term "polynucleotide," when used in singular or plural form, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The term "polynucleotide" specifically includes cDNAs. The term includes DNAs (including cDNAs) and RNAs that contain one or more modified bases. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide of less than 20 bases, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

II. Biomarkers and Biomarker Signatures Useful in the Methods and Compositions

The "targets" of the compositions and methods of these disclosures include, in one aspect, biomarkers listed in FIGS. 4-5, optionally with other biomarkers identified herein, fragments, particularly unique fragments thereof, and molecular forms thereof. In certain embodiments, superior diagnostic tests for diagnosing the existence of ovarian cancer utilize at least one of the ligands that bind or complex with one of biomarkers of FIGS. 4-5, or one of the fragments or molecular forms thereof. In other embodiments, superior diagnostic tests for distinguishing ovarian cancer from one of the conditions recited above utilize multiple ligands, each individually detecting a different specific target biomarker identified herein, or isoform, modified form or peptide thereof. In still other methods, no ligand is necessary.

III. Diagnostic Reagents, Devices and Kits

A. Labeled or Immobilized Biomarkers or Peptides or Molecular Forms

In one embodiment, diagnostic reagents or devices for use in the methods of diagnosing ovarian cancer include one or more biomarkers identified in FIGS. 4-5 optionally associated with a detectable label or portion of a detectable label system. In another embodiment, a diagnostic reagent includes one or more target biomarker or peptide fragment thereof identified in FIGS. 4-5, immobilized on a substrate. In still another embodiment, combinations of such labeled or immobilized biomarkers are suitable reagents and components of a diagnostic kit or device.

Any combination of labeled or immobilized biomarkers can be assembled in a diagnostic kit or device for the purposes of diagnosing ovarian cancer, such as those combinations of biomarkers discussed herein. For these reagents, the labels may be selected from among many known diagnostic labels. Similarly, the substrates for immobilization in a device may be any of the common substrates, glass, plastic, a microarray, a microfluidics card, a chip, a bead or a chamber.

B. Labeled or Immobilized Ligands that Bind or Complex with the Biomarkers

In another embodiment, the diagnostic reagent or device includes a ligand that binds to or complexes with a biomarker shown in FIGS. 4-5. In one embodiment, such a ligand desirably binds to a protein biomarker or a unique peptide contained therein, and can be an antibody which specifically binds a single biomarker of FIG. 4 or 5. Various forms of antibody, e.g., polyclonal, monoclonal, recombinant, chimeric, as well as fragments and components (e.g., CDRs, single chain variable regions, etc.) or antibody mimics or equivalents may be used in place of antibodies. The ligand itself may be labeled or immobilized.

In another embodiment, suitable labeled or immobilized reagents include at least 2, 3, 4, 5, 6, 7 8, 9, 10, 11, 12, 13, 14, 15, 16, 17 or 18 or more ligands. Each ligand binds to or complexes with a single biomarker or protein/peptide, fragment, or molecular form of the biomarker(s) of FIGS. 4-5. Any combination of labeled or immobilized biomarker ligands can be assembled in a diagnostic kit or device for the purposes of diagnosing ovarian cancer.

Thus, a kit or device can contain multiple reagents or one or more individual reagents. For example, one embodiment of a composition includes a substrate upon which the biomarkers or ligands are immobilized. In another embodiment, the kit also contains optional detectable labels, immobilization substrates, optional substrates for enzymatic labels, as well as other laboratory items.

The diagnostic reagents, devices, or kits compositions based on the biomarkers of FIG. 4-5, optionally associated with detectable labels, can be presented in the format of a microfluidics card, a chip or chamber, a bead or a kit adapted for use with assays formats such as sandwich ELISAs, multiple protein assays, platform multiplex ELISAs, such as the BioRad Luminex platform, Mass spectrometry quantitative assays, or PCR RT-PCR or Q PCR techniques. In one embodiment, a kit includes multiple antibodies directed to bind to one or more of the combinations of biomarkers described above, wherein the antibodies are associated with detectable labels.

In one embodiment, the reagent ligands are nucleotide sequences, the diagnostic reagent is a polynucleotide or oligonucleotide sequence that hybridizes to gene, gene fragment, gene transcript or nucleotide sequence encoding a biomarker of FIGS. 4-5 or encoding a unique peptide thereof. Such a polynucleotide/oligonucleotide can be a probe or primer, and may itself be labeled or immobilized. In one embodiment, ligand-hybridizing polynucleotide or oligonucleotide reagent(s) are part of a primer-probe set, and the kit comprises both primer and probe. Each said primer-probe set amplifies a different gene, gene fragment or gene expression product that encodes a different biomarker of FIGS. 4-5, optionally including one or more additional known biomarkers, such as CA125, HE4, CLIC1, PRDX6, CTSD, CLIC4, IGFPB2 or LRG1. For use in the compositions the PCR primers and probes may be designed based upon intron sequences present in the biomarker gene(s) to be amplified selected from the gene expression profile. The design of the primer and probe sequences is within the skill of the art once the particular gene target is selected. The particular methods selected for the primer and probe design and the particular primer and probe sequences are not limiting features of these compositions. A ready explanation of primer and probe design techniques available to those of skill in the art is summarized in U.S. Pat. No. 7,081,340, with reference to publically available tools such as DNA BLAST software, the Repeat Masker program (Baylor College of Medicine), Primer Express (Applied Biosystems): MGB assay-by-design (Applied Biosystems): Primer3 (Steve Rozen and Helen J. Skaletsky (2000) Primer3 on the WWW for general users and for biologist programmers and other publications.

In general, PCR primers and probes used in the compositions described herein are generally 17-30 bases in length, and contain about 20-80%, such as, for example, about 50-60% G+C bases. Melting temperatures of between 50 and 80.degree. C., e.g. about 50 to 70.degree. C. may be preferred.

The selection of the ligands, biomarker sequences, their length, suitable labels and substrates used in the reagents and kits are routine determinations made by one of skill in the art in view of the teachings herein of which biomarkers form signature suitable for the diagnosis of ovarian cancer.
Methods for Diagnosing or Monitoring Ovarian Cancer In another embodiment, a method for diagnosing or detecting or monitoring the progress of ovarian cancer in a subject comprises, or consists of, a variety of steps.

A. Sample Preparation

The test sample is obtained from a human subject who is to undergo the testing or treatment. The subject's sample can in one embodiment be provided before initial diagnosis, so that the method is performed to diagnose the existence of an ovarian cancer. In another embodiment, depending upon the reference standard and markers used, the method is performed to diagnose the stage of ovarian cancer. In another embodiment, depending upon the reference standard and markers used, the method is performed to diagnose the type or subtype of ovarian cancer from the types and subtypes identified above. In another embodiment, the subject's sample can be provided after a diagnosis, so that the method is performed to monitor progression of an ovarian cancer. In another embodiment, the sample can be provided prior to surgical removal of an ovarian tumor or prior to therapeutic treatment of a diagnosed ovarian cancer and the method used to thereafter monitor the effect of the treatment or surgery, and to check for relapse. In another embodiment, the sample can be provided following surgical removal of an ovarian tumor or following therapeutic treatment of a diagnosed ovarian cancer, and the method performed to ascertain efficacy of treatment or relapse. In yet another embodiment the sample may be obtained from the subject periodically during therapeutic treatment for an ovarian cancer, and the method employed to track efficacy of therapy or relapse. In yet another embodiment the sample may be obtained from the subject periodically during therapeutic treatment to enable the physician to change therapies or adjust dosages. In one or more of these embodiments, the subject's own prior sample can be employed in the method as the reference standard.

Where the sample is a fluid, e.g., blood, serum or plasma, obtaining the sample involves simply withdrawing and preparing the sample in the traditional fashion for contact with the diagnostic reagent. Where the sample is a tissue or tumor sample, it may be prepared in the conventional manner for contact with the diagnostic reagent.

The method further involves contacting the sample obtained from a test subject with a diagnostic reagent as described herein under conditions that permit the reagent to bind to or complex with one or more biomarker(s) of FIGS. 4-5 which may be present in the sample. This method may employ any of the suitable diagnostic reagents or kits or compositions described above.

B. Measuring Biomarker Levels

Thereafter, a suitable assay is employed to detect or measure in the sample the p level (actual or relative) of one or more biomarker(s) of FIGS. 4-5. Alternatively, a suitable assay is employed to generate an abundance profile (actual or relative or ratios thereof) of multiple biomarkers of FIGS. 4-5 from the sample or of multiple different molecular forms of the same biomarker or both.

The measurement of the biomarker(s) in the biological sample may employ any suitable ligand, e.g., nucleic acid probe, RT-PCR, antibody, antibody mimic or equivalent (or antibody to any second biomarker) to detect the biomarker. For example, the binding portion of a biomarker antibody may also be used in a diagnostic assay. As used herein, the term "antibody" may also refer, where appropriate, to a mixture of different antibodies or antibody fragments that bind to the selected biomarker. Such different antibodies may bind to different biomarkers or different portions of the same biomarker protein than the other antibodies in the mixture. Such differences in antibodies used in the assay may be reflected in the CDR sequences of the variable regions of the antibodies. Such differences may also be generated by the antibody backbone, for example, if the antibody itself is a non-human antibody containing a human CDR sequence, or a chimeric antibody or some other recombinant antibody fragment containing sequences from a non-human source. Antibodies or fragments useful in the method may be generated synthetically or recombinantly, using conventional techniques or may be isolated and purified from plasma or further manipulated to increase the binding affinity thereof. It should be understood that any antibody, antibody fragment, or mixture thereof that binds one of the biomarkers of FIGS. 4-5 or a particular sequence of the selected biomarker as defined in FIGS. 4-5 may be employed in the methods described herein, regardless of how the antibody or mixture of antibodies was generated.

Similarly, the antibodies may be tagged or labeled with reagents capable of providing a detectable signal, depending upon the assay format employed. Such labels are capable, alone or in concert with other compositions or compounds, of providing a detectable signal. Where more than one antibody is employed in a diagnostic method, e.g., such as in a sandwich ELISA, the labels are desirably interactive to produce a detectable signal. In one embodiment, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength.

Other label systems that may be utilized in the methods and devices of this disclosure are detectable by other means, e.g., colored latex microparticles (Bangs Laboratories, Indiana) in which a dye is embedded may be used in place of enzymes to provide a visual signal indicative of the presence of the resulting selected biomarker-antibody complex in applicable assays. Still other labels include fluorescent compounds, radioactive compounds or elements. In one embodiment, an anti-biomarker antibody is associated with, or conjugated to a fluorescent detectable fluorochrome, e.g., fluorescein isothiocyanate (FITC), phycoerythrin (PE), allophycocyanin (APC), coriphosphine-O (CPO) or tandem dyes. PE-cyanin-5 (PC5), and PE-Texas Red (ECD). Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP, fluorescein isothiocyanate (FITC) and Alexa dyes. Combinations of such labels, such as Texas Red and rhodamine, FITC+PE, FITC+PECy5 and PE+PECy7, among others may be used depending upon assay method.

Detectable labels for attachment to antibodies useful in diagnostic assays and devices of this disclosure may be easily selected from among numerous compositions known and readily available to one skilled in the art of diagnostic assays. The biomarker-antibodies or fragments useful in this disclosure are not limited by the particular detectable label or label system employed. Thus, selection and/or generation of suitable biomarker antibodies with optional labels for use in this disclosure is within the skill of the art, provided with this specification, the documents incorporated herein, and the conventional teachings of immunology.

Similarly the particular assay format used to measure the selected biomarker in a biological sample may be selected from among a wide range of protein assays, such as described in the examples below. Suitable assays include enzyme-linked immunoassays, sandwich immunoassays, homogeneous assays, immunohistochemistry formats, or other conventional assay formats. In one embodiment, a serum/plasma sandwich ELISA is employed in the method. In another embodiment, a mass spectrometry-based assay is employed. In another embodiment, a MRM assay is employed, in which antibodies are used to enrich the biomarker in a manner analogous to the capture antibody in sandwich ELISAs.

One of skill in the art may readily select from any number of conventional immunoassay formats to perform this disclosure.

Other reagents for the detection of protein in biological samples, such as peptide mimetics, synthetic chemical compounds capable of detecting the selected biomarker may be used in other assay formats for the quantitative detection of biomarker protein in biological samples, such as high pressure liquid chromatography (HPLC), immunohistochemistry, etc.

Employing ligand binding to the biomarker proteins or multiple biomarkers forming the signature enables more precise quantitative assays, as illustrated by the multiple reaction monitoring (MRM) mass spectrometry (MS) assays. As an alternative to specific peptide-based MRM-MS assays that can distinguish specific protein isoforms and proteolytic fragments, the knowledge of specific molecular forms of biomarkers allows more accurate antibody-based assays, such as sandwich ELISA assays or their equivalent. Frequently, the isoform specificity and the protein domain specificity of immune reagents used in pre-clinical (and some clinical) diagnostic tests are not well defined. MRM-MS assays were used to quantitative the levels of a number of the low abundance biomarkers in samples, as discussed in the examples.

In one embodiment, suitable assays for use in these methods include immunoassays using antibodies or ligands to the above-identified biomarkers and biomarker signatures. In another embodiment, a suitable assay includes a multiplexed MRM based assay for two more biomarkers that include one or more of the proteins/unique peptides in FIGS. 4-5. It is anticipated that ultimately the platform most likely to be used in clinical assays will be multi-plexed or parallel sandwich ELISA assays or their equivalent, primarily because this platform is the technology most commonly used to quantify blood proteins in clinical laboratories. MRM MS assays may continue to be used productively to help evaluate the isoform/molecular form specificity of any existing immunoassays or those developed in the future.

C. Detection of a Change in Biomarker Abundance Level and Diagnosis

The level of the one or more biomarker(s) in the subject's sample or the protein abundance profile of multiple said biomarkers as detected by the use of the assays described above is then compared with the level of the same biomarker or biomarkers in a reference standard or reference profile. In one embodiment, the comparing step of the method is performed by a computer processor or computer-programmed instrument that generates numerical or graphical data useful in the appropriate diagnosis of the condition. Optionally, the comparison may be performed manually.

The detection or observation of a change in the level of a biomarker or biomarkers in the subject's sample from the same biomarker or biomarkers in the reference standard can indicate an appropriate diagnosis. An appropriate diagnosis can be identifying a risk of developing ovarian cancer, a diagnosis of ovarian cancer (or stage or type thereof), a diagnosis or detection of the status of progression or remission of ovarian cancer in the subject following therapy or surgery, a determination of the need for a change in therapy or dosage of therapeutic agent. The method is thus useful for early diagnosis of disease, for monitoring response or relapse after initial diagnosis and treatment or to predict clinical outcome or determine the best clinical treatment for the subject.

In one embodiment, the change in level of each biomarker can involve an increase of a biomarker or multiple biomarkers in comparison to the specific reference standard. In one embodiment, a selection or all of the biomarkers of FIGS. 4-5 are increased in a subject sample from a patient having ovarian cancer when compared to the levels of these biomarkers from a healthy reference standard. In another embodiment, a selection or all of the biomarkers of FIGS. 4-5 are increased in a subject sample from a patient having ovarian cancer prior to therapy or surgery, when compared to the levels of these biomarkers from a post-surgery or post-therapy reference standard.

In another embodiment, the change in p level of each biomarker can involve a decrease of a biomarker or multiple biomarkers in comparison to the specific reference standard. In one embodiment, a selection or all of the biomarkers of FIGS. 4-5 are decreased in a subject sample from a patient having ovarian cancer following surgical removal of a tumor or following chemotherapy/radiation when compared to the levels of these biomarkers from a pre-surgery/pre-therapy ovarian cancer reference standard or a reference standard which is a sample obtained from the same subject pre-surgery or pre-therapy. In still other embodiments, the changes in levels of the biomarkers may be altered in characteristic ways if the reference standard is a particular type of ovarian cancer, e.g., serous, epithelial, mucinous or clear cell, or if the reference standard is derived from benign ovarian cysts or nodules.

The results of the methods and use of the compositions described herein may be used in conjunction with clinical risk factors to help physicians make more accurate decisions about how to manage patients with ovarian cancers. Another advantage of these methods and compositions is that diagnosis may occur earlier than with more invasive diagnostic measures.

D. Exemplary Embodiment

In one embodiment, the method of diagnosis or risk of diagnosis involves using the nucleic acid hybridizing reagent ligands described above to detect a significant change in expression level of the subject's sample biomarker or biomarkers from that in a reference standard or reference expression profile which indicates a diagnosis, risk, or the status of progression or remission of ovarian cancer in the subject. These methods may be performed in other biological samples, e.g., biopsy tissue samples, tissue removed by surgery, or tumor cell samples, including circulating tumor cells isolated from the blood, to detect or analyze a risk of developing an ovarian cancer, as well as a diagnosis of same. Such methods are also known in the art and include contacting a sample obtained from a test subject with a diagnostic reagent comprising a ligand which is a nucleotide sequence capable of hybridizing to a nucleic acid sequence encoding a biomarker of FIGS. 4-5, said ligand associated with a detectable label or with a substrate. Thereafter one would detect or measure in the sample or from an expression profile generated from the sample, the expression levels of one or more of the biomarkers or ratios thereof. The expression level(s) of the biomarker(s) in the subject's sample or from an expression profile or ratio of multiple said biomarkers are then compared with the expression level of the same biomarker or biomarkers in a reference standard. A significant change in expression level of the subject's sample biomarker or biomarkers from that in the reference standard indicates a diagnosis, risk, or the status of progression or remission of ovarian cancer in the subject.

Suitable assay methods include methods based on hybridization analysis of polynucleotides, methods based on sequencing of polynucleotides, proteomics-based methods or immunochemistry techniques. The most commonly used methods known in the art for the quantification of mRNA expression in a sample include northern blotting and in situ hybridization; RNAse protection assays: and PCR-based methods, such as reverse transcription polymerase chain reaction (RT-PCR) or qPCR. Alternatively, antibodies may be employed that can recognize specific DNA-protein duplexes. The methods described herein are not limited by the particular techniques selected to perform them. Exemplary commercial products for generation of reagents or performance of assays include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test), the MassARRAY-based method (Sequenom, Inc., San Diego, Calif.), differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) and high coverage expression profiling (HiCEP) analysis. The comparison of the quantitative or relative expression levels of the biomarkers may be done analogously to that described above for the comparison of protein levels of biomarkers.

Thus, the various methods, devices and steps described above can be utilized in an initial diagnosis of ovarian cancer or other ovarian condition, as well as in clinical management of patients with ovarian cancer after initial diagnosis. Uses in clinical management of the various devices, reagents and assay methods, include without limitation, monitoring for reoccurrence of disease or monitoring remission or progression of the cancer and either before, during or after therapeutic or surgical intervention, selecting among therapeutic protocols for individual patients, monitoring for development of toxicity or other complications of therapy, and predicting development of therapeutic resistance.

The invention will be further described by the following non-limiting examples.

Example 1

Methods and Materials

RNA-seq bioinformatics. We created a custom isoform model database by merging the six major isoform model databases available worldwide. We used the set of all isoform splice junctions from our custom database and lenient parameterizations to perform highly sensitive genome-wide alignment of RNA-seq paired-end reads. We then performed an alignment-filtering step to remove spurious alignments that can be generated by using lenient parameterization. To filter, we analyzed each read pair alignment to determine whether or not its implied cDNA fragment was a contiguous subsequence of any mRNA isoform(s). We then use the filtered read alignments to compute the subset of our custom isoform model database that most parsimoniously accounted for the filtered alignments. In effect, we created a tailored isoform model database for each RNA-seq data set. Finally, we converted read pair genome alignments to transcriptome alignments and explicitly used the strict correspondence between read pairs and isoforms to compute isoform-level expression.

RT-aPCR.

We performed RT-qPCR experiments according to MIQE guidelines (Bustin et al., 2009), which among other criteria include the use of multiple references for inter-sample comparison and the calculation of PCR reaction efficiencies for quantification. Tumor RNA was obtained from the UC San Diego Moores Cancer Center Biorepository and commercially (Origene). Normal tissue RNA was obtained commercially (Biochain).

Primary RNA-Seq Data

The primary data for the study consisted of the RNA-seq data generated by TCGA for high-grade ovarian serous cystadenocarcinoma (OV) and by the GTEx project for 43 different, non-diseased normal tissues. TCGA has generated RNA-seq data sets for 420 OV samples, but many of them have been redacted or are from replicate aliquots. Table 1 from the Oct. 10, 2013 GDAC Summary Report (http://gdac.broadinstitute.org/runs/stddata_2013_10_10/samples_reportdOV.html) was used to identify the non-redacted samples and the best single sample from replicate aliquots. This curation resulted in 296 samples, for which the raw RNA-seq paired-end read data was downloaded for the study. All of the 1,839 RNA-seq data sets available from GTEx as of Jun. 1, 2013 were used. All of the available paired-end read data specified in the file "SraRunTable_4-15-2013.txt" that was obtained from the SRA Run Selector page on the dbGap (3) website for the GTEx project was downloaded.

RNA-Seq Bioinformatics Pipeline

Stage One—Consolidated Isoform Model Database.

A merged, nonredundant set of gene isoform models was created by first combining the isoform models from the "ncbi_37_Aug10" version of Aceview (4), the version of RefSeq available on Dec. 7, 2012 for GRCh37.p10, the version of UCSC Known Genes for hg19 available on Dec. 8, 2012, version 14 of Gencode, the Human lincRNA Catalog, and version 8.3 of the H-invitational database. We then used the "cuffcompare" program from version 0.9.3 of the Cufflinks software package to make the set nonredundant.

Stage Two—Paired End Read Duplicate Removal and Genome Alignment.

For each RNA-seq data set, all but one read pair in each group of read pairs that were identical in both the left and right read was removed. The resulting set of read pairs was aligned to version hg19 of the human genome reference sequence using STAR. STAR was supplied with the set of all splice junctions in the isoform model database from Stage One and used the following non-default parameter settings: —outStd SAM—outSAMstrandField intronMotif—alignSJDBoverhangMin 1—outFilterMismatchNmax 5—readFilesCommand zcat—seedSearchStartLmax 12—alignSplicedMateMapLminOverLmate 0.08—outFilterScoreMinOverLread 0.08—outFilterMatchNminOverLread 0.08—outFilterMultimapNmax 100—outFilterIntronMotifs RemoveNoncanonicalUnannotated—outSJfilterOverhangMin 12 6 6 6.

Stage Three—Read Pair Consistency Analysis and Isoform Selection.

Software was developed to evaluate each read pair alignment together with each mRNA isoform to which it aligns and to determine at nucleotide resolution whether the RNA fragment implied by the read pair was a strict subsequence of the mRNA isoform nucleotide sequence. From this consistency analysis we constructed a bi-partite graph linking isoforms to consistent read pairs. Read pairs not consistent with any isoform were not included in the bipartite graph and were excluded from further use. To identify the isoforms expressed at a genomic locus, the bi-partite graph and a custom implementation of a greedy solution to the set covering problem were used to determine the set of isoforms that most parsimoniously accounted for all of the filtered read alignments. The results of this stage were 1) a set of paired end read alignments that were basepair level consistent with one or more isoforms and 2) the subset of isoforms that could completely and most parsimoniously account for them.

Stage Four—Calculation of Isoform Expression Levels.

eXpress software package were used to estimate isoform expression levels. The eXpress software requires two input files: a fasta file with mRNA isoform nucleotide sequences and a BAM file with paired end read alignments in transcriptome (i.e., isoform specific) coordinates. Since read alignments generated in Stage Three were in genomic coordinates, the UBU software (https://github.com/mozack/ubu) was downloaded and modified to convert the genomic alignment coordinates of each filtered read pair from Stage Three to isoform coordinates for each isoform to which the read pair was found to be basepair-level consistent. The input fasta file was generated by including only nucleotide sequences for those isoforms constituting the parsimonious set from Stage Three. The only non-default parameter setting was "-max-indel-size 20".

RT-qPCR

Automated Design of PCR Primers for mRNA Isoforms.

Using Primer3 (Untergasser et al., 2012) at its core, automated software was developed to design PCR primers that would only amplify a product for a target isoform. For a target isoform, the software first extracted all isoforms in the consolidated isoform model database at the same genomic locus. This set of isoforms was then used to identify 1) all single splice junctions, 2) all pairs of (not necessarily adjacent) splice junctions, and 3) all splice junction-unique exonic region combinations that were unique to the target isoform. The software then constructed parameterizations that instructed Primer3 how to search for primers for each of these three cases. For single splice junctions, Primer3 attempts to find a) primer pairs that enclose but do not overlap the splice junction and b) primer pairs in which one of the primers overlaps the splice junction. For pairs of splice junctions. Primer3 attempts to find a) primer pairs that surround but do not overlap either splice junction, b) primer pairs in which only one primer overlaps a splice junction, and c) primer pairs in which each primer overlaps one of the splice junctions. For splice junction-exonic region pairs, Primer3 attempts to find a) primer pairs that surround but do not overlap either the splice junction or the exonic region, b) primer pairs in which only one primer overlaps either the splice junction or the unique exonic region, and c) primer pairs in which one primer overlaps the splice junction and the other overlaps the exonic region. These parameterizations were set on a case-by-case basis through the Primer3 arguments SEQUENCE_PRIMER_PAIR_OK_REGION_LIST, SEQUENCE_OVERLAP_JUNCTION_LIST, PRIMER_MIN_LEFT_THREE_PRIME_DISTANCE, PRIMER_MIN_RIGHT_THREE_PRIME_DISTANCE.

The following Primer3 parameter settings were constant for every case: PRIMER_TASK="generic", PRIMER_EXPLAIN_FLAG=1, PRIMER_OPT_SIZE=18, PRIMER_MIN_SIZE=18, PRIMER_MAX_SIZE=23, PRIMER_PRODUCT_OPT_SIZE=100, PRIMER_PRODUCT_SIZE_RANGE=60-450, PRIMER_PAIR_MAX_DIFF_TM=3, PRIMER_MIN_TM=58, PRIMER_MAX_TM=62. PRIMER_OPT_TM=60, PRIMER_SALT_DIVALENT=2.5, PRIMER_DNTP_CONC=0.8.

Until a suitable primer pair is found, the software evaluated the primer pairs returned by Primer3 above in rank order of smallest Primer3 penalty. For the evaluation, it first used the nearest-neighbor thermodynamics based PCR primer specificity checking program MFEPrimer-2.0 (Qu et al., 2012) to verify that only the one intended product was amplified when using the human genome reference sequence and our consolidated transcriptome database as the template. For primer pairs that passed this specificity evaluation step, the software then queried the uMelt webserver (Dwight et al., 2011) to verify that the PCR product would produce only one peak in a melt curve analysis. The first primer pair that passed the amplification specificity and melt curve evaluations was used to define the product that was specific to the target mRNA isoform.

High-Throughput qPCR.

All qPCR experiments were performed in 384-well plates and with a total reaction volume of 10 uL. PCR primer oligo (IDTDNA) molarity was 300 nM and the template cDNA concentration was 10 ng/uL. Experiments were performed on Roche LightCycler 480 for 35 cycles. The KAPA SYBR FAST qPCR kit optimized for the LightCycler 480 was used and the instrument was programmed according to KAPA recommendations. The primer annealing temperature was 54° C. Upon completion of a qPCR experiment, we exported the raw amplification and melting data to a text file.

qPCR software for analysis, quality control, and expression quantification. To calculate the efficiency of a PCR reaction, first the amplification curve was baseline adjusted to zero fluorescence intensity units at cycle 2. Next, simultaneously the amplification curve was smooth and its second derivative calculated using a Savitzky-Golay filter (Savitzky et al., 1964) with order 5 and window size 7. Then the cycle corresponding to the maximum of the second derivative was computed, and it and the three preceding cycles (for a total of four cycles) was used to define the exponential region of the amplification curve. Finally, an implementation of the taking-difference linear regression method (Rao et al., 2013) was used to compute reaction efficiency. To determine the quantification cycle, $C_q$, for each curve in a 384-well plate experiment, the value of fluorescence intensity that was most commonly included in the exponential regions of the wells that were not no-template-control wells was determined. This fluorescence intensity was defined as the threshold intensity, $N_q$. The $C_q$ value for each reaction was than set as the fractional cycle value at which the well's amplification curve equals Nq. $C_q=3^7$ was set for amplification curves that did not reach $N_q$.

Genome-Wide Search Evaluation, and Selection of Reference Amplicons.

Stably expressed reference amplicons are a critical component of a qPCR experiment. To identify the most stably-expressed reference amplicons for the study the consolidated isoform model database was used to identify 2,201,622 splice junctions and splice junction pairs that would give rise to a single, unique amplicon <450 bp from any number of underlying isoforms. For each splice junction/splice junction pair, the sum of the underlying isoforms' expression values in each of the 295 tumor and 1839 normal tissue RNA-seq data sets used was computed. Next, the mean expression and the coefficient of variation (CoV) corresponding to each splice junction/splice junction pair for each of the 44 tissue types (1 tumor plus 43 normal) were computed. Finally, the CoV values for each splice junction/splice junction pair were summed across the 44 tissue types and ranked the sums from smallest to largest. From this final ranking of the most stably expressed reference amplicons, the 16 top-ranked reference amplicons that did not originate from standard "reference genes" and the 16 top-ranked that did were selected. (The symbols of the standard reference genes are ACTB, B2M, GAPDH, GUSB, HPRT1, HSP90AB1, LDHA, NONO, PGK1, PPIA, PPIH, RPLP0, RPLP1, SDHA, TBP, TFRC.) After using the primer design software to design primers for the 32 candidate reference amplicons (see Table 1), qPCR was performed with three ovarian tumor samples (UC San Diego Moores Cancer Center Bioreposi-tory) and three normal tissues (heart, liver, kidney; Biochain) and used the resulting expression values as input into our custom implementation of the geNorm algorithm (Hellemans et al., 2007). From the output of geNorm (see Supplemental FIG. 4), the three most stably expressed amplicons (annotated as references in Table 2) were selected.

TABLE 1

PCR primers for reference amplicon experiments

| Gene Symbol | Len | Fwd $T_m$ | Rev $T_m$ | Forward Primer | Reverse Primer |
|---|---|---|---|---|---|
| SLC25A37 | 223 | 59.9 | 60.1 | TCGGTGAAGAGACAGG GTCT (SEQ ID NO: 1) | GAACTCCTTCGGTCCG CAT (SEQ ID NO: 2) |
| AF011889.4 | 215 | 59.8 | 59.8 | GCTGGAGATGAGACCC AGC (SEQ ID NO: 3) | CAGGTGTCCTCCCTCC CA (SEQ ID NO: 4) |
| WWC2 | 212 | 58.4 | 59.6 | GCTGACTTTGAAGACT ATGTGGA (SEQ ID NO: 5) | ACCTGGGCGGTCTCT ACA (SEQ ID NO: 6) |
| METAP1D | 195 | 60.4 | 59.1 | TGACCGACGCCAACAT GG (SEQ ID NO: 7) | CTGAAGAAACTGCAG CCGG (SEQ ID NO: 8) |
| ZNF542 | 237 | 57 | 58.7 | CAGTAATGGGATGAGT GACATTC (SEQ ID NO: 9) | TGAAATATCCTGGCA ATGGGC (SEQ ID NO: 10) |
| COX18 | 173 | 57.5 | 59.6 | AGAGATGCCAGGCTCA CT (SEQ ID NO: 11) | TCTGAATGTGCTGCC CCC (SEQ ID NO: 12) |
| SYNRG | 203 | 60.4 | 60.6 | CAGTGGGTGGAGCTGC AG (SEQ ID NO: 13) | AGGGGCACTGTTTCC ATGC (SEQ ID NO: 14) |
| DHX38 | 170 | 58.8 | 60.0 | TCAGCAAGACCCCACA GG (SEQ ID NO: 15) | AGGCGCGTTCTCCAG TTC (SEQ ID NO: 16) |
| EIF2B5 | 127 | 59.6 | 59.6 | CTGTGGCAGGGTGTTC GA (SEQ ID NO: 17) | CCACGACCACCTGGG AAG (SEQ ID NO: 18) |

TABLE 1-continued

PCR primers for reference amplicon experiments

| Gene Symbol | Len | Fwd $T_m$ | Rev $T_m$ | Forward Primer | Reverse Primer |
|---|---|---|---|---|---|
| SIRT2 | 179 | 59.9 | 60.0 | TGCAGGAGGCTCAGGACT (SEQ ID NO: 19) | ACAGCGTTCGCTCTGCAT (SEQ ID NO: 20) |
| RBM17 | 127 | 59.9 | 60.1 | ACATGGTTGGTGCGGGAG (SEQ ID NO: 21) | ACTGCTTCATCATCAGGGGC (SEQ ID NO: 22) |
| ANAPC7 | 113 | 59.9 | 59.66 | AAGCCCTGACCCAAAGGC (SEQ ID NO: 23) | AGCCAGTGCGTTCCTCAG (SEQ ID NO: 24) |
| MRPS5 | 118 | 59.2 | 60.3 | TTGGGGAGGCAGTGTTCC (SEQ ID NO: 25) | TGGCGTAGGGATGGGTGT (SEQ ID NO: 26) |
| HSPA9 | 120 | 59.6 | 59.7 | TCCGTGCCTCCAATGGTG (SEQ ID NO: 27) | TGTGCCCCAAGTAATTTTCTGC (SEQ ID NO: 28) |
| PSMD4 | 205 | 59.9 | 58.6 | GCTGACCACACTCACCCC (SEQ ID NO: 29) | AGCCAGTTTCACCAGATCCT (SEQ ID NO: 30) |
| TCP1 | 125 | 59.5 | 57.4 | TGGTGCAACCATCCTGAAG (SEQ ID NO: 31) | CTGCTGCAATAATAACCACTGAA (SEQ ID NO: 32) |
| TBP | 126 | 58.7 | 59.7 | TTAACAGGTGCTAAAGTCAGAGC (SEQ ID NO: 33) | AAAGAAGGGGGTGGGGA (SEQ ID NO: 34) |
| PGK1 | 223 | 57.4 | 59.2 | CGTTATGAGAGTCGACTTCAATG (SEQ ID NO: 35) | AACATCCTTGCCCAGCAGA (SEQ ID NO: 36) |
| HSP90AB1 | 136 | 60.1 | 59.24 | CTCGTCGGGCTCCCTTTG (SEQ ID NO: 37) | ACCACACCACGGATAAAATTGAG (SEQ ID NO: 38) |
| LDHA | 114 | 60.0 | 59.5 | GCCCGAACTGCAAGTTGC (SEQ ID NO: 39) | CCAGATTGCAACCGCTTCC (SEQ ID NO: 40) |
| GAPDH | 172 | 60.3 | 59.9 | AAGGTGGTGAAGCAGGCG (SEQ ID NO: 41) | CGTTGTCATACCAGGAAATGAGC (SEQ ID NO: 42) |
| GUSB | 168 | 59.0 | 60.4 | TTGCAGGGTTTCACCAGGA (SEQ ID NO: 43) | GCACTCTCGTCGGTGACTG (SEQ ID NO: 44) |
| SDHA | 263 | 59.1 | 60.3 | TGGCACTGGGAAGGTCAC (SEQ ID NO: 45) | GGTTCCTGGCAAGCTCCC (SEQ ID NO: 46) |
| HPRT1 | 110 | 59.4 | 59.0 | TGCTTTCCTTGGTCAGGCA (SEQ ID NO: 47) | TTCAAATCCAACAAAGTCTGGCT (SEQ ID NO: 48) |
| ACTB | 142 | 59.7 | 59.5 | CAAGAGATGGCCACGGCT (SEQ ID NO: 49) | AGGACTCCATGCCCAGGA (SEQ ID NO: 50) |
| TERC | 173 | 60.1 | 59.8 | CTGCAGAGGTCGCTGGTC (SEQ ID NO: 51) | TCCACGAGCAGAATACAGCC (SEQ ID NO: 52) |
| RPLP0 | 137 | 59.9 | 59.8 | TGCCAGTGTCTGTCTGCAG (SEQ ID NO: 53) | AGGCCTTGACCTTTTCAGCA (SEQ ID NO: 54) |
| NONO | 187 | 60.2 | 58.9 | GCACAGCCTGGCTCCTTT (SEQ ID NO: 55) | GGCGCCTCATCAAATCCTG (SEQ ID NO: 56) |
| PPIA | 108 | 60.0 | 59.8 | AAAGCATACGGGTCCTGGC (SEQ ID NO: 57) | TGCTTGCCATCCAACCACT (SEQ ID NO: 58) |
| PPIH | 101 | 59.1 | 58.9 | TGGCCGCATGAAGATCGA (SEQ ID NO: 59) | TTGGAACCCCATCTTTCCTGA (SEQ ID NO: 60) |
| RPLP1 | 100 | 60.1 | 59.7 | CAATGTAGGGGCCGGTGG (SEQ ID NO: 61) | CACTTTCTTCTCCCTCAGCTGGA (SEQ ID NO: 62) |

TABLE 1-continued

PCR primers for reference amplicon experiments

| Gene Symbol | Len | Fwd $T_m$ | Rev $T_m$ | Forward Primer | Reverse Primer |
|---|---|---|---|---|---|
| B2M | 272 | 59.0 | 60.7 | TAGGCTCGTCCCAAAGGC (SEQ ID NO: 63) | GGTTCACACGGCAGGCAT (SEQ ID NO: 64) |

TABLE 2

PCR primers for isoforms in FIG. 4.

| Gene Symbol | Isoform | Len | Fwd $T_m$ | Rev $T_m$ | Forward Primer | Reverse Primer |
|---|---|---|---|---|---|---|
| WFDC2 | ENST00000462062 | 146 | 60 | 59.3 | TTGCTGGAGCTGCAGTCT (SEQ ID NO: 65) | GGAACCCTCCTTATCTTGGTTC (SEQ ID NO: 66) |
| RP11-3J1.1 | ENST00000505347 | 99 | 58.4 | 60.0 | ACACAATGTGTCCTAGAAGAAGA (SEQ ID NO: 67) | AGCTGCCCATTCGACTGT (SEQ ID NO: 68) |
| TMPRSS3 | ENST00000398405 | 77 | 59.8 | 59.4 | GCCCCCTTCTCATTCCGA (SEQ ID NO: 69) | GCAGCAACAGCATCTGGT (SEQ ID NO: 70) |
| CTD-2616J11 | ENST00000574814 | 169 | 60 | 59.8 | CTGGGCCTGAAGGGAACA (SEQ ID NO: 71) | AGGGTGTCCAGGCGTATG (SEQ ID NO: 72) |
| ETV4 | 1Aug10 | 200 | 59.9 | 60.7 | GGCGAGCAGTGCCTTTAC (SEQ ID NO: 73) | CGCACCCGGTGACATCTAT (SEQ ID NO: 74) |
| PRAME | gAug10 | 171 | 59.9 | 60.2 | GGCGTGAATGCGTGGATT (SEQ ID NO: 75) | TGCCACGCACGTGTTTTT (SEQ ID NO: 76) |
| huhare | fAug10 | 269 | 60.2 | 59.9 | GCCGTGGTGGTGTATTGC (SEQ ID NO: 77) | CACATCACTGGGCGTTCG (SEQ ID NO: 78) |
| SPC24 | ENST00000429831 | 106 | 59.8 | 60.1 | GCTGCTGGAAACGCAAGA (SEQ ID NO: 79) | CTGTCGCTCCTGCTCCTT (SEQ ID NO: 80) |
| PTH2R | ENST00000413482 | 174 | 60.0 | 60 | AGGTTCCTTGAACAGCTGGA (SEQ ID NO: 81) | CACTGTTCCTCTGGGCCA (SEQ ID NO: 82) |
| VTCN1 | ENST00000359008 | 284 | 59.1 | 60.0 | GCTGACCTCGCGCATAAT (SEQ ID NO: 83) | CTGTCCGGCCTCTGAACA (SEQ ID NO: 84) |
| SLC44A4 | ENST00000414427 | 114 | 60.1 | 59.9 | TCACTGTCGCCCAGAAGG (SEQ ID NO: 85) | CGCTGATCCCCTGCTGTA (SEQ ID NO: 86) |
| ESR1 | ENST00000456483 | 332 | 60.6 | 58.2 | CCGGCATTCTACAGGCCA (SEQ ID NO: 87) | TCCACAAAGCCACCTTTCA (SEQ ID NO: 88) |
| TNFRSF8 | ENST00000263932 | 121 | 59.8 | 59.9 | GCCTTCCCACAGGATCGA (SEQ ID NO: 89) | ACTGCTGTGTCGGGAACA (SEQ ID NO: 90) |
| VASN | HIT000304576 | 420 | 60.6 | 60 | CCTATCGGGCCCTGTTGG (SEQ ID NO: 91) | TGTAGGGCTTTGCGTGGA (SEQ ID NO: 92) |
| MYLPF | ENST00000563728 | 110 | 60 | 60.1 | ACCAGGAACCCAATCGCA (SEQ ID NO: 93) | GCCCACATGTTCTTGATCTCC (SEQ ID NO: 94) |

TABLE 2-continued

PCR primers for isoforms in FIG. 4.

| Gene Symbol | Isoform | Len | Fwd $T_m$ | Rev $T_m$ | Forward Primer | Reverse Primer |
|---|---|---|---|---|---|---|
| FOXM1 | lAug10 | 150 | 60.1 | 60 | CGGCCTCAAACC CAAACC (SEQ ID NO: 95) | GGCTCCTCAAC CACAGGT (SEQ ID NO: 96) |
| FOXM1 | ENST00000 536066 | 234 | 59.9 | 60.0 | GTCCCCCTGCTC CTGATC (SEQ ID NO: 97) | TCCCCTCCTCAG CTAGCA (SEQ ID NO: 98) |
| C19orf53 | ENST00000 588841 | 158 | 59.9 | 58.4 | CCCAAGAAAAG GCGGTAAGG (SEQ ID NO: 99) | ACTTCTAGGTTC TTCTTGAGCTT (SEQ ID NO: 100) |
| CD9 | iAug10 | 146 | 59.8 | 59.9 | GGGGTCAGCGG GACTTTA (SEQ ID NO: 101) | GCAAGGACAGC AATCCCG (SEQ ID NO: 102) |
| RAB11FIP4 | ENST00000 578694 | 94 | 59.8 | 59.8 | GCCTGGGAGGTC GTGTTA (SEQ ID NO: 103) | CATCAGCAAAG GTGGGGC (SEQ ID NO: 104) |
| CHODL | ENST00000 465099 | 96 | 59.0 | 60.2 | TGAGCCAATTCC CTGGAGA (SEQ ID NO: 105) | GAATCAACGTG CTGGCCC (SEQ ID NO: 106) |
| AURKA | sAug10 | 257 | 60 | 59.8 | ACTTGGGTCCTT GGGTCG (SEQ ID NO: 107) | TGCACTCCAGC CTCTAGC (SEQ ID NO: 108) |
| CDCA5 | ENST00000 529290 | 218 | 58.9 | 60,0 | GAACCTGCCCAC CTTATTGT (SEQ ID NO: 109) | GGTCACTGCAG GCAGAGA (SEQ ID NO: 110) |
| CDH24 | uc001wil | 167 | 59.2 | 60 | TACAGAGCTCGG CTGGAG (SEQ ID NO: 111) | TCTGGATGGCC ACTTGCA (SEQ ID NO: 112) |
| FGFRL1 | fAug10 | 428 | 60.2 | 60 | GCTCCTCTGGGG GTCAAG (SEQ ID NO: 113) | GCGGTTTTGGGT CTTGCA (SEQ ID NO: 114) |
| LSR | uc002nyp | 160 | 60 | 59.8 | CCTCAGGTGTTC CCAGCA (SEQ ID NO:115) | CCACTGCGGAC TGAGCTA (SEQ ID NO: 16) |
| SLC22A18 | ENST00000 312221 | 345 | 59.9 | 60 | GGCTGGAACTCA GACCCA (SEQ ID NO: 117) | TAGAGCGCTCA TCCTGCC (SEQ ID NO: 118) |
| STON2 | aAug10 | 222 | 60.8 | 59.7 | AACTCAGCTTCC GGTCACC (SEQ ID NO: 119) | TGTTTCTGTTGT CTGGTAGCTG (SEQ ID NO: 120) |
| SLC44A4 | pHIT00007 8073 | 112 | 59.9 | 59.5 | TACAGCAGGGG ATCAGCG (SEQ ID NO: 121) | TGTCCCACAGC CACAAGA (SEQ ID NO: 122) |
| OPN3 | hAug10 | 135 | 60.0 | 58.9 | TGCTGGTGTCCC TCTTCG (SEQ ID NO: 123) | TGCATTTGTGAC TGGAACTCT (SEQ ID NO: 124) |
| AC019117 | ENST00000 419463 | 69 | 59.3 | 60.1 | GGAACATCTACA CACAGAGGAAA (SEQ ID NO: 125) | GGGGACTGTTG GGAATGGA (SEQ ID NO: 126) |
| LINC00284 | ENST00000 439707 | 323 | 59.8 | 60.0 | TCAGAAGGCAA AGATTGACCAG (SEQ ID NO: 127) | TCCTGCTGAGCC AGGAAC (SEQ ID NO: 128) |
| MUC16 | HIT000048 730 | 108 | 59.8 | 59.9 | ACCCATCGGAGC TCTGTG (SEQ ID NO: 129) | GGAACAGTTAC TTGTGGGGC (SEQ ID NO: 130) |
| TFRC | Multiple (Ref) | 173 | 60.1 | 59.8 | CTGCAGAGGTCG CTGGTC (SEQ ID NO:131) | TCCACGAGCAG AATACAGCC (SEQ ID NO: 132) |

TABLE 2-continued

PCR primers for isoforms in FIG. 4.

| Gene Symbol | Isoform | Len | Fwd $T_m$ | Rev $T_m$ | Forward Primer | Reverse Primer |
|---|---|---|---|---|---|---|
| RBM17 | Multiple (Ref) | 127 | 59.9 | 60.1 | ACATGGTTGGTG CGGGAG (SEQ ID NO: 133) | ACTGCTTCATCA TCAGGGGC (SEQ ID NO: 134) |
| PPIA | Multiple (Ref) | 108 | 60.0 | 59.8 | AAAGCATACGG GTCCTGGC (SEQ ID NO: 135) | TGCTTGCCATCC AACCACT (SEQ ID NO: 136) |

Relative Quantification.

A software implementation of the qBase relative quantification framework (Hellemans et al., 2007) was used to calculate all normalized relative quantities in this study. In accordance with MIQE guidelines (Bustin et al., 2009), computed reaction efficiencies and three reference amplicons (discussed above) were included in the calculations.

Total RNA and cDNA

All normal tissue total RNA was purchased from Biochain. Tumor total RNA was either purchased from Origene or derived from frozen tumor samples obtained from UC San Diego Moores Cancer Center Biorepository. RNA was extracted manually from frozen tumor tissue samples (approx. 25 mg) using Qiagen RNeasy (Cat #74104) kit as described by manufacturer. 1 ug of RNA as determined by a Nanodrop 1000 (Thermo Scientific) was converted to cDNA using the SuperScript III Reverse Transcriptase Kit (Cat #180800051 Life Technologies) with random hexamers priming as described by the manufacturer. Final cDNA was diluted to the equivalent of 10 ng/uL starting RNA concentration. For normal tissue, cDNA from each tissue type was pooled at equal concentrations to minimize reaction efficiency variation.

Results

The overall strategy of the tumor-specific isoform identification process (FIGS. 4-5) is based on: 1) computational algorithms custom developed for sensitive and accurate isoform identification; 2) large compendiums of tumor and normal tissue RNA-seq data produced by TCGA and GTEx; and 3) high-throughput RTqPCR experiments. As reported below, custom algorithms were used to efficiently process large amounts of RNA-seq data and applied one prioritization strategy to produce a list of mRNA isoforms rank prioritized by likelihood of being tumor-specific. Then custom developed software was used for automated design of isoform-specific PCR primers and performed RT-qPCR using pooled tumor RNA and pooled normal tissue RNA. For isoforms found to only be present in the tumor pool, their expression by RT-qPCR was measured in a larger set of non-pooled tumor and normal samples. The isoforms that were expressed across multiple tumors were then ranked based on whether they were expressed in zero, one, two, three, four or more normal tissues and evaluated for oncologic applications.

Computational Pipeline for RNA-Seq.

The standard RNA-seq computational pipeline for organisms with a sequenced genome has three main components (FIG. 1A): 1) alignments of RNAseq reads to the genome, 2) an isoform model database, and 3) an integration algorithm, whose input is the isoform model database and the read pair alignments and whose output is the expression level of the supplied isoforms. A pipeline was developed for isoform identification and expression level estimation that is distinguished by novel methodologies and custom software algorithms in each of these three components.

Figure 6:
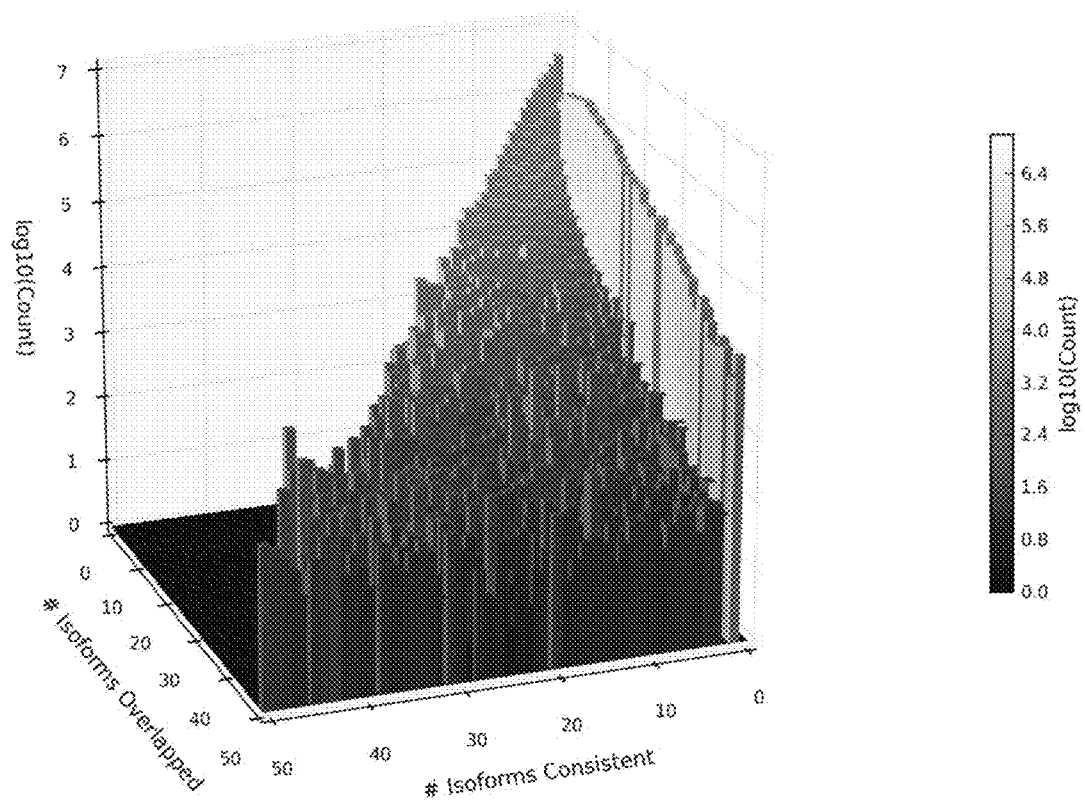
FIG. 6. Effect of read-to-isoform verification. RNA-seq read pair alignments often overlap isoforms from which they both could and could not have been physically derived. Nucleotide-level correspondence analysis was performed to explicitly associate each read pair with a specific isoform or set of isoforms from which it could have been derived. As shown, this procedure markedly reduces the number of isoforms with which read pairs can be associated.

A major distinguishing feature of our approach to RNA-seq read alignment is the use of maximally sensitive alignment parameterizations coupled with nucleotide-resolution read-to-isoform correspondence verification. Such parameterizations enable the thorough detection of all RNA-seq read alignments spanning splice junctions, which are especially informative because they provide exon linkage information that can be crucial for accurate isoform identification. Current practice sets "minimum overhangs" of a read's alignment over a splice junction into an adjoining exon—often 8 bp or more—to guard against false genomic alignments. To maximally recover the information in RNA-seq reads, alignments were considered with even 1 bp overhangs, but then through nucleotide-resolution read-to-isoform correspondence verification we reject all read pair alignments that do not exactly match the human genome reference sequence. This approach has four consequences (see FIG. 1B). First, isoform identification information was maximized in each set of RNA-seq data. Second, read pairs were identified that do not correspond to any known isoform and prevent their subsequent use for isoform expression estimation. In practice, these rejected read pairs constitute 2-3% of the raw data and are indicative of the presence of isoforms that have not been discovered and incorporated into any public database (Mercer et al., 2012). Third, each read pair was explicitly associated with a specific isoform or set of isoforms from which it could have been derived and then use this information in the final expression estimation stage. Due to the high overlap of isoforms at a genomic locus, read pair alignments often overlap isoforms from which they both could and could not have been physically derived. In some RNA-seq computational protocols, this distinction is not addressed and read pair alignments are erroneously used to estimate the expression of isoforms from which they could not have been physically derived. As shown in FIG. 6 for an exemplar RNA-seq data set, read-to-isoform correspondence verification markedly reduces the number of isoforms with which read pairs can be associated. And fourth, read pairs were explicitly associated to isoforms to enable the strategy for minimizing both false positives and false negatives in RNA-seq experiments (see below).

Figure 2:
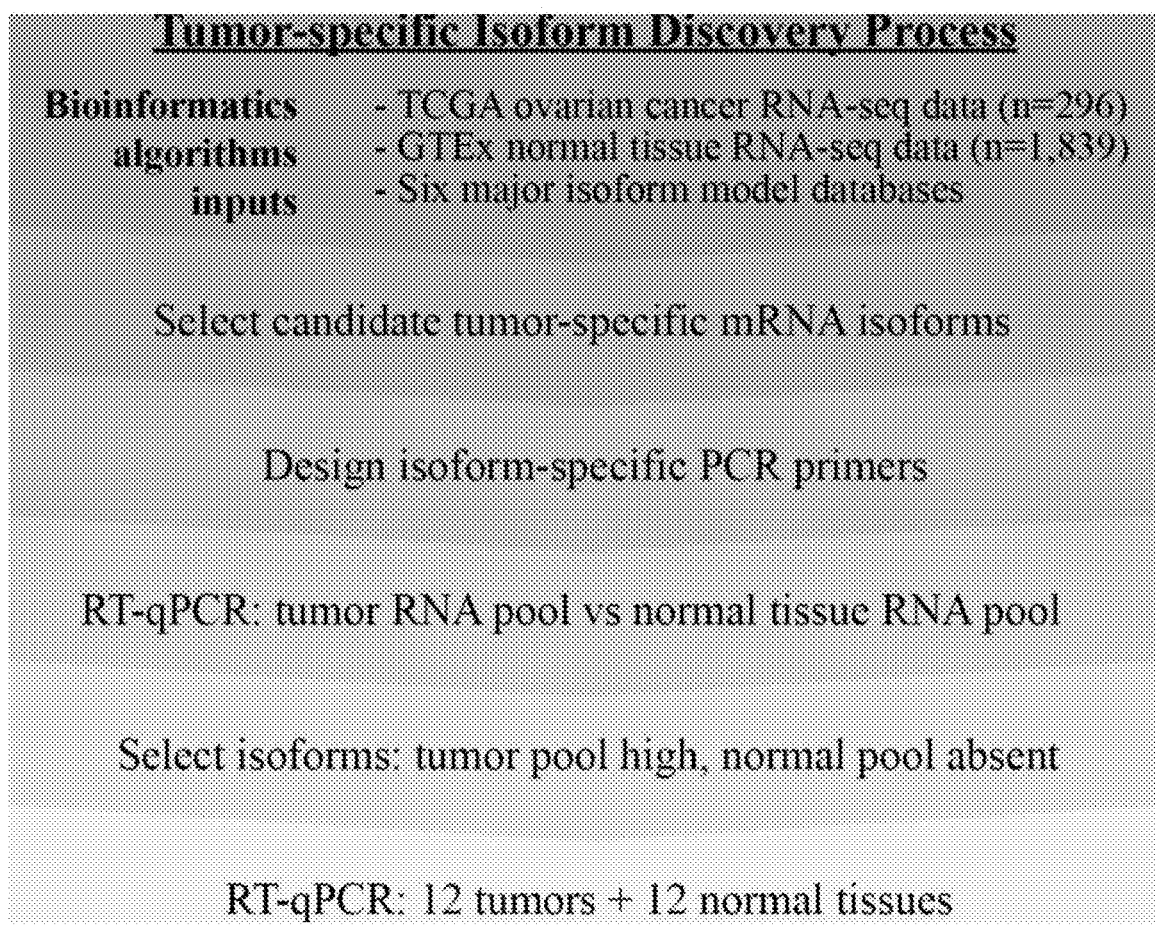
FIG. 2. Discovery process overview. Bioinformatics algorithms to large public compendiums of tumor and normal tissue RNA-seq data to rank prioritize mRNA isoforms by likelihood of being tumor-specific. RT-qPCR was then used in two phases to confirm tumor-specific expression. First we performed RT-qPCR to analyze the RNA of six tumors pooled together versus the RNA of six normal tissues pooled together. Then the most likely tumor-specific isoforms were selected based on expression profiles in these two pools. Final validation was RT-qPCR on individual tumor and normal tissues.
Figure 3:
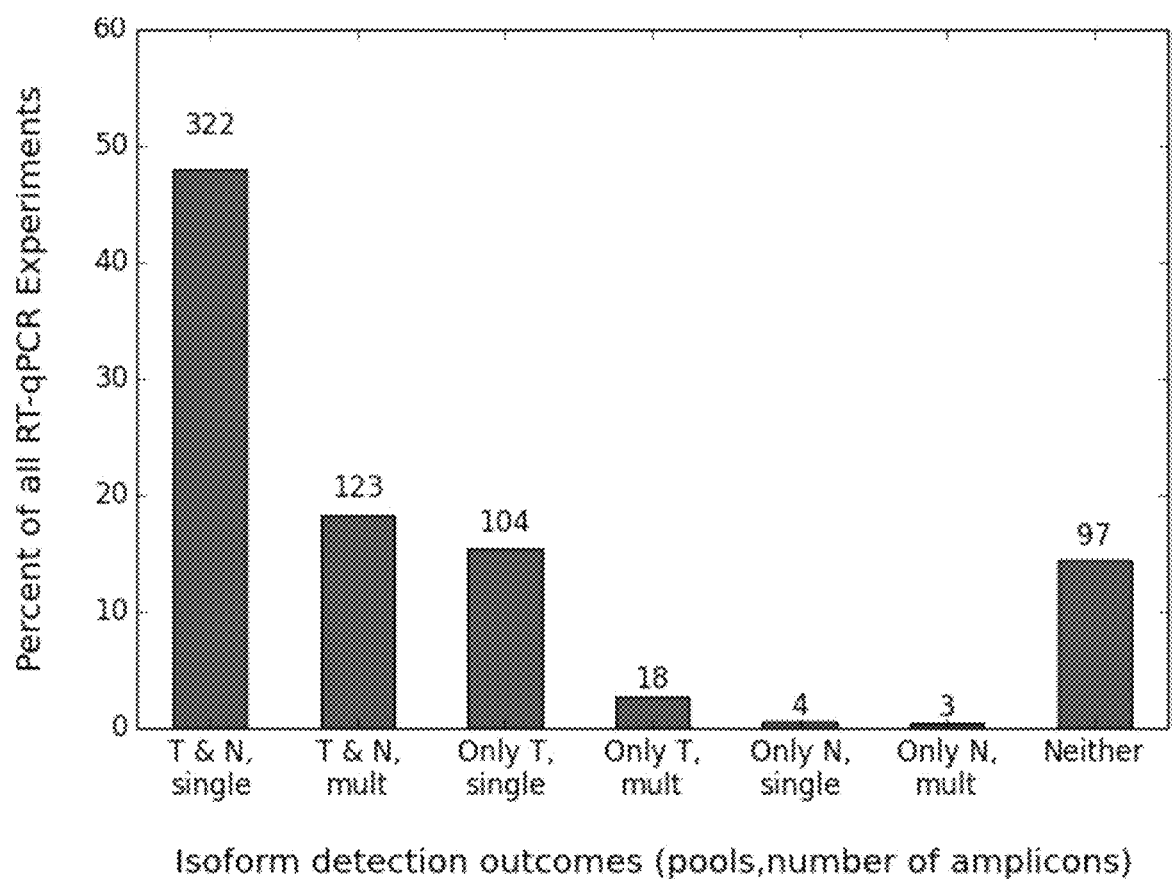
FIG. 3. Categories of pooled RNA RT-qPCR experiments. For isoform candidates derived from RNA-seq-based analyses, we measured their expression by RT-qPCR in a pool of tumor (T) RNA samples and pool of normal tissue (N) RNA samples. The expression status of the isoforms in aggregate spanned all possible outcomes. By melt curve analysis, instances in which just the target product (single) was amplified and instances in which multiple products (mult) were amplified—indicative of the presence of novel mRNA isoform structures were observed. Number of isoforms in each category is displayed atop each bar.
Figure 7:
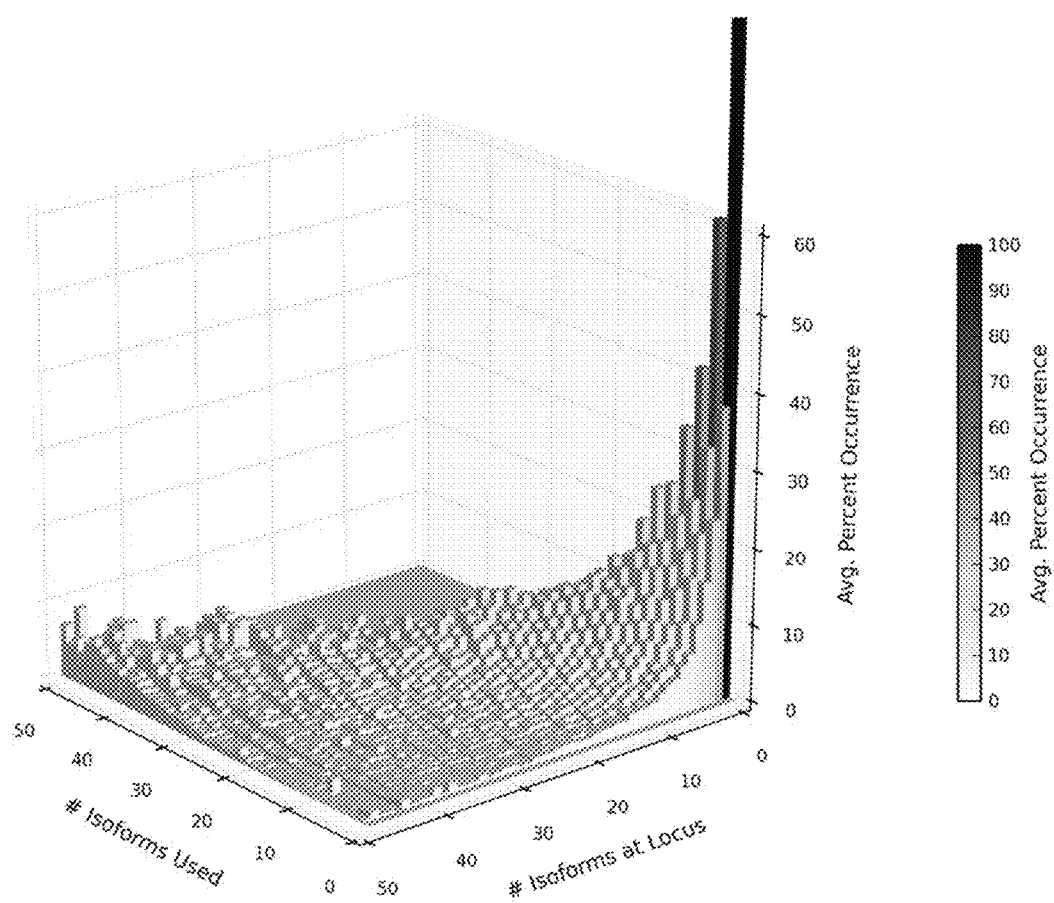
FIG. 7. Average Isoform Use at Loci. As part of the computational RNA-seq pipeline a parsimony principle was applied to identify the isoforms that can most succinctly account for the RNA-seq reads aligned at a genomic locus. The effect of this procedure is to significantly reduce the number of isoforms models that are supplied to an integration algorithm that estimate isoform expression levels from aligned RNA-seq data. (For visual clarity, only loci with 50 or fewer isoforms are shown here.)

A major distinguishing feature of this approach to isoform models is the use of a custom isoform model database that was created by merging all of the major isoform model databases (see FIG. 1C). Although the use of only one particular isoform model database is standard in current RNA-seq computational protocols, doing so is a source of false negatives (Wu et al., 2013), if a particular isoform is not in the database, then the integration algorithm (see FIG. 2A) cannot know about it and use it for expression estimation. By merging all major isoform model databases, the present approach minimizes the possibility of such false negatives. Conversely, isoforms in a supplied isoform model database that are not actually expressed in a sample from which RNA-seq data was generated represent noise for the integration algorithm and can lead to the assignment of non-zero expression for unexpressed isoforms. To minimize the possibility of such false positives, the read-to-isoform verification information discussed above and the implementation of a greedy solution to the Set Cover Problem (Chvatal, 1979) was used to identify the set of isoforms that most parsimoniously explains the RNA-seq read alignments. In effect, an isoform model database is created that is tailored to each RNA-seq experiment. As shown in FIG. 7, this tailoring reduces the number of isoforms from loci that are used as input to the integration algorithm.

Tumor-Specific Isoform Predictions from 2,135 RNA-Seq Experiments.

Figure 8:
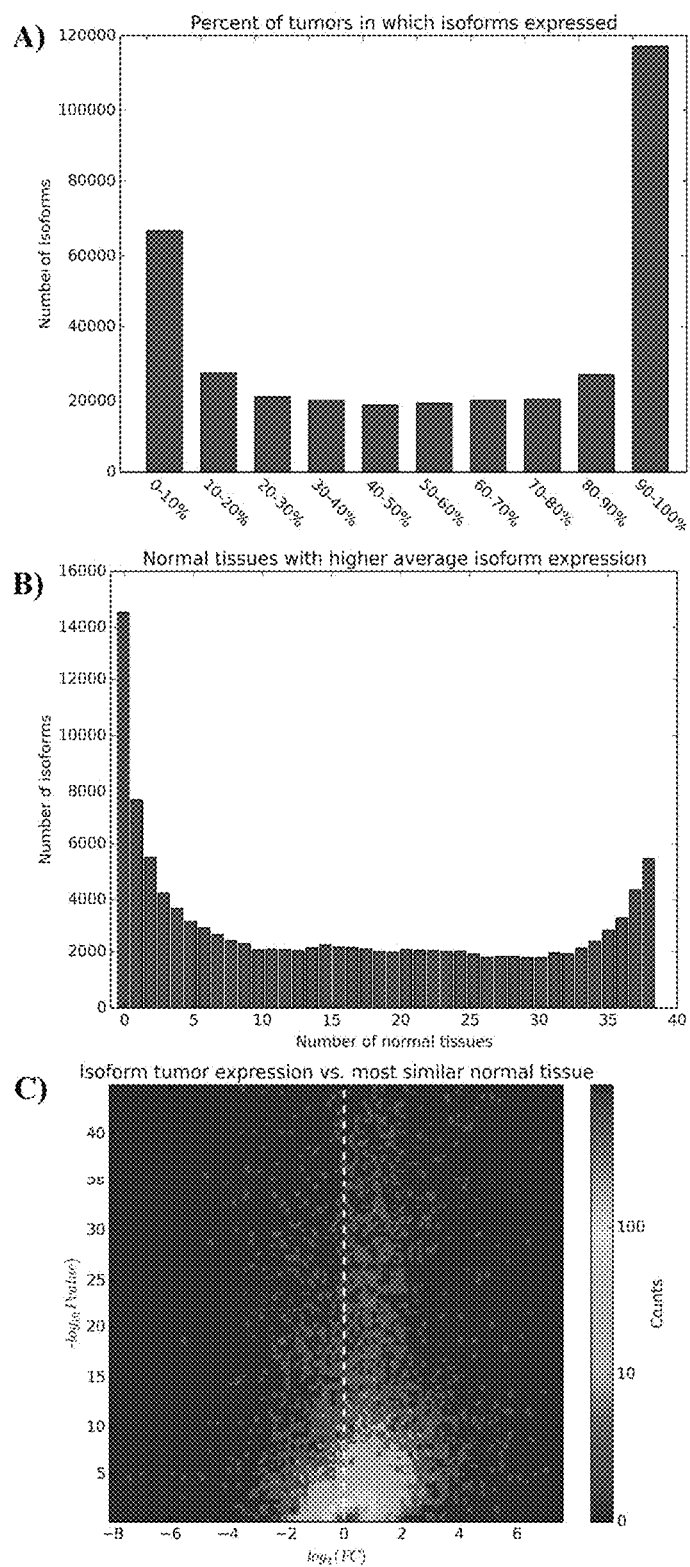
FIGS. 8A-C. Use of RNA-seq to identify the isoforms most likely to be specifically expressed in HGS-OvCa. A) Using a liberal expression value cutoff to deem an isoform "expressed", isoforms that expressed in 90-100% of all 296 HGS-OvCa tumors samples were identified. B) Then those (22,082) isoforms whose average expression was higher in zero or one normal tissue compared to tumor were identified. C) For each isoform the normal tissue in which its expression was most similar to ovarian tumor expression was identified. The fold change of average expression and the Mann-Whitney p-value were computed. The isoforms from B) were sorted by these two statistics to rank prioritize isoforms by likelihood of being tumor-specifically expressed.

For the present study mRNA isoforms that are the most pervasively and exclusively expressed in HGS-OvCa were sought. Using 296 curated TCGA RNA-seq data sets for HGS-OvCa, isoforms expressed in 90-100% of tumors were first identified. In order to capture even very lowly expressed transcripts, an expression level cutoff of $10^{-6}$ FPKM was used to define whether a transcript was expressed or not. This first filter yielded 117,108 isoforms (see FIG. 8A). The 1,839 GTEx RNA-seq data sets were used to count the number of normal tissues in which the average expression of each of these 117,108 isoforms was equal or higher. As shown in FIG. 8B, most of the isoforms expressed in 90-100% of the TCGA ovarian tumors were also expressed in many normal tissues. For each of the 22,082 isoforms that was equally or more highly expressed in at most one other tissue, the normal tissue with the highest average expression was identified and computed two statistics: 1) the Mann-Whitney P-value associated with the two sets of expression values (i.e., tumor vs normal); and 2) the fold change of the average tumor expression over the average normal tissue expression. As shown by FIG. 8C, most of the 22,082 isoforms were not appreciably distinguished in their tumor expression from their "closest" normal tissue expression by average expression fold change nor the distribution of expression values. Finally, the 22,082 isoforms were rank prioritized by likelihood of being tumor-specific by sorting them by fold change and P-value.

High-Throughput mRNA Isoform-Specific PCR Primer Design.

The sequencing technology upon which this study is based has the limitation of only being applicable to about 200-250 bp fragments of cDNA-restricting its ability to unambiguously identify mRNA isoforms that in the human genome are on average about 2 kb. For this reason RT-qPCR was used to confirm the tumor-specific expression of mRNA isoforms that were rank prioritized by RNA-seq. To enable a large number of RT-qPCR experiments, software was developed that could exhaustively identify and design primers for all unique amplicons of any target mRNA in the human genome. With this software design primers were designed for the 1,230 topmost tumor-specific candidate mRNA isoforms. Of these attempts, 671 (54.6%) were successful. Of the unsuccessful attempts, 320 (26.0%) were due to the lack of a unique amplicon sequence in the target isoform and 239 (19.4%) were due to primer design failure. (Primer design failure can occur for reasons related to $T_m$ requirements, forward and reverse primer compatibility, primer or amplicon sequence length constraints, and primer amplification of unintended products.)

Confirmation of Isoform Tumor-Specific Expression by RTqPCR.

Figure 9:
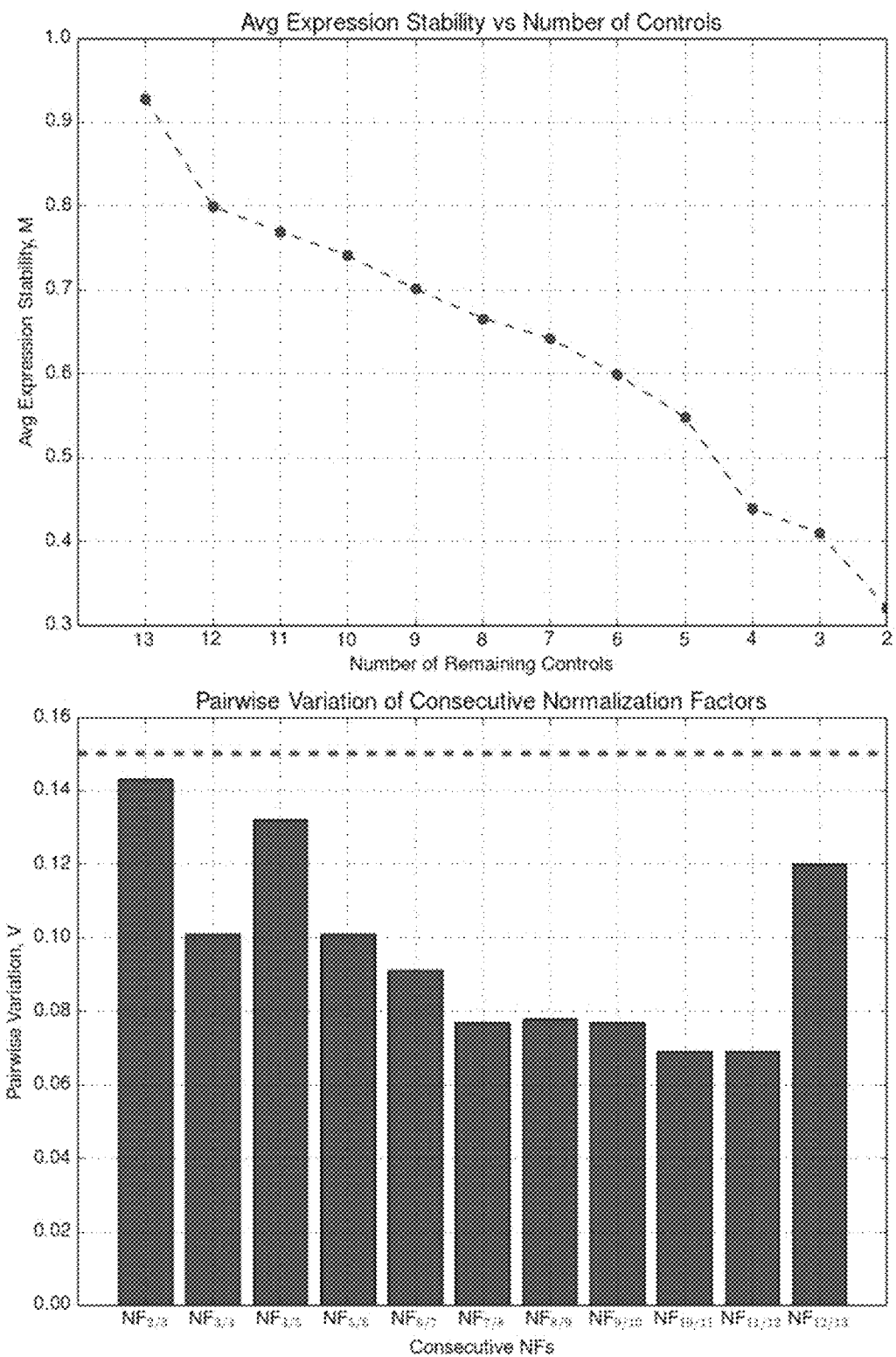
FIG. 9. geNorm output. qPCR results for 32 candidate reference amplicons in 6 tumor and normal tissues were used as input to geNorm. For readability the geNorm output for the 13 most stable references were shown. The red line in the bottom panel marks geNorm's standard acceptability cutoff of 0.15.

Confirmatory RT-qPCR experiments were performed using a two-phase approach. In phase 1 pooled RNA was used to efficiently filter out isoforms that were not expressed in tumors and/or were expressed in normal tissues. A pool of 4 different tumor RNA samples and a pool of 4 different normal tissue RNA samples were used and then measured the expression of all 671 isoforms in both pools. As graphed in FIG. 9, 66.2% (n=445) of isoforms were present in both pools, 18.2% (n=122) were present only in the tumor pool, 1.0% (n=7) were present only in the normal pool, and 14.5% (n=97) were absent in both pools. Furthermore, the experiments revealed the presence of novel isoforms that are not documented in any of the isoform model databases that were used to construct the isoform model database. In the group of isoforms found in both pools, 18.3% of reactions revealed one or two additional products. For the "tumor only" and "normal only" groups, the percentages were 5.7% and 0.4%, respectively.

In phase 2 the expression of a subset of the isoforms in an expanded set of individual, non-pooled, RNA samples was measured. For the subset 86 isoforms were selected that were absent from the normal tissue pool, that were associated with a single peak melt curve, and that were the most robustly expressed in the tumor pool. To expand the set of RNA samples an additional 8 tumor samples and an additional 8 normal tissue samples—for a total of 12 tumor samples and 12 normal tissue samples were added. RT-qPCR was used to measure the expression of the 86 isoforms in the 24 individual samples and then ranked the isoforms by the number of normal tissues in which they were expressed. The top-ranked 33 isoforms, shown in FIG. 4, constitute 5% of the original 671 isoforms investigated. The top 8 isoforms, or 1.2% of the original 671, were expressed in 6-12 of the 12 tumors and were undetectable in all 12 normal tissues examined. An additional 11 isoforms (1.6% of 671) were only observed in one normal tissue, which in most cases was either fallopian tube or colon. In the remaining 14 cases (2.1% of 671) in which the isoforms were present in 2, 3, or 4 normal tissues, fallopian tube and/or ovary were most consistently among the normal tissues. Biologic basis and applications of candidate tumor-specific molecules. Because the mRNA isoforms in FIG. 4 are expressed in 6-12 of the 12 different tumors and have highly restricted or undetected normal tissue expression, they are of immediate and high interest for both understanding tumor biology and for oncologic applications. A complication that arises when interpreting isoform-level findings is that most isoforms of most genes have not been explicitly studied, and even small differences in mRNA or protein isoform primary sequence from a well-studied canonical isoform can alter the molecule's function, localization, lifetime, structure, and/or interaction network (Weatheritt et al., 2012). Nonetheless, with this caveat in mind, below isoforms that are likely to play a causative functional role in the malignant state and that have potential use for diagnosis and therapy are highlighted.

Isoforms of Genes Related to Oncogenesis, Stem Cells, and Stem Cell-Like Cancer Cells.

A structurally distinct mRNA isoform 1Aug10 of ETV4/PEA3 (see FIG. 4) was expressed in all studied tumors and was detectable only in normal heart. ETV4 is a transcription factor that is active in developing embryos and adult tissues and that has a demonstrated transforming role in Ewings tumors, prostate, ovarian, breast and other solid tumors (Oh et al., 2012). The 1Aug10 isoform is incompletely known at the 3' end, but enough of the transcript has been sequenced to reveal that 1Aug10 is the only ETV4 isoform with a truncated N-terminal amino acid sequence and a skipped exon 5. The functional implications of this distinguishing structure are unknown.

FOXM1 is a transcription factor that is both a potent oncogene and an important molecule for maintaining stem cell renewal (Teh, 2012). The gene is highly expressed across a broad range of different solid tumor types, including ovarian cancer. Integrated genomic analyses of ovarian cancer performed by TCGA found the FOXM1 regulatory network to be the most significantly altered in expression level across 87%/o of the 489 tumors studied. FOXM1 has multiple isoforms, two of which have been studied for their transforming potential (Lam et al., 2013). This study found that isoforms FOXM1b and FOXM1c both had transforming potential, and that FOXM1c was likely to be constitutively active because it was proteolytically processed to yield short isoforms without the N-terminal inhibitory domain. The 1Aug10 and gAug10/ENST00000536066 isoforms that are in FIG. 4 were neither of the isoforms studied, but interestingly, both are short isoforms that are missing the N-terminal inhibitory domain. Thus it may be that one or both of the FOXM1 isoforms that we identified are constitutively active transforming isoforms of FOXM1.

Tetraspanin proteins are increasingly viewed as therapeutic targets because of their emerging key roles in tumor initiation, progression, metastasis, and sometimes angiogenesis (Hemler, 2013). An isoform iAug10 of CD9/tetraspanin-29 was identified that was expressed in 10 of 12 tumors and absent from all but one normal non-gynecological tissue. CD9 is a cell surface marker for normal human embryonic stem cells and for cancer stem cells in non-small-cell lung carcinoma (Zhao et al., 2012). It has various anti- and pro-tumorigenic roles, with the latter including that of an oncogene in an ovarian cancer line (Hwang et al., 2012). The varied and opposing roles of CD9 have been suggested to be a consequence of its different interaction partners in the plasma membrane (Hemler, 2013). An additional and compatible reason, though, may be the multiple protein isoforms of CD9.

The lipolysis-stimulated lipoprotein receptor (LSR) is a gene that in basal-like triple-negative breast cancer cell lines is a biomarker of cells with cancer stem cell features and with a direct role in driving aggressive tumor initiating cell behavior (Leth-Larsen et al., 2012; Reaves et al., 2014). These observations are relevant to the present study because of the discovery that basal-like breast cancers and ovarian serous cancers exhibit very similar mRNA expression programs and share critical genomic alterations indicating related etiology and therapeutic opportunities. At the gene level LSR is transcribed in multiple normal tissues, but our investigation revealed LSR isoform uc002nyp.3 to be expressed across all 12 tumors studied and undetectable in all 12 normal tissues studied. Intriguingly, because of this isoform's structure (see FIG. 5D) it has dual therapeutic potential; its splice junction forms a unique amino acid sequence that is a predicted extracellular epitope and is computed to have a high binding affinity for three different MHC I alleles. Thus, this isoform has the potential of encoding a protein with one tumor-specific polypeptide that is both an antibody and T-cell target on ovarian cancer stem cells and that, if found to be expressed in breast basal-like tumors, could be relevant for multiple difficult tumor types.

Isoforms for Early Detection and Monitoring of HGS-OvCa.

The Papanicolaou test has recently been demonstrated to be a viable source of ovarian tumor cells (Kinde et al., 2013). This observation allows the possibility for an early ovarian cancer detection test based on the assessment of ovarian tumor-specific mRNA isoforms that are expressed in tumor cells that have disseminated to the cervix. For such an early detection strategy to work, one would need to identify mRNA isoforms that are only expressed in ovarian tumors and not in normal gynecologic tissues. Extensive experimental evidence (Lee et al., 2007; O'Shannessy et al., 2013; Kim et al., 2012; Kessler et al., 2013) indicates that fallopian tube, and to a lesser extent the ovary, are the tissue(s) of origin of HGSOvCa. Additionally, many studies (Marquez et al., 2005; Sproul et al., 2012: Ge et al., 2005) have demonstrated that expression profiles of tumors are more similar to those of their tissue of origin than to any other normal tissue, so for HGSOvCa fallopian tube and ovary are the most stringent tissues against which to judge the tumor-specificity of an mRNA isoform. As shown in FIG. 4, we found 2.8% (n=19) of the original starting set of 671 isoforms were not expressed in the ovary or fallopian tube and that 1.2% (n=8) of isoforms were not expressed in any of the normal tissues tested. These findings constitute an initial candidate set of mRNA isoforms upon which a new strategy for the early detection of ovarian can be developed.

Isoforms Predicted to Encode Cell Surface Targets.

The parathyroid hormone receptor 2 gene PTH2R encodes a class B (type II) GPCR that is predominantly expressed in endocrine and limbic regions of the forebrain and to a lesser extent in restricted cell types of peripheral tissues (Dobolyi et al., 2012). Its function in non-brain tissues and in cancer has not been studied. The mRNA isoform that we identified is highly expressed in 10 of the 12 tumors used herein (see FIG. 4). The isoform is distinguished by its alternative first exon, which is predicted to retain a (likely cleaved) signal peptide (see FIG. 5A). In addition to the signal peptide, the first exon would confer on the protein isoform a unique 12 amino acid sequence. Since the protein is a class B GPCR, its N-terminal sequence is expected to be extracellular and thus amenable to antibody targeting.

The CD9 isoform identified herein, which was expressed in 100% of the late stage 296 TCGA tumors and in 10 of the 12 tumors (see FIG. 4), contains a unique exon (see FIG. 5B) that imparts upon the protein a unique, in-frame 41 amino acid sequence that encompasses the first two transmembrane regions of the protein and the extracellular domain between them-making it amenable to specific antibody targeting if expressed.

Isoforms Predicted to Encode Epitopes for Tumor Vaccines.

While the C-terminal portion of the tumor-specific ETV4 isoform identified herein is incompletely known, the portion that is known reveals the isoform to have an exon-skipping event that is unique among all ETV4 isoforms—conferring on the resulting protein at least 14 unique amino acids (see FIG. 5C). The epitope potential of this region was analyzed using a computational method (Nielsen et al., 2007) that has been recently validated by retrospective prediction against a large set of bona fide T-cell antigens that induced immune responses and were associated with tumor regression and long-term disease stability (Fritsch et al, 2014). A 10-mer epitope centered directly over the unique splice junction was identified and calculated to have a very strong affinity (12.9 nM) for the HLA allele A*02:01 and a moderate affinity (363 nM) for the B*08:01 allele. Because the A*02:01 and B*08:01 alleles are among the most common HLA alleles in the Caucasian population of the United States (Gonzalez-Galarza et al., 2011), the ETV4 isoform is a strong candidate for immunotherapeutic application for ovarian cancer.

Discussion

A highly customized RNA-seq bioinformatics pipeline was developed that is designed for isoform identification and that is distinct from standard approaches because of: 1) its use of an isoform model database that is a merger of all isoform model databases available worldwide: 2) its capability for maximally sensitive genome-wide read alignment; and 3) the nucleotide resolution consistency analysis that is performed for every sequencing read-isoform combination. Furthermore, a workflow for high-throughput, isoform-level RT-qPCR experiments was developed that is distinguished by software for automated design of PCR primers that are specific to individual mRNA isoforms at complex genomic loci (i.e., loci in which no isoform may even have a uniquely distinguishing splice junction or exon). A combined computational/experimental pipeline was used to generate detailed molecular hypotheses in the form of specific molecules (i.e., mRNA isoforms and/or the protein isoforms that they encode) with ovarian tumor-specific expression and with particular oncologic application(s). Importantly, the hypotheses were based on gene-level analyses that by definition encompass numerous mRNA and protein isoforms in aggregate. Based on the RNA-seq-based rank prioritization of mRNA isoforms, identify, at a rate of about 3%, mRNA isoforms were identified that have the tumor specificity required for an early detection diagnostic and/or that encode protein isoforms with unique epitopes amenable for monoclonal antibody targeting, vaccines, and adoptive immunotherapies.

Analogous to the challenge of distinguishing driver from passenger mutations in cancer genomics (Reva et al., 2011), cancer transcriptomics must contend with the challenge of distinguishing those mRNA molecules that are important for the malignant phenotype from those that are not. This challenge was addressed by requiring the mRNA isoforms interrogated in the present study to be expressed in 90-100% of the TCGA ovarian tumors, with the rationale being that a tumor-specific isoform that is present in 90-100% of tumors is less likely to be so as a deregulation side effect but because it is functionally important. In support of this rationale, among the topmost 5% (n=33) tumor-specific isoforms are variants of genes that are demonstrated oncogenes, known to maintain the malignant state, have a direct role in driving aggressive tumor initiating cell behavior, or are necessary for maintaining a stem cell phenotype. In addition to the cancer genomics goal of identifying driver mutations is the goal of identifying driver mutations that are "actionable". Among the topmost 5% are at least five protein targets that have unique primary structures that would allow them to be specifically targeted for one or more therapeutic strategies, including monoclonal antibody therapy/chimeric T-cell generation, and peptide- or T-cell-based vaccines.

Beyond protein, mRNA itself has the potential to be a therapeutic target (Zangi et al., 2013; Zhou et al., 2013). If proven to be so, mRNA has a great advantage over protein as a class of target molecule because MHC epitope and cell surface restrictions would not apply. But like protein therapeutics, mRNA would need to be targeted isoform-specifically because of the high degree of identical nucleotide sequence among the isoforms from a genomic locus. This study is pertinent to mRNA therapeutics because it demonstrates a feasible strategy for finding tumor-specific mRNA targets. Herein the idea is proposed—inspired by a DNA-based approach (Kinde et al., 2013)—of an ovarian cancer detection test based on the detection of tumor-specific mRNA isoforms from malignant cells that have disseminated to the cervix and been collected during a Papanicolaou test. A strategy based on RNA and not DNA could have distinct advantages. Tumor types have characteristic expression profiles that are distinctive from both those of other tumor types and normal tissues. An approach based on RNAs that are broadly indicative of characteristic expression programs could be more robust because it would not rely on particular mutations but on a characteristic cancer cell expression phenotype. Furthermore, because somatic DNA mutations occur in one or a few copies per tumor cell and RNA isoforms can occur in 100's-1,000's of copies per cell, an assay based on mRNA is potentially much more sensitive. The first requirement for such a test is the enumeration of mRNA molecules that indicate the presence of an ovarian tumor. In our experiments, we identified isoforms that were expressed in most or all tumors and were not detected in any normal tissues. Furthermore, additional isoforms were identified that were expressed in most or all tumors and in only one normal tissue that, importantly, was not ovary or fallopian tube. These additional isoforms are also candidates for a detection test because, not being found in the gynecologic tissues tested, would be indicative of tumor cells if detected in a Papanicolaou test.

There are a number of hard limitations to the approach for tumor-specific isoform identification and validation. These hard limitations are due to the "short read" nature of RNA-seq data and to the great extent to which mRNA isoforms at a genomic locus share exons and splice junctions. RNA-seq reads represent, essentially, 200-250 contiguous basepairs of processed mRNA. As most mRNAs are much longer than 250 bps, RNA-seq reads cannot provide the information that links distant exons and that is often necessary for unambiguous identification of the source mRNA isoform. The present RNA-seq computational procedure was designed for maximum accuracy in identifying those isoforms that were, and were not, represented in an RNA-seq data set. To achieve this goal, false negatives were minimized by merging all of the major isoform model databases and then nucleotide-level correspondence and parsimony algorithms were developed to minimize false positives. Nonetheless, determining which isoforms generated a set of RNA-seq reads is an inference problem that will always be error prone and because of this no isoform identification procedure will be completely accurate. However, even if one was able to identify the mRNA isoforms underlying an RNA-seq data set with complete accuracy, there is a limitation on the rate at which their expression can be confirmed by PCR. To confirm an mRNA isoform one must design PCR primers that amplify a uniquely distinguishing nucleotide sequence. At complex genomic loci this is a challenging task because of the extent to which exons and splice junctions are shared among isoforms. A major component of the present study is the algorithms that were developed for automated design of isoform-specific PCR primers. Even with the software primers could only be designed for about 55% of isoforms, meaning that almost half of the isoforms that we predicted by RNA-seq to be tumor-specific could not be investigated by RTqPCR. Furthermore, for about 25% of the isoforms for which primers could be designed, melt curve analysis revealed the presence of multiple PCR products (often 2 or 3)—indicating the presence of new isoforms. These observations are compatible with recent transcriptome sequencing experiments that have reported on new isoform discovery rates (Mercer et al., 2012: Lin et al., 2012; Howald et al., 2012). That RT-qPCR discovers isoforms at a higher rate attests to its higher sensitivity and lack of library preparation procedures.

As opposed to the limitations that exist for the present approach, there are three "soft" limitations that could be readily addressed to potentially improve our tumor-specific isoform identification rate. First, only two metrics were used to rank prioritize isoforms by likelihood of being tumor-specific. The output of the RNA-seq computational procedures has six metrics. Additionally, the present procedures have three threshold values that have not been optimized. The use of more or other metrics for rank prioritization and of optimized threshold values likely will yield additional results of the same qualitative nature as reported herein. Second, ovary and fallopian tube were the most common normal tissues in which isoforms were expressed (see FIG. 4). As the tissue of origin and primary tumor site, these are exactly the normal tissues in which a tumor-expressed isoform is most likely to be expressed. Unfortunately, these are also exactly the normal tissues for which we had the fewest normal control RNA-seq data sets (3 ovary and 1 fallopian tube). Thus the ability to negatively filter tumor-expressed isoforms was limited. The GTEx project is actively sequencing ovary and fallopian tube, so this soft limitation will diminish in the future. Third, the known expression subtypes of HGS-OvCa (TCGA, 2011; Tothill et al., 2008; Verhaak et al., 2013) was not accounted for, but instead mRNA isoforms were sought that were expressed in all tumor subtypes (i.e., 90-100% of the 296 TCGA tumors). Incorporating subtype classification into the procedures could yield tumor subtype-specific mRNA isoforms.

Tumor cells that disseminate to the cervix or into the bloodstream may down regulate the isoforms that are expressed in primary tumors, so for utility in a Papanicolaou test-based early detection diagnostic or in identifying circulating tumor cells the continued expression of isoforms in these non-primary tumor sites will need to be confirmed. Additionally, mRNA expression does not always equate to protein expression, so for the protein isoforms with therapeutic target potential their expression and cellular localization in tumor cells will need to be experimentally confirmed.

In summary, a systematic process was developed for identifying tumor-specific mRNA isoforms that leverages the large and growing public compendiums of tumor and normal tissue RNA-seq data. The rate at which tumor-specific isoforms can be identified for HGS-OvCa was quantified and it was demonstrated that they have the potential to provide the specificity needed for extremely specific diagnostics and therapeutics. The present findings are relevant in a larger context because the procedures developed can be readily and rapidly applied to any of the 30 or more tumor types for which large amounts of RNA-seq data now exist.

Example 2

The intention is for the appropriate tissue sample to be the human tissue cells that are already collected during routine gynecological procedures (e.g., Pap smears or endometrial biopsy), and for the isoform detection technology to be RT-qPCR (a standard biological technique) or NanoString probes. Four steps broadly describe how the disclosure would be applied in practice:

1) Perform standard Pap smear or endometrial biopsy procedure.
2) Place some or all of the collected tissue into a standard RNA-preserving media such as RNAlater or RLT Buffer.
3a) Isolate and convert collected RNA to cDNA and perform standard RT-qPCR using PCR primers that are specific to the mRNA isoforms comprising the detection test. OR
3b) Apply NanoString technology directly to the collected RNA using probes developed specifically for the mRNA isoforms comprising the detection test, e.g., two non-overlapping probes.
4. Use measurements from 3a) or 3b) as input to a statistical model, which will output a likelihood/probability/confidence for the presence of an ovarian tumor growing in the patient's body.

REFERENCES

Adam et al., *Clin. Cancer Res.*, _:_(2013).
Annala et al., *Cancer Lett.*, 340:192 (2013).
Bustin et al., *Clin. Chem.*, 55:611 (2009).
Chvatal, *Math Oper. Res.*, 1979:4(3):233-5.
Cormen et al., Introduction to Algorithms. Cambridge, Mass.: MIT Press
Coulie et al., *Nat. Rev. Cancer.* 4:135 (2014).
David et al., *Genes Dev.*, 24:2343 (2010).
Dobin et al., *Bioinforma*, _:_(2012).
Dobolyi et al., *Frontiers Media SA*, 3:121 (2012).
Dwight et al., *Bioinformatics*, 27:1019 (2011).
Farhangfar et al., *Clin Chem.*, 59:38 (2013).
Fritsch et al., *Cancer Immunol. Res.*, _:_(2014).
Ge et al., *Genomics.* 86:127 (2005).
Gonzalez-Galarza et al., *Nucleic Acids Res.*, 39:D913 (2011).
Harrow et al., *Genome Res.*, 22:1760 (2012).
Hellemans et al., *Genome Biol.*, 8:R19 (2007).
Hemler, *Nat Rev Cancer.* 14:49 (2013).
Howald et al., *Genome Res.*, 22:1698 (2012).
Hsu et al., *Bioinformatics*, 22:1036 (2006).
Human lincRNA Catalog [Internet]. [cited 2014 Feb. 4]. Available from: http://www.broadinstitute.org/genome_bio/human_lincrnas/
Hwang et al., *Carcinogenesis.* 33:77 (2012).
Kessler et al., *Int. J. Mol. Sci.*, 14:6571 (2013).
Kim et al., *Proc. Natl. Acad. Sci. USA.* 109:3921 (2012).
Kinde et al., *Sci. Transl. Med.*, 5:167ra4 (2013).
Lam et al., *Front Oncol.*, 3:11 (2013).
Lee et al., *J. Pathol.*, 211:26 (2007).
Leth-Larsen et al., *Mol. Med.* 2012 January; 18:1109-21.
Lin et al., *Nucleic Acids Res.*, 40:8460 (2012).
Lonsdale et al., *Nat Genet.*, 45:580 (2013).
Lupetti et al., *J. Exp. Med.*, 188:1005 (1998).
Mailman et al., *Nat. Genet.*, 39:1181 (2007).
Marquez et al., *Clin. Cancer Res.*, 11:6116 (2005).
Marusyk et al., *Nat. Rev. Cancer,* 12:323 (2012).
Mercer et al., 30:99 (2012).
Nielsen et al., *PLoS One*, 2:e796 (2007).
O'Shannessy et al., *Int. J. Mol. Sci.*, 14:13687 (2013).
Oh et al., *Biochim. Biophys. Acta.*, 1826:1 (2012).
Pruitt et al., *Nucleic Acids Res.*, 35:D61 (2007).
Qu et al., *Nucleic Acids Res.*, 40:W205 (2012).
Rao et al., *J. Comput. Biol.*, 20:1 (2013).
Reaves et al., *Public Library of Science.* 9:e91747 (2014).
Reva et al., *Nucleic Acids Res.*, 39:e118 (2011).
Roberts et al., *Nat. Biotechnol.* 10: (2013).
Rousseaux et al., *Sci. Transl. Med.*, 5:186ra66 (2013).
Savitzky et al., *Anal. Chem.*, 36:1627 (1964).

Sproul et al., *Genome Biol.,* 13:R84 (2012).
Swanton, *Cancer Res.,* 72:4875 (2012).
TCGA, *Nature.* 474:609 (2011).
Teh, *Front Oncol. Frontiers,* 2:146 (2012).
The Cancer Genome Atlas [Internet]. Available from: http://cancergenome.nih.gov
The Cancer Genome Atlas [Internet]. Available from: http://cancergenome.nih.gov
The Cancer Genome Atlas Network, *Nature,* 490:61 (2012).
Thierry-Mieg, *Genome Biol.,* 7:1 (2006).
Tothill et al., *Clin. Cancer Res.,* 14:5198 (2008).
Trapnell et al., *Nat. Biotechnol.,* _:_(2010).
Untergasser et al., *Nucleic Acids Res.,* 40:e115 (2012).
Venables et al., *Nat. Struct. Mol. Biol.,* 16:670 (2009).
Verhaak et al., *J. Clin. Invest.,* 123:517 (2013).
Weatheritt et al., *Trends Biochem Sci.,* 37:333 (2012).
Wu et al., *BMC Bioinformatics,* 14:S8 (2013).
Yamasaki et al., *Nucleic Acids Res.* 36:D793 (2008).
Zangi et al., *Nat. Biotechnol.,* 31:898 (2013).
Zhao et al., *Molecules.* 17:6196 (2012).
Zhou et al., *Pharmaceuticals.* 6:85 (2013).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for detecting the presence of ovarian cancer, comprising:
    (a) obtaining amplified nucleic acid from a cervical or endometrial sample from a human patient, wherein the amplified nucleic acid is obtained using at least one primer having a nucleotide sequence comprising SEQ ID NO: 93, SEQ ID NO:94, SEQ ID NO:115, or SEQ ID NO:116, or at least one primer having at least 80% identity thereto; (b) measuring in the sample the amount of at least one mRNA isoform of MYLPF having a sequence comprising MYLPF-specific sequences in SEQ ID NO:93 and in the complement of SEQ ID NO:94 and at least one mRNA isoform of LSR having a sequence comprising LSR-specific sequences in SEQ ID NO:115 and in the complement of SEQ ID NO:116; and (c) determining whether the amount of the least one mRNA isoform of MYLPF having a sequence comprising MYLPF-specific sequences in SEQ ID NO:93 and in the complement of SEQ ID NO:94 and of the at least one mRNA isoform of LSR having a sequence comprising LSR-specific sequences in SEQ ID NO:115 and in the complement of SEQ ID NO:116 in the sample from the human patient is increased relative to the amount of the at least one mRNA isoform of MYLPF and the at least one mRNA isoform of LSR in a corresponding normal sample, wherein an increased amount of the at least one mRNA isoform of MYLPF and of the at least one mRNA isoform of LSR in the sample from the human patient is indicative of ovarian cancer in the human patient.

2. The method of claim 1 wherein the sample is from the cervix.

3. The method of claim 1, further comprising determining the presence or amount of RAB11FIP4, AURKA, or CDCA5.

4. The method of claim 1, wherein the method employs at least two primers comprising a nucleotide sequence selected from: SEQ ID NO:93 or a sequence having at least 80% identity thereto, SEQ ID NO:94 or a sequence having at least 80% thereto, SEQ ID NO:115 or a sequence having at least 80% identity thereto, and SEQ ID NO:116 or a sequence having at least 80% identity thereto, respectively.

5. The method of claim 4, wherein the at least two primers have a nucleotide sequence comprising SEQ ID NO: 93 and 94 respectively, or SEQ ID NO: 115 and 116 respectively.

6. The method of claim 1 wherein a nucleic acid probe is employed to measure the amount of the isoform.

7. The method of claim 1 wherein the amount of the isoform is indicative of high grade serous ovarian carcinoma.

8. The method of claim 1 further comprising measuring a biomarker selected from: ApoC1, Hemoglobin alpha/beta, ApoAII, ApoCII, Calcyclin, Calgranulin C, Calgranulin C (truncated form), Calgranulin A or IgG heavy chain.

9. The method of claim 1 further comprising measuring CA125 II, CA1 5-3, CA1 9-9, CA72-4, CA 195, CEA, creatine kinase B (CKB), Dianon NB 70/K, haptoglobin, ITIH4, galactosyltransferase, haptoglobin, HE4, hepcidin, HER-2/neu, macrophage colony stimulating factor (M-CSF, CSF-I), prostatin, osteopontin, esoinophil-derived neurotoxin, extracellular domain of the epidermal growth factor receptor (p 11 OEGFR), kallikrein 6 and kallikrein 10, LASA, leptin, lysophosphatidic acid (LPA), placental alkaline phosphatase (PLAP), prolactin, SMRP, insulin-like growth factor I, IGF-II, hemoglobin, urinary gonadotropin peptide, Sialyl TN, Tissue peptide antigen (TPA), or tumor associated trypsin inhibitor (TATI), and modified forms thereof.

10. The method of claim 1 further comprising determining the presence or amount of mRNA isoforms of OPN3, RP11-3JL1, TMPRSS3, ETV4, SLC44A4, ESR1, TNFRSF8, or MUC16.

11. The method of claim 1 further comprising determining the presence or amount of mRNA isoforms of RAB11FIP4, AURKA, huhare, STON2, FOXM1, CTD-2616J11.4, AC0191171, CD9, PTH2R, SPC24, LINC00284, or C19orf53.

12. The method of claim 1 further comprising determining the presence or amount of a mRNA isoform of OPN3, RP11-3JL1, TMPRSS3, ETV4, SLC44A4, ESR1, TNFRSF8, SLC44A4, MUC16, RAB11FIP4, AURKA, huhare, STON2, FOXM1, CTD-2616J11.4, AC0191171, CD9, PTH2R, SPC24, LINC00284, or C19orf53, or any combination thereof.

13. The method of claim 1, further comprising determining the presence or amount of at least 2, at least 5, at least 10, at least 12, or at least 20 additional mRNA isoforms.

14. The method of claim 1 wherein the amount is determined using RT-qPCR, hybridization with one or more probes that detect the one or more isoforms, or RNA sequencing.

15. The method of claim 1 wherein the isoform of MYLPF that is measured is ENST0000563728.1.

16. The method of claim 1 wherein the isoform of LSR that is measured is uc002nyp.3.

17. The method of claim 1, further comprising determining the presence or amount of at least one mRNA isoform of RAB1 FIP4, AURKA, CDCA5, PRAME, FGFRL1, OPN3, RPI 1-3J1.1, TMPRSS3, CHODL, ETV4, VTCN1, SLC22A18, SLC44A4, huhare, STON2, CDH24, FOXM1, CTD-2616J11.4, ESR1, AC019117 1, CD9, VASN, WFDC2, PTH2R, TNFRSF8, FOXM1, SPC24, SLC44A4, LINC00284, C19orf53, or MUC16.

18. A method for detecting the presence of ovarian cancer, comprising:
    (a) amplifying nucleic acid from a cervical or endometrial sample from a human patient with a set of primers, wherein one set of primers has a nucleotide sequence comprising SEQ ID NO: 93 or a sequence with at least 80% identity thereto, and one comprising SEQ ID NO:94 or a sequence with at least 80% identity thereto, and another set of primers has a nucleotide sequence comprising SEQ ID NO: 115 or a sequence with at least 80% identity thereto, and one comprising SEQ ID NO: 116 or sequence having at least 80% identity;
    (b) detecting in the sample the presence or the amount of at least one mRNA isoform of MYLPF having a sequence comprising MYLPF-specific sequences in SEQ ID NO:93 and in the complement of SEQ ID NO:94 and at least one mRNA isoform of LSR having a sequence comprising LSR-specific sequences in SEQ ID NO: 115 and in the complement of SEQ ID NO: 116; and
    (c) determining: i) whether the amount of the at least one mRNA isoform of MYLPF and the at least one mRNA isoform of LSR in the sample from the human patient is increased relative to the amount of the at least one mRNA isoform of MYLPF and the at least one mRNA isoform of LSR in a corresponding normal sample, wherein an increased amount of the at least one mRNA isoform of MYLPF and of the at least one mRNA isoform of LSR in the sample from the human patient is indicative of ovarian cancer in the human patient, or
ii) the presence of the at least one mRNA isoform of MYLPF and the at least one mRNA isoform of LSR in the sample from the human patient relative to the at least one mRNA isoform of MYLPF and the at least one mRNA isoform of LSR in a corresponding normal sample, wherein the presence of the at least one mRNA isoform of MYLPF and of the at least one mRNA isoform of LSR in the sample from the human patient and the absence of the at least one mRNA isoform of MYLPF and the at least one mRNA isoform of LSR in a corresponding normal sample is indicative of ovarian cancer in the human patient.

* * * * *

SEQUENCE LISTING

```
<160> NUMBER OF SEQ ID NOS: 147

<210> SEQ ID NO 1
<211> LENGTH: 20
<212> TYPE: DNA
<213> ORGANISM: Artificial Sequence
<220> FEATURE:
<223> OTHER INFORMATION: A synthetic primer

<400> SEQUENCE: 1
tcggtgaaga gacagggtct                                              20

<210> SEQ ID NO 2
<211> LENGTH: 18
<212> TYPE: DNA
<213> ORGANISM: Artificial Sequence
<220> FEATURE:
<223> OTHER INFORMATION: A synthetic primer

<400> SEQUENCE: 2
gaagccttcg gtccgcat                                                18

<210> SEQ ID NO 3
<211> LENGTH: 19
<212> TYPE: DNA
<213> ORGANISM: Artificial Sequence
<220> FEATURE:
<223> OTHER INFORMATION: A synthetic primer

<400> SEQUENCE: 3
gctggagatg agacccagc                                               19

<210> SEQ ID NO 4
<211> LENGTH: 18
<212> TYPE: DNA
<213> ORGANISM: Artificial Sequence
<220> FEATURE:
<223> OTHER INFORMATION: A synthetic primer

<400> SEQUENCE: 4
caggtgtcct ccctccca                                                18

<210> SEQ ID NO 5
<211> LENGTH: 23
<212> TYPE: DNA
<213> ORGANISM: Artificial Sequence
<220> FEATURE:
<223> OTHER INFORMATION: A synthetic primer

<400> SEQUENCE: 5
```

```
gctgactttg aagactatgt gga                                             23

<210> SEQ ID NO 6
<211> LENGTH: 18
<212> TYPE: DNA
<213> ORGANISM: Artificial Sequence
<220> FEATURE:
<223> OTHER INFORMATION: A synthetic primer

<400> SEQUENCE: 6
acctgggcgg tctctaca                                                   18

<210> SEQ ID NO 7
<211> LENGTH: 18
<212> TYPE: DNA
<213> ORGANISM: Artificial Sequence
<220> FEATURE:
<223> OTHER INFORMATION: A synthetic primer

<400> SEQUENCE: 7
tgaccgacgc caacatgg                                                   18

<210> SEQ ID NO 8
<211> LENGTH: 19
<212> TYPE: DNA
<213> ORGANISM: Artificial Sequence
<220> FEATURE:
<223> OTHER INFORMATION: A synthetic primer

<400> SEQUENCE: 8
ctgaagaaac tgcagccgg                                                  19

<210> SEQ ID NO 9
<211> LENGTH: 23
<212> TYPE: DNA
<213> ORGANISM: Artificial Sequence
<220> FEATURE:
<223> OTHER INFORMATION: A synthetic primer

<400> SEQUENCE: 9
cagtaatggg atgagtgaca ttc                                             23

<210> SEQ ID NO 10
<211> LENGTH: 21
<212> TYPE: DNA
<213> ORGANISM: Artificial Sequence
<220> FEATURE:
<223> OTHER INFORMATION: A synthetic primer

<400> SEQUENCE: 10
tgaaatatcc tggcaatggg c                                               21

<210> SEQ ID NO 11
<211> LENGTH: 18
<212> TYPE: DNA
<213> ORGANISM: Artificial Sequence
<220> FEATURE:
<223> OTHER INFORMATION: A synthetic primer

<400> SEQUENCE: 11
agagatgcca ggctcact                                                   18

<210> SEQ ID NO 12
<211> LENGTH: 18
<212> TYPE: DNA
```

```
<213> ORGANISM: Artificial Sequence
<220> FEATURE:
<223> OTHER INFORMATION: A synthetic primer

<400> SEQUENCE: 12
tctgaatgtg ctgccccc                                                       18

<210> SEQ ID NO 13
<211> LENGTH: 18
<212> TYPE: DNA
<213> ORGANISM: Artificial Sequence
<220> FEATURE:
<223> OTHER INFORMATION: A synthetic primer

<400> SEQUENCE: 13
cagtgggtgg agctgcag                                                       18

<210> SEQ ID NO 14
<211> LENGTH: 19
<212> TYPE: DNA
<213> ORGANISM: Artificial Sequence
<220> FEATURE:
<223> OTHER INFORMATION: A synthetic primer

<400> SEQUENCE: 14
aggggcactg tttccatgc                                                      19

<210> SEQ ID NO 15
<211> LENGTH: 18
<212> TYPE: DNA
<213> ORGANISM: Artificial Sequence
<220> FEATURE:
<223> OTHER INFORMATION: A synthetic primer

<400> SEQUENCE: 15
tcagcaagac cccacagg                                                       18

<210> SEQ ID NO 16
<211> LENGTH: 18
<212> TYPE: DNA
<213> ORGANISM: Artificial Sequence
<220> FEATURE:
<223> OTHER INFORMATION: A synthetic primer

<400> SEQUENCE: 16
aggcgcgttc tccagttc                                                       18

<210> SEQ ID NO 17
<211> LENGTH: 18
<212> TYPE: DNA
<213> ORGANISM: Artificial Sequence
<220> FEATURE:
<223> OTHER INFORMATION: A synthetic primer

<400> SEQUENCE: 17
ctgtggcagg gtgttcga                                                       18

<210> SEQ ID NO 18
<211> LENGTH: 18
<212> TYPE: DNA
<213> ORGANISM: Artificial Sequence
<220> FEATURE:
<223> OTHER INFORMATION: A synthetic primer

<400> SEQUENCE: 18
ccacgaccac ctgggaag                                                       18
```

<210> SEQ ID NO 19
<211> LENGTH: 18
<212> TYPE: DNA
<213> ORGANISM: Artificial Sequence
<220> FEATURE:
<223> OTHER INFORMATION: A synthetic primer

<400> SEQUENCE: 19
tgcaggaggc tcaggact                                                 18

<210> SEQ ID NO 20
<211> LENGTH: 18
<212> TYPE: DNA
<213> ORGANISM: Artificial Sequence
<220> FEATURE:
<223> OTHER INFORMATION: A synthetic primer

<400> SEQUENCE: 20
acagcgttcg ctctgcat                                                 18

<210> SEQ ID NO 21
<211> LENGTH: 18
<212> TYPE: DNA
<213> ORGANISM: Artificial Sequence
<220> FEATURE:
<223> OTHER INFORMATION: A synthetic primer

<400> SEQUENCE: 21
acatggttgg tgcgggag                                                 18

<210> SEQ ID NO 22
<211> LENGTH: 20
<212> TYPE: DNA
<213> ORGANISM: Artificial Sequence
<220> FEATURE:
<223> OTHER INFORMATION: A synthetic primer

<400> SEQUENCE: 22
actgcttcat catcaggggc                                               20

<210> SEQ ID NO 23
<211> LENGTH: 18
<212> TYPE: DNA
<213> ORGANISM: Artificial Sequence
<220> FEATURE:
<223> OTHER INFORMATION: A synthetic primer

<400> SEQUENCE: 23
aagccctgac ccaaaggc                                                 18

<210> SEQ ID NO 24
<211> LENGTH: 18
<212> TYPE: DNA
<213> ORGANISM: Artificial Sequence
<220> FEATURE:
<223> OTHER INFORMATION: A synthetic primer

<400> SEQUENCE: 24
agccagtgcg ttcctcag                                                 18

<210> SEQ ID NO 25
<211> LENGTH: 18
<212> TYPE: DNA
<213> ORGANISM: Artificial Sequence
<220> FEATURE:

```
<223> OTHER INFORMATION: A synthetic primer

<400> SEQUENCE: 25
ttggggaggc agtgttcc                                                 18

<210> SEQ ID NO 26
<211> LENGTH: 18
<212> TYPE: DNA
<213> ORGANISM: Artificial Sequence
<220> FEATURE:
<223> OTHER INFORMATION: A synthetic primer

<400> SEQUENCE: 26
tggcgtaggg atgggtgt                                                 18

<210> SEQ ID NO 27
<211> LENGTH: 18
<212> TYPE: DNA
<213> ORGANISM: Artificial Sequence
<220> FEATURE:
<223> OTHER INFORMATION: A synthetic primer

<400> SEQUENCE: 27
tccgtgcctc caatggtg                                                 18

<210> SEQ ID NO 28
<211> LENGTH: 22
<212> TYPE: DNA
<213> ORGANISM: Artificial Sequence
<220> FEATURE:
<223> OTHER INFORMATION: A synthetic primer

<400> SEQUENCE: 28
tgtgccccaa gtaattttct gc                                            22

<210> SEQ ID NO 29
<211> LENGTH: 18
<212> TYPE: DNA
<213> ORGANISM: Artificial Sequence
<220> FEATURE:
<223> OTHER INFORMATION: A synthetic primer

<400> SEQUENCE: 29
gctgaccaca ctcacccc                                                 18

<210> SEQ ID NO 30
<211> LENGTH: 20
<212> TYPE: DNA
<213> ORGANISM: Artificial Sequence
<220> FEATURE:
<223> OTHER INFORMATION: A synthetic primer

<400> SEQUENCE: 30
agccagtttc accagatcct                                               20

<210> SEQ ID NO 31
<211> LENGTH: 19
<212> TYPE: DNA
<213> ORGANISM: Artificial Sequence
<220> FEATURE:
<223> OTHER INFORMATION: A synthetic primer

<400> SEQUENCE: 31
tggtgcaacc atcctgaag                                                19
```

```
<210> SEQ ID NO 32
<211> LENGTH: 23
<212> TYPE: DNA
<213> ORGANISM: Artificial Sequence
<220> FEATURE:
<223> OTHER INFORMATION: A synthetic primer

<400> SEQUENCE: 32
ctgctgcaat aataaccact gaa                                               23

<210> SEQ ID NO 33
<211> LENGTH: 23
<212> TYPE: DNA
<213> ORGANISM: Artificial Sequence
<220> FEATURE:
<223> OTHER INFORMATION: A synthetic primer

<400> SEQUENCE: 33
ttaacaggtg ctaaagtcag agc                                               23

<210> SEQ ID NO 34
<211> LENGTH: 18
<212> TYPE: DNA
<213> ORGANISM: Artificial Sequence
<220> FEATURE:
<223> OTHER INFORMATION: A synthetic primer

<400> SEQUENCE: 34
aaagaagggg gtggggga                                                     18

<210> SEQ ID NO 35
<211> LENGTH: 23
<212> TYPE: DNA
<213> ORGANISM: Artificial Sequence
<220> FEATURE:
<223> OTHER INFORMATION: A synthetic primer

<400> SEQUENCE: 35
cgttatgaga gtcgacttca atg                                               23

<210> SEQ ID NO 36
<211> LENGTH: 19
<212> TYPE: DNA
<213> ORGANISM: Artificial Sequence
<220> FEATURE:
<223> OTHER INFORMATION: A synthetic primer

<400> SEQUENCE: 36
aacatccttg cccagcaga                                                    19

<210> SEQ ID NO 37
<211> LENGTH: 18
<212> TYPE: DNA
<213> ORGANISM: Artificial Sequence
<220> FEATURE:
<223> OTHER INFORMATION: A synthetic primer

<400> SEQUENCE: 37
ctcgtcgggc tccctttg                                                     18

<210> SEQ ID NO 38
<211> LENGTH: 23
<212> TYPE: DNA
<213> ORGANISM: Artificial Sequence
<220> FEATURE:
<223> OTHER INFORMATION: A synthetic primer
```

```
<400> SEQUENCE: 38
accacaccac ggataaaatt gag                                            23

<210> SEQ ID NO 39
<211> LENGTH: 18
<212> TYPE: DNA
<213> ORGANISM: Artificial Sequence
<220> FEATURE:
<223> OTHER INFORMATION: A synthetic primer

<400> SEQUENCE: 39
gcccgaactg caagttgc                                                  18

<210> SEQ ID NO 40
<211> LENGTH: 19
<212> TYPE: DNA
<213> ORGANISM: Artificial Sequence
<220> FEATURE:
<223> OTHER INFORMATION: A synthetic primer

<400> SEQUENCE: 40
ccagattgca accgcttcc                                                 19

<210> SEQ ID NO 41
<211> LENGTH: 18
<212> TYPE: DNA
<213> ORGANISM: Artificial Sequence
<220> FEATURE:
<223> OTHER INFORMATION: A synthetic primer

<400> SEQUENCE: 41
aaggtggtga agcaggcg                                                  18

<210> SEQ ID NO 42
<211> LENGTH: 23
<212> TYPE: DNA
<213> ORGANISM: Artificial Sequence
<220> FEATURE:
<223> OTHER INFORMATION: A synthetic primer

<400> SEQUENCE: 42
cgttgtcata ccaggaaatg agc                                            23

<210> SEQ ID NO 43
<211> LENGTH: 19
<212> TYPE: DNA
<213> ORGANISM: Artificial Sequence
<220> FEATURE:
<223> OTHER INFORMATION: A synthetic primer

<400> SEQUENCE: 43
ttgcagggtt tcaccagga                                                 19

<210> SEQ ID NO 44
<211> LENGTH: 19
<212> TYPE: DNA
<213> ORGANISM: Artificial Sequence
<220> FEATURE:
<223> OTHER INFORMATION: A synthetic primer

<400> SEQUENCE: 44
gcactctcgt cggtgactg                                                 19

<210> SEQ ID NO 45
<211> LENGTH: 18
```

```
<212> TYPE: DNA
<213> ORGANISM: Artificial Sequence
<220> FEATURE:
<223> OTHER INFORMATION: A synthetic primer

<400> SEQUENCE: 45
tggcactggg aaggtcac                                                   18

<210> SEQ ID NO 46
<211> LENGTH: 18
<212> TYPE: DNA
<213> ORGANISM: Artificial Sequence
<220> FEATURE:
<223> OTHER INFORMATION: A synthetic primer

<400> SEQUENCE: 46
ggttcctggc aagctccc                                                   18

<210> SEQ ID NO 47
<211> LENGTH: 19
<212> TYPE: DNA
<213> ORGANISM: Artificial Sequence
<220> FEATURE:
<223> OTHER INFORMATION: A synthetic primer

<400> SEQUENCE: 47
tgctttcctt ggtcaggca                                                  19

<210> SEQ ID NO 48
<211> LENGTH: 23
<212> TYPE: DNA
<213> ORGANISM: Artificial Sequence
<220> FEATURE:
<223> OTHER INFORMATION: A synthetic primer

<400> SEQUENCE: 48
ttcaaatcca acaaagtctg gct                                             23

<210> SEQ ID NO 49
<211> LENGTH: 18
<212> TYPE: DNA
<213> ORGANISM: Artificial Sequence
<220> FEATURE:
<223> OTHER INFORMATION: A synthetic primer

<400> SEQUENCE: 49
caagagatgg ccacggct                                                   18

<210> SEQ ID NO 50
<211> LENGTH: 18
<212> TYPE: DNA
<213> ORGANISM: Artificial Sequence
<220> FEATURE:
<223> OTHER INFORMATION: A synthetic primer

<400> SEQUENCE: 50
aggactccat gcccagga                                                   18

<210> SEQ ID NO 51
<211> LENGTH: 18
<212> TYPE: DNA
<213> ORGANISM: Artificial Sequence
<220> FEATURE:
<223> OTHER INFORMATION: A synthetic primer

<400> SEQUENCE: 51
```

```
ctgcagaggt cgctggtc                                                 18

<210> SEQ ID NO 52
<211> LENGTH: 20
<212> TYPE: DNA
<213> ORGANISM: Artificial Sequence
<220> FEATURE:
<223> OTHER INFORMATION: A synthetic primer

<400> SEQUENCE: 52
tccacgagca gaatacagcc                                               20

<210> SEQ ID NO 53
<211> LENGTH: 19
<212> TYPE: DNA
<213> ORGANISM: Artificial Sequence
<220> FEATURE:
<223> OTHER INFORMATION: A synthetic primer

<400> SEQUENCE: 53
tgccagtgtc tgtctgcag                                                19

<210> SEQ ID NO 54
<211> LENGTH: 20
<212> TYPE: DNA
<213> ORGANISM: Artificial Sequence
<220> FEATURE:
<223> OTHER INFORMATION: A synthetic primer

<400> SEQUENCE: 54
aggccttgac cttttcagca                                               20

<210> SEQ ID NO 55
<211> LENGTH: 18
<212> TYPE: DNA
<213> ORGANISM: Artificial Sequence
<220> FEATURE:
<223> OTHER INFORMATION: A synthetic primer

<400> SEQUENCE: 55
gcacagcctg gctcctttt                                                18

<210> SEQ ID NO 56
<211> LENGTH: 19
<212> TYPE: DNA
<213> ORGANISM: Artificial Sequence
<220> FEATURE:
<223> OTHER INFORMATION: A synthetic primer

<400> SEQUENCE: 56
ggcgcctcat caaatcctg                                                19

<210> SEQ ID NO 57
<211> LENGTH: 19
<212> TYPE: DNA
<213> ORGANISM: Artificial Sequence
<220> FEATURE:
<223> OTHER INFORMATION: A synthetic primer

<400> SEQUENCE: 57
aaagcatacg ggtcctggc                                                19

<210> SEQ ID NO 58
<211> LENGTH: 19
<212> TYPE: DNA
<213> ORGANISM: Artificial Sequence
```

```
<220> FEATURE:
<223> OTHER INFORMATION: A synthetic primer

<400> SEQUENCE: 58
tgcttgccat ccaaccact                                                   19

<210> SEQ ID NO 59
<211> LENGTH: 18
<212> TYPE: DNA
<213> ORGANISM: Artificial Sequence
<220> FEATURE:
<223> OTHER INFORMATION: A synthetic primer

<400> SEQUENCE: 59
tggccgcatg aagatcga                                                    18

<210> SEQ ID NO 60
<211> LENGTH: 21
<212> TYPE: DNA
<213> ORGANISM: Artificial Sequence
<220> FEATURE:
<223> OTHER INFORMATION: A synthetic primer

<400> SEQUENCE: 60
ttggaacccc atctttcctg a                                                21

<210> SEQ ID NO 61
<211> LENGTH: 18
<212> TYPE: DNA
<213> ORGANISM: Artificial Sequence
<220> FEATURE:
<223> OTHER INFORMATION: A synthetic primer

<400> SEQUENCE: 61
caatgtaggg gccggtgg                                                    18

<210> SEQ ID NO 62
<211> LENGTH: 22
<212> TYPE: DNA
<213> ORGANISM: Artificial Sequence
<220> FEATURE:
<223> OTHER INFORMATION: A synthetic primer

<400> SEQUENCE: 62
cactttcttc tcctcagctg ga                                               22

<210> SEQ ID NO 63
<211> LENGTH: 18
<212> TYPE: DNA
<213> ORGANISM: Artificial Sequence
<220> FEATURE:
<223> OTHER INFORMATION: A synthetic primer

<400> SEQUENCE: 63
taggctcgtc ccaaaggc                                                    18

<210> SEQ ID NO 64
<211> LENGTH: 18
<212> TYPE: DNA
<213> ORGANISM: Artificial Sequence
<220> FEATURE:
<223> OTHER INFORMATION: A synthetic primer

<400> SEQUENCE: 64
ggttcacacg gcaggcat                                                    18
```

```
<210> SEQ ID NO 65
<211> LENGTH: 18
<212> TYPE: DNA
<213> ORGANISM: Artificial Sequence
<220> FEATURE:
<223> OTHER INFORMATION: A synthetic primer

<400> SEQUENCE: 65
ttgctggagc tgcagtct                                                 18

<210> SEQ ID NO 66
<211> LENGTH: 22
<212> TYPE: DNA
<213> ORGANISM: Artificial Sequence
<220> FEATURE:
<223> OTHER INFORMATION: A synthetic primer

<400> SEQUENCE: 66
ggaaccctcc ttatcttggt tc                                            22

<210> SEQ ID NO 67
<211> LENGTH: 22
<212> TYPE: DNA
<213> ORGANISM: Artificial Sequence
<220> FEATURE:
<223> OTHER INFORMATION: A synthetic primer

<400> SEQUENCE: 67
acacaatgtg tcctagaaga ag                                            22

<210> SEQ ID NO 68
<211> LENGTH: 18
<212> TYPE: DNA
<213> ORGANISM: Artificial Sequence
<220> FEATURE:
<223> OTHER INFORMATION: A synthetic primer

<400> SEQUENCE: 68
agctgcccat tcgactgt                                                 18

<210> SEQ ID NO 69
<211> LENGTH: 18
<212> TYPE: DNA
<213> ORGANISM: Artificial Sequence
<220> FEATURE:
<223> OTHER INFORMATION: A synthetic primer

<400> SEQUENCE: 69
gcccccttct cattccga                                                 18

<210> SEQ ID NO 70
<211> LENGTH: 18
<212> TYPE: DNA
<213> ORGANISM: Artificial Sequence
<220> FEATURE:
<223> OTHER INFORMATION: A synthetic primer

<400> SEQUENCE: 70
gcagcaacag catctggt                                                 18

<210> SEQ ID NO 71
<211> LENGTH: 18
<212> TYPE: DNA
<213> ORGANISM: Artificial Sequence
<220> FEATURE:
<223> OTHER INFORMATION: A synthetic primer
```

```
<400> SEQUENCE: 71
ctgggcctga agggaaca                                                    18

<210> SEQ ID NO 72
<211> LENGTH: 18
<212> TYPE: DNA
<213> ORGANISM: Artificial Sequence
<220> FEATURE:
<223> OTHER INFORMATION: A synthetic primer

<400> SEQUENCE: 72
agggtgtcca ggcgtatg                                                    18

<210> SEQ ID NO 73
<211> LENGTH: 18
<212> TYPE: DNA
<213> ORGANISM: Artificial Sequence
<220> FEATURE:
<223> OTHER INFORMATION: A synthetic primer

<400> SEQUENCE: 73
ggcgagcagt gcctttac                                                    18

<210> SEQ ID NO 74
<211> LENGTH: 19
<212> TYPE: DNA
<213> ORGANISM: Artificial Sequence
<220> FEATURE:
<223> OTHER INFORMATION: A synthetic primer

<400> SEQUENCE: 74
cgcacccggt gacatctat                                                   19

<210> SEQ ID NO 75
<211> LENGTH: 18
<212> TYPE: DNA
<213> ORGANISM: Artificial Sequence
<220> FEATURE:
<223> OTHER INFORMATION: A synthetic primer

<400> SEQUENCE: 75
ggcgtgaatg cgtggatt                                                    18

<210> SEQ ID NO 76
<211> LENGTH: 18
<212> TYPE: DNA
<213> ORGANISM: Artificial Sequence
<220> FEATURE:
<223> OTHER INFORMATION: A synthetic primer

<400> SEQUENCE: 76
tgccacgcac gtgttttt                                                    18

<210> SEQ ID NO 77
<211> LENGTH: 18
<212> TYPE: DNA
<213> ORGANISM: Artificial Sequence
<220> FEATURE:
<223> OTHER INFORMATION: A synthetic primer

<400> SEQUENCE: 77
gccgtggtgg tgtattgc                                                    18

<210> SEQ ID NO 78
```

```
<211> LENGTH: 18
<212> TYPE: DNA
<213> ORGANISM: Artificial Sequence
<220> FEATURE:
<223> OTHER INFORMATION: A synthetic primer

<400> SEQUENCE: 78
cacatcactg ggcgttcg                                                 18

<210> SEQ ID NO 79
<211> LENGTH: 18
<212> TYPE: DNA
<213> ORGANISM: Artificial Sequence
<220> FEATURE:
<223> OTHER INFORMATION: A synthetic primer

<400> SEQUENCE: 79
gctgctggaa acgcaaga                                                 18

<210> SEQ ID NO 80
<211> LENGTH: 18
<212> TYPE: DNA
<213> ORGANISM: Artificial Sequence
<220> FEATURE:
<223> OTHER INFORMATION: A synthetic primer

<400> SEQUENCE: 80
ctgtcgctcc tgctcctt                                                 18

<210> SEQ ID NO 81
<211> LENGTH: 20
<212> TYPE: DNA
<213> ORGANISM: Artificial Sequence
<220> FEATURE:
<223> OTHER INFORMATION: A synthetic primer

<400> SEQUENCE: 81
aggttccttg aacagctgga                                               20

<210> SEQ ID NO 82
<211> LENGTH: 18
<212> TYPE: DNA
<213> ORGANISM: Artificial Sequence
<220> FEATURE:
<223> OTHER INFORMATION: A synthetic primer

<400> SEQUENCE: 82
cactgttcct ctgggcca                                                 18

<210> SEQ ID NO 83
<211> LENGTH: 18
<212> TYPE: DNA
<213> ORGANISM: Artificial Sequence
<220> FEATURE:
<223> OTHER INFORMATION: A synthetic primer

<400> SEQUENCE: 83
gctgacctcg cgcataat                                                 18

<210> SEQ ID NO 84
<211> LENGTH: 18
<212> TYPE: DNA
<213> ORGANISM: Artificial Sequence
<220> FEATURE:
<223> OTHER INFORMATION: A synthetic primer

<400> SEQUENCE: 84
```
ctgtccggcc tctgaaca                                               18

<210> SEQ ID NO 85
<211> LENGTH: 18
<212> TYPE: DNA
<213> ORGANISM: Artificial Sequence
<220> FEATURE:
<223> OTHER INFORMATION: A synthetic primer

<400> SEQUENCE: 85
tcactgtcgc ccagaagg                                               18

<210> SEQ ID NO 86
<211> LENGTH: 18
<212> TYPE: DNA
<213> ORGANISM: Artificial Sequence
<220> FEATURE:
<223> OTHER INFORMATION: A synthetic primer

<400> SEQUENCE: 86
cgctgatccc ctgctgta                                               18

<210> SEQ ID NO 87
<211> LENGTH: 18
<212> TYPE: DNA
<213> ORGANISM: Artificial Sequence
<220> FEATURE:
<223> OTHER INFORMATION: A synthetic primer

<400> SEQUENCE: 87
ccggcattct acaggcca                                               18

<210> SEQ ID NO 88
<211> LENGTH: 19
<212> TYPE: DNA
<213> ORGANISM: Artificial Sequence
<220> FEATURE:
<223> OTHER INFORMATION: A synthetic primer

<400> SEQUENCE: 88
tccacaaagc cacctttca                                              19

<210> SEQ ID NO 89
<211> LENGTH: 18
<212> TYPE: DNA
<213> ORGANISM: Artificial Sequence
<220> FEATURE:
<223> OTHER INFORMATION: A synthetic primer

<400> SEQUENCE: 89
gccttcccac aggatcga                                               18

<210> SEQ ID NO 90
<211> LENGTH: 18
<212> TYPE: DNA
<213> ORGANISM: Artificial Sequence
<220> FEATURE:
<223> OTHER INFORMATION: A synthetic primer

<400> SEQUENCE: 90
actgctgtgt cgggaaca                                               18

<210> SEQ ID NO 91
<211> LENGTH: 18
<212> TYPE: DNA

```
<213> ORGANISM: Artificial Sequence
<220> FEATURE:
<223> OTHER INFORMATION: A synthetic primer

<400> SEQUENCE: 91
cctatcgggc cctgttgg                                                 18

<210> SEQ ID NO 92
<211> LENGTH: 18
<212> TYPE: DNA
<213> ORGANISM: Artificial Sequence
<220> FEATURE:
<223> OTHER INFORMATION: A synthetic primer

<400> SEQUENCE: 92
tgtagggctt tgcgtgga                                                 18

<210> SEQ ID NO 93
<211> LENGTH: 18
<212> TYPE: DNA
<213> ORGANISM: Artificial Sequence
<220> FEATURE:
<223> OTHER INFORMATION: A synthetic primer

<400> SEQUENCE: 93
accaggaacc caatcgca                                                 18

<210> SEQ ID NO 94
<211> LENGTH: 21
<212> TYPE: DNA
<213> ORGANISM: Artificial Sequence
<220> FEATURE:
<223> OTHER INFORMATION: A synthetic primer

<400> SEQUENCE: 94
gcccacatgt tcttgatctc c                                             21

<210> SEQ ID NO 95
<211> LENGTH: 18
<212> TYPE: DNA
<213> ORGANISM: Artificial Sequence
<220> FEATURE:
<223> OTHER INFORMATION: A synthetic primer

<400> SEQUENCE: 95
cggcctcaaa cccaaacc                                                 18

<210> SEQ ID NO 96
<211> LENGTH: 18
<212> TYPE: DNA
<213> ORGANISM: Artificial Sequence
<220> FEATURE:
<223> OTHER INFORMATION: A synthetic primer

<400> SEQUENCE: 96
ggctcctcaa ccacaggt                                                 18

<210> SEQ ID NO 97
<211> LENGTH: 18
<212> TYPE: DNA
<213> ORGANISM: Artificial Sequence
<220> FEATURE:
<223> OTHER INFORMATION: A synthetic primer

<400> SEQUENCE: 97
gtccccctgc tcctgatc                                                 18
```

<210> SEQ ID NO 98
<211> LENGTH: 18
<212> TYPE: DNA
<213> ORGANISM: Artificial Sequence
<220> FEATURE:
<223> OTHER INFORMATION: A synthetic primer

<400> SEQUENCE: 98
tcccctcctc agctagca                                                   18

<210> SEQ ID NO 99
<211> LENGTH: 20
<212> TYPE: DNA
<213> ORGANISM: Artificial Sequence
<220> FEATURE:
<223> OTHER INFORMATION: A synthetic primer

<400> SEQUENCE: 99
cccaagaaaa ggcggtaagg                                                 20

<210> SEQ ID NO 100
<211> LENGTH: 23
<212> TYPE: DNA
<213> ORGANISM: Artificial Sequence
<220> FEATURE:
<223> OTHER INFORMATION: A synthetic primer

<400> SEQUENCE: 100
acttctaggt tcttcttgag ctt                                             23

<210> SEQ ID NO 101
<211> LENGTH: 18
<212> TYPE: DNA
<213> ORGANISM: Artificial Sequence
<220> FEATURE:
<223> OTHER INFORMATION: A synthetic primer

<400> SEQUENCE: 101
ggggtcagcg ggacttta                                                   18

<210> SEQ ID NO 102
<211> LENGTH: 18
<212> TYPE: DNA
<213> ORGANISM: Artificial Sequence
<220> FEATURE:
<223> OTHER INFORMATION: A synthetic primer

<400> SEQUENCE: 102
gcaaggacag caatcccg                                                   18

<210> SEQ ID NO 103
<211> LENGTH: 18
<212> TYPE: DNA
<213> ORGANISM: Artificial Sequence
<220> FEATURE:
<223> OTHER INFORMATION: A synthetic primer

<400> SEQUENCE: 103
gcctgggagg tcgtgtta                                                   18

<210> SEQ ID NO 104
<211> LENGTH: 18
<212> TYPE: DNA
<213> ORGANISM: Artificial Sequence
<220> FEATURE:

<223> OTHER INFORMATION: A synthetic primer

<400> SEQUENCE: 104
catcagcaaa ggtggggc                                                   18

<210> SEQ ID NO 105
<211> LENGTH: 19
<212> TYPE: DNA
<213> ORGANISM: Artificial Sequence
<220> FEATURE:
<223> OTHER INFORMATION: A synthetic primer

<400> SEQUENCE: 105
tgagccaatt ccctggaga                                                  19

<210> SEQ ID NO 106
<211> LENGTH: 18
<212> TYPE: DNA
<213> ORGANISM: Artificial Sequence
<220> FEATURE:
<223> OTHER INFORMATION: A synthetic primer

<400> SEQUENCE: 106
gaatcaacgt gctggccc                                                   18

<210> SEQ ID NO 107
<211> LENGTH: 18
<212> TYPE: DNA
<213> ORGANISM: Artificial Sequence
<220> FEATURE:
<223> OTHER INFORMATION: A synthetic primer

<400> SEQUENCE: 107
acttgggtcc ttgggtcg                                                   18

<210> SEQ ID NO 108
<211> LENGTH: 18
<212> TYPE: DNA
<213> ORGANISM: Artificial Sequence
<220> FEATURE:
<223> OTHER INFORMATION: A synthetic primer

<400> SEQUENCE: 108
tgcactccag cctctagc                                                   18

<210> SEQ ID NO 109
<211> LENGTH: 20
<212> TYPE: DNA
<213> ORGANISM: Artificial Sequence
<220> FEATURE:
<223> OTHER INFORMATION: A synthetic primer

<400> SEQUENCE: 109
gaacctgccc accttattgt                                                 20

<210> SEQ ID NO 110
<211> LENGTH: 18
<212> TYPE: DNA
<213> ORGANISM: Artificial Sequence
<220> FEATURE:
<223> OTHER INFORMATION: A synthetic primer

<400> SEQUENCE: 110
ggtcactgca ggcagaga                                                   18

```
<210> SEQ ID NO 111
<211> LENGTH: 18
<212> TYPE: DNA
<213> ORGANISM: Artificial Sequence
<220> FEATURE:
<223> OTHER INFORMATION: A synthetic primer

<400> SEQUENCE: 111
tacagagctc ggctggag                                                 18

<210> SEQ ID NO 112
<211> LENGTH: 18
<212> TYPE: DNA
<213> ORGANISM: Artificial Sequence
<220> FEATURE:
<223> OTHER INFORMATION: A synthetic primer

<400> SEQUENCE: 112
tctggatggc cacttgca                                                 18

<210> SEQ ID NO 113
<211> LENGTH: 18
<212> TYPE: DNA
<213> ORGANISM: Artificial Sequence
<220> FEATURE:
<223> OTHER INFORMATION: A synthetic primer

<400> SEQUENCE: 113
gctcctctgg gggtcaag                                                 18

<210> SEQ ID NO 114
<211> LENGTH: 18
<212> TYPE: DNA
<213> ORGANISM: Artificial Sequence
<220> FEATURE:
<223> OTHER INFORMATION: A synthetic primer

<400> SEQUENCE: 114
gcggttttgg gtcttgca                                                 18

<210> SEQ ID NO 115
<211> LENGTH: 18
<212> TYPE: DNA
<213> ORGANISM: Artificial Sequence
<220> FEATURE:
<223> OTHER INFORMATION: A synthetic primer

<400> SEQUENCE: 115
cctcaggtgt tcccagca                                                 18

<210> SEQ ID NO 116
<211> LENGTH: 18
<212> TYPE: DNA
<213> ORGANISM: Artificial Sequence
<220> FEATURE:
<223> OTHER INFORMATION: A synthetic primer

<400> SEQUENCE: 116
ccactgcgga ctgagcta                                                 18

<210> SEQ ID NO 117
<211> LENGTH: 18
<212> TYPE: DNA
<213> ORGANISM: Artificial Sequence
<220> FEATURE:
<223> OTHER INFORMATION: A synthetic primer
```

<400> SEQUENCE: 117
ggctggaact cagaccca                                        18

<210> SEQ ID NO 118
<211> LENGTH: 18
<212> TYPE: DNA
<213> ORGANISM: Artificial Sequence
<220> FEATURE:
<223> OTHER INFORMATION: A synthetic primer

<400> SEQUENCE: 118
tagagcgctc atcctgcc                                        18

<210> SEQ ID NO 119
<211> LENGTH: 19
<212> TYPE: DNA
<213> ORGANISM: Artificial Sequence
<220> FEATURE:
<223> OTHER INFORMATION: A synthetic primer

<400> SEQUENCE: 119
aactcagctt ccggtcacc                                       19

<210> SEQ ID NO 120
<211> LENGTH: 22
<212> TYPE: DNA
<213> ORGANISM: Artificial Sequence
<220> FEATURE:
<223> OTHER INFORMATION: A synthetic primer

<400> SEQUENCE: 120
tgtttctgtt gtctggtagc tg                                   22

<210> SEQ ID NO 121
<211> LENGTH: 18
<212> TYPE: DNA
<213> ORGANISM: Artificial Sequence
<220> FEATURE:
<223> OTHER INFORMATION: A synthetic primer

<400> SEQUENCE: 121
tacagcaggg gatcagcg                                        18

<210> SEQ ID NO 122
<211> LENGTH: 18
<212> TYPE: DNA
<213> ORGANISM: Artificial Sequence
<220> FEATURE:
<223> OTHER INFORMATION: A synthetic primer

<400> SEQUENCE: 122
tgtcccacag ccacaaga                                        18

<210> SEQ ID NO 123
<211> LENGTH: 18
<212> TYPE: DNA
<213> ORGANISM: Artificial Sequence
<220> FEATURE:
<223> OTHER INFORMATION: A synthetic primer

<400> SEQUENCE: 123
tgctggtgtc cctcttcg                                        18

<210> SEQ ID NO 124
<211> LENGTH: 21

```
<212> TYPE: DNA
<213> ORGANISM: Artificial Sequence
<220> FEATURE:
<223> OTHER INFORMATION: A synthetic primer

<400> SEQUENCE: 124
tgcatttgtg actggaactc t                                            21

<210> SEQ ID NO 125
<211> LENGTH: 23
<212> TYPE: DNA
<213> ORGANISM: Artificial Sequence
<220> FEATURE:
<223> OTHER INFORMATION: A synthetic primer

<400> SEQUENCE: 125
ggaacatcta cacacagagg aaa                                          23

<210> SEQ ID NO 126
<211> LENGTH: 19
<212> TYPE: DNA
<213> ORGANISM: Artificial Sequence
<220> FEATURE:
<223> OTHER INFORMATION: A synthetic primer

<400> SEQUENCE: 126
ggggactgtt gggaatgga                                               19

<210> SEQ ID NO 127
<211> LENGTH: 22
<212> TYPE: DNA
<213> ORGANISM: Artificial Sequence
<220> FEATURE:
<223> OTHER INFORMATION: A synthetic primer

<400> SEQUENCE: 127
tcagaaggca aagattgacc ag                                           22

<210> SEQ ID NO 128
<211> LENGTH: 18
<212> TYPE: DNA
<213> ORGANISM: Artificial Sequence
<220> FEATURE:
<223> OTHER INFORMATION: A synthetic primer

<400> SEQUENCE: 128
tcctgctgag ccaggaac                                                18

<210> SEQ ID NO 129
<211> LENGTH: 18
<212> TYPE: DNA
<213> ORGANISM: Artificial Sequence
<220> FEATURE:
<223> OTHER INFORMATION: A synthetic primer

<400> SEQUENCE: 129
acccatcgga gctctgtg                                                18

<210> SEQ ID NO 130
<211> LENGTH: 20
<212> TYPE: DNA
<213> ORGANISM: Artificial Sequence
<220> FEATURE:
<223> OTHER INFORMATION: A synthetic primer

<400> SEQUENCE: 130
```

```
ggaacagtta cttgtggggc                                              20
```

<210> SEQ ID NO 131
<211> LENGTH: 18
<212> TYPE: DNA
<213> ORGANISM: Artificial Sequence
<220> FEATURE:
<223> OTHER INFORMATION: A synthetic primer

<400> SEQUENCE: 131

```
ctgcagaggt cgctggtc                                                18
```

<210> SEQ ID NO 132
<211> LENGTH: 20
<212> TYPE: DNA
<213> ORGANISM: Artificial Sequence
<220> FEATURE:
<223> OTHER INFORMATION: A synthetic primer

<400> SEQUENCE: 132

```
tccacgagca gaatacagcc                                              20
```

<210> SEQ ID NO 133
<211> LENGTH: 18
<212> TYPE: DNA
<213> ORGANISM: Artificial Sequence
<220> FEATURE:
<223> OTHER INFORMATION: A synthetic primer

<400> SEQUENCE: 133

```
acatggttgg tgcgggag                                                18
```

<210> SEQ ID NO 134
<211> LENGTH: 20
<212> TYPE: DNA
<213> ORGANISM: Artificial Sequence
<220> FEATURE:
<223> OTHER INFORMATION: A synthetic primer

<400> SEQUENCE: 134

```
actgcttcat catcaggggc                                              20
```

<210> SEQ ID NO 135
<211> LENGTH: 19
<212> TYPE: DNA
<213> ORGANISM: Artificial Sequence
<220> FEATURE:
<223> OTHER INFORMATION: A synthetic primer

<400> SEQUENCE: 135

```
aaagcatacg ggtcctggc                                               19
```

<210> SEQ ID NO 136
<211> LENGTH: 19
<212> TYPE: DNA
<213> ORGANISM: Artificial Sequence
<220> FEATURE:
<223> OTHER INFORMATION: A synthetic primer

<400> SEQUENCE: 136

```
tgcttgccat ccaaccact                                               19
```

<210> SEQ ID NO 137
<211> LENGTH: 25
<212> TYPE: PRT
<213> ORGANISM: Artificial Sequence

```
<220> FEATURE:
<223> OTHER INFORMATION: A synthetic protein

<400> SEQUENCE: 137

Met Ala Gly Leu Gly Ala Ser Leu His Val Trp Gly Trp Leu Met Leu
1               5                   10                  15
Gly Ser Cys Leu Leu Ala Arg Ala Gln
            20                  25

<210> SEQ ID NO 138
<211> LENGTH: 36
<212> TYPE: PRT
<213> ORGANISM: Artificial Sequence
<220> FEATURE:
<223> OTHER INFORMATION: A synthetic protein

<400> SEQUENCE: 138

Met Leu Arg Ser Ser Leu Ser Thr Ser Ile Val Leu Phe Leu Phe Ser
1               5                   10                  15
Ser Phe Asp Thr Ile Asn Glu Ser Ile Ser Ser Arg Lys Arg His Arg
            20                  25                  30
Phe Leu Glu Gln
        35

<210> SEQ ID NO 139
<211> LENGTH: 34
<212> TYPE: PRT
<213> ORGANISM: Artificial Sequence
<220> FEATURE:
<223> OTHER INFORMATION: A synthetic protein

<400> SEQUENCE: 139

Leu Asp Ser Asp Gly Thr Ile Thr Ile Glu Glu Gln Ile Val Leu Val
1               5                   10                  15
Leu Lys Ala Lys Val Gln Cys Glu Leu Asn Ile Thr Ala Gln Leu Gln
            20                  25                  30
Glu Gly

<210> SEQ ID NO 140
<211> LENGTH: 20
<212> TYPE: PRT
<213> ORGANISM: Artificial Sequence
<220> FEATURE:
<223> OTHER INFORMATION: A synthetic protein

<400> SEQUENCE: 140

Phe Leu Arg Ser Ser Gly Thr Ser Gln Pro His Pro Gly His Gly Tyr
1               5                   10                  15
Leu Gly Glu His
        20

<210> SEQ ID NO 141
<211> LENGTH: 14
<212> TYPE: PRT
<213> ORGANISM: Artificial Sequence
<220> FEATURE:
<223> OTHER INFORMATION: A synthetic protein

<400> SEQUENCE: 141

Arg Cys His Arg Val Arg Ile Asn Val Pro Pro His Arg Gly
1               5                   10

<210> SEQ ID NO 142
```

```
<211> LENGTH: 12
<212> TYPE: PRT
<213> ORGANISM: Artificial Sequence
<220> FEATURE:
<223> OTHER INFORMATION: A synthetic protein

<400> SEQUENCE: 142

Arg Ala Arg Arg Ala Gln Thr Ala Ala Met Ala Leu
1               5                   10

<210> SEQ ID NO 143
<211> LENGTH: 12
<212> TYPE: PRT
<213> ORGANISM: Artificial Sequence
<220> FEATURE:
<223> OTHER INFORMATION: A synthetic protein

<400> SEQUENCE: 143

Ala Ile Gln Val Thr Val Ser Asn Pro Tyr His Val
1               5                   10

<210> SEQ ID NO 144
<211> LENGTH: 10
<212> TYPE: PRT
<213> ORGANISM: Artificial Sequence
<220> FEATURE:
<223> OTHER INFORMATION: A synthetic protein

<400> SEQUENCE: 144

Ala Met Ala Leu Ala Ile Gln Val Thr Val
1               5                   10

<210> SEQ ID NO 145
<211> LENGTH: 9
<212> TYPE: PRT
<213> ORGANISM: Artificial Sequence
<220> FEATURE:
<223> OTHER INFORMATION: A synthetic protein

<400> SEQUENCE: 145

Met Ala Leu Ala Ile Gln Val Thr Val
1               5

<210> SEQ ID NO 146
<211> LENGTH: 11
<212> TYPE: PRT
<213> ORGANISM: Artificial Sequence
<220> FEATURE:
<223> OTHER INFORMATION: A synthetic protein

<400> SEQUENCE: 146

Leu Ala Ile Gln Val Thr Val Ser Asn Pro Tyr
1               5                   10

<210> SEQ ID NO 147
<211> LENGTH: 10
<212> TYPE: PRT
<213> ORGANISM: Artificial Sequence
<220> FEATURE:
<223> OTHER INFORMATION: A synthetic protein

<400> SEQUENCE: 147

Ala Ala Met Ala Leu Ala Ile Gln Val Thr
1               5                   10
```